(12) United States Patent
Van Der Oost

(10) Patent No.: US 11,479,761 B2
(45) Date of Patent: Oct. 25, 2022

(54) NUCLEASE-MEDIATED GENOME EDITING

(71) Applicant: Wageningen Universiteit, Wageningen (NL)

(72) Inventor: John Van Der Oost, Renkum (NL)

(73) Assignee: WAGENINGEN UNIVERSITEIT, Wageningen (NL)

( * ) Notice: Subject to any disclaimer, the term of this patent is extended or adjusted under 35 U.S.C. 154(b) by 0 days.

(21) Appl. No.: 16/400,021

(22) Filed: Apr. 30, 2019

(65) Prior Publication Data

US 2020/0010817 A1 Jan. 9, 2020

Related U.S. Application Data

(63) Continuation of application No. 15/566,528, filed as application No. PCT/EP2016/058442 on Apr. 15, 2016, now Pat. No. 11,053,482.

(60) Provisional application No. 62/269,143, filed on Dec. 18, 2015, provisional application No. 62/312,724, filed on Mar. 24, 2016.

(30) Foreign Application Priority Data

Apr. 16, 2015 (GB) ..................... 1506509

(51) Int. Cl.
C12N 15/11 (2006.01)
C12N 9/22 (2006.01)

(52) U.S. Cl.
CPC ............. *C12N 9/22* (2013.01); *C12N 15/11* (2013.01); *C07K 2319/09* (2013.01); *C12N 2310/20* (2017.05)

(58) Field of Classification Search
CPC ...... C12N 9/22; C12N 15/11; C12N 2310/20; C07K 2319/09
See application file for complete search history.

(56) References Cited

U.S. PATENT DOCUMENTS

| | | | |
|---|---|---|---|
| 8,361,725 B2 | 1/2013 | Russell et al. | |
| 8,697,359 B1 | 4/2014 | Zhang | |
| 8,889,356 B2 | 11/2014 | Zhang | |
| 9,790,490 B2 | 10/2017 | Zhang et al. | |
| 10,253,365 B1 | 4/2019 | Doudna et al. | |
| 10,648,020 B2 | 5/2020 | Zhang et al. | |
| 10,669,540 B2 | 6/2020 | Zhang et al. | |
| 11,091,798 B2 | 8/2021 | Zhang et al. | |
| 11,286,478 B2 | 3/2022 | Zhang et al. | |
| 2006/0035909 A1 | 2/2006 | Fuksova et al. | |
| 2009/0291131 A1 | 11/2009 | Maclachlan et al. | |
| 2014/0242699 A1 | 8/2014 | Zhang | |
| 2014/0356956 A1 | 12/2014 | Church et al. | |
| 2015/0079681 A1 | 3/2015 | Zhang | |
| 2017/0233756 A1 | 8/2017 | Begemann et al. | |
| 2019/0218602 A1 | 7/2019 | Zhang et al. | |
| 2019/0233814 A1 | 8/2019 | Zhang et al. | |
| 2019/0256900 A1 | 8/2019 | Zhang et al. | |
| 2020/0080112 A1 | 3/2020 | Zhang et al. | |
| 2020/0181623 A1 | 6/2020 | Zhang | |
| 2020/0283755 A1 | 9/2020 | Zhang et al. | |
| 2020/0318172 A1 | 10/2020 | Zhang et al. | |
| 2020/0318173 A1 | 10/2020 | Zhang et al. | |
| 2021/0040546 A1 | 2/2021 | Zhang et al. | |
| 2021/0076366 A1 | 3/2021 | Jang et al. | |

FOREIGN PATENT DOCUMENTS

| | | |
|---|---|---|
| CN | 103261213 A | 8/2013 |
| CN | 104017821 A | 9/2014 |
| CN | 105602993 A | 5/2016 |
| CN | 106536729 A | 3/2017 |
| GB | 3 009 511 | 4/2016 |
| GB | 1506509.7 | 4/2016 |
| RU | 2501850 C2 | 4/2009 |
| WO | WO-2014/093622 A2 | 6/2014 |
| WO | WO-2014/093712 A1 | 6/2014 |
| WO | WO-2014/118272 A1 | 8/2014 |
| WO | WO-2014/191521 A2 | 12/2014 |
| WO | WO-2014/197568 A2 | 12/2014 |
| WO | WO-2014/197748 A2 | 12/2014 |
| WO | WO-2014/204723 A1 | 12/2014 |
| WO | WO-2014/204724 A1 | 12/2014 |
| WO | WO-201 5/035139 A2 | 3/2015 |
| WO | WO-2015/089364 | 6/2015 |
| WO | WO-2015/089419 | 6/2015 |
| WO | WO-2015/089473 A1 | 6/2015 |
| WO | WO-2015/089486 A2 | 6/2015 |
| WO | WO-2016/049258 A2 | 3/2016 |

(Continued)

OTHER PUBLICATIONS

Wang et al., ChemBioChem 20:634-643, 2019.*
Charpentier et al., "Rewriting a genome", Nature, Mar. 2013, vol. 495, 2 pages.
Dahlman et al., "Orthogonal gene knockout and activation with a catalytically active Cas9 nuclease", Nature Biotechnology, vol. 33, No. 11, Oct. 5, 2015, pp. 1159-1161, XP055381172, US.
Database UniProt [Online] Nov. 30, 2010, SubName: Full =Uncharacterized protein {EC0:0000313:EMBL:EFL46285.1}; XP002769441, retrieved from EBI accession No. UNIPROT:E1KQG5, Database accession No. E1KQG5.

(Continued)

*Primary Examiner* — Delia M Ramirez
(74) *Attorney, Agent, or Firm* — Foley & Lardner LLP

(57) ABSTRACT

The invention relates to the field of genetic engineering tools, methods and techniques for gene or genome editing. Specifically, the invention concerns isolated polypeptides having nuclease activity, host cells and expression vectors comprising nucleic acids encoding said polypeptides as well as methods of cleaving and editing target nucleic acids in a sequence-specific manner. The polypeptides, nucleic acids, expression vectors, host cells and methods of the present invention have application in many fields of biotechnology, including, for example, synthetic biology and gene therapy.

7 Claims, 5 Drawing Sheets

Figure 1:
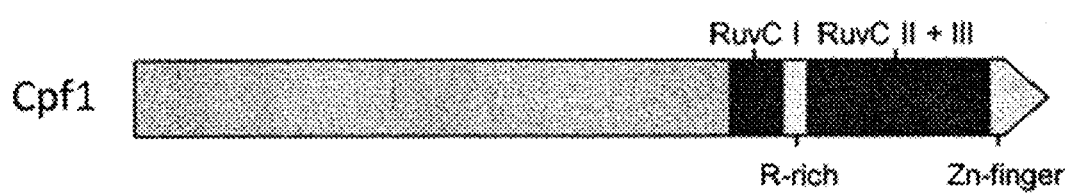

Specification includes a Sequence Listing.

(56) References Cited

FOREIGN PATENT DOCUMENTS

| WO | WO-2016/094872 A1 | 6/2016 |
|---|---|---|
| WO | WO-2016/166340 A1 | 10/2016 |
| WO | WO-2016/201155 A1 | 12/2016 |
| WO | WO-2016/205711 | 12/2016 |
| WO | WO-2016/205749 | 12/2016 |
| WO | WO-2016/205764 | 12/2016 |
| WO | WO-2017/064546 A1 | 4/2017 |
| WO | WO-2017/106657 | 6/2017 |
| WO | WO-2017/127807 A1 | 7/2017 |

OTHER PUBLICATIONS

Dickey etal, "Moraxella bovoculi hypothetical protein", Database ENA [Online] EMBL-EBI, Dec. 16, 2015, Database accession No. AKG14689, XP002772302, 3 pages.

Dickey et al., "Moraxella bovoculi hypothetical protein", Database ENA [Online] EMBL-EBI, May 5, 2015, Database accession No. AKG12737, XP002772309, 2 pages.

Dong, et al. "The crystal structure of Cpf1 in complex with CRISPR RNA," Nature, vol. 532, pp. 523-525, including Research Letter, dated 2016.

Exhibit 1001—U.S. Pat. No. 9,790,490—*Benson Hill Biosystems, Inc., Petitioner, v. The Broad Institute Inc., Presidents and Fellows of Harvard College & Massachusetts Institute of Technology*, Patent Owners, U.S. Pat. No. 9,790,490, Petition for Post Grant Review, filed Jul. 17, 2018.

Exhibit 1002—Prosecution History of the '490 patent—*Benson Hill Biosystems, Inc., Petitioner, v. The Broad Institute Inc., Presidents and Fellows of Harvard College & Massachusetts Institute of Technology*, Patent Owners, U.S. Pat. No. 9,790,490, Petition for Post Grant Review, filed Jul. 17, 2018.

Exhibit 1003—Declaration of Dr. Chase L. Beisel and accompanying Appendices A-C—*Benson Hill Biosystems, Inc., Petitioner, v. The Broad Institute Inc., Presidents and Fellows of Harvard College & Massachusetts Institute of Technology*, Patent Owners, U.S. Pat. No. 9,790,490, Petition for Post Grant Review, filed Jul. 17, 2018.

Exhibit 1004—Schunder et al., "First indication for a functional CRISPR/Cas system in Francisella tularensis," International Journal of Medical Microbiology, 303:51-60 (2013)—*Benson Hill Biosystems, Inc., Petitioner, v. The Broad Institute Inc., Presidents and Fellows of Harvard Colleg& Massachusetts Institute of Technology*, Patent Owners, U.S. Pat. No. 9,790,490, Petition for Post Grant Review, filed Jul. 17, 2018.

Exhibit 1005—Zetsche et al., "Cpf1 Is a Sinblge RNA-Guided Endonuclease of a Class 2 CRISPR-Cas System," Cell, 163:759-71 (2015)—*Benson Hill Biosystems, Inc., Petitioner, v. The Broad Institute Inc., Presidents and Fellows of Harvard College & Massachusetts Institute of Technology*, Patent Owners, U.S. Pat. No. 9,790,490, Petition for Post Grant Review, filed Jul. 17, 2018.

Exhibit 1006—Zetsche et al., "A Survey of Genome Editing Activity for 16 Cpf1 orthologs," bioRxiv, doi: https://doi.org/10.1101/134015 (2017)—*Benson Hill Biosystems, Inc., Petitioner, v. The Broad Institute Inc., Presidents and Fellows of Harvard College & Massachusetts Institute of Technology*, Patent Owners, U.S. Pat. No. 9,790,490, Petition for Post Grant Review, filed Jul. 17, 2018.

Exhibit 1007—Hsu et al., "Development and Applications of CRISPR-Cas9 for Genome Engineering," Cell, 157:1262-78 (2014)—*Benson Hill Biosystems, Inc., Petitioner, v. The Broad Institute Inc., Presidents and Fellows of Harvard College & Massachusetts Institute of Technology*, Patent Owners, U.S. Pat. No. 9,790,490, Petition for Post Grant Review, filed Jul. 17, 2018.

Exhibit 1008—Shmakov et al., "Discovery and Functional Characterization of Diverse Class 2 CRISPR-Cas Systems," Molecular Cell, 60:385-97 (2015)—*Benson Hill Biosystems, Inc., Petitioner, v. The Broad Institute Inc., Presidents and Fellows of Harvard College & Massachusetts Institute of Technology*, Patent Owners, U.S. Pat. No. 9,790,490, Petition for Post Grant Review, filed Jul. 17, 2018.

Exhibit 1009—Koonin et al., "Diversity, classification and evolution of CRISPR-Cas systems," Current Opinion in Microbiology, 37:67-78 (2017)—*Benson Hill Biosystems, Inc., Petitioner, v. The Broad Institute Inc., Presidents and Fellows of Harvard College & Massachusetts Institute of Technology*, Patent Owners, U.S. Pat. No. 9,790,490, Petition for Post Grant Review, filed Jul. 17, 2018.

Exhibit 1010—Karvelis et al., "Rapid characterization of CRISPR-Cas9 protospacer adjacent motif sequence elements," Genome Biology, 16:253, 1-13 (2015)—*Benson Hill Biosystems, Inc., Petitioner, v. The Broad Institute Inc., Presidents and Fellows of Harvard College & Massachusetts Institute of Technology*, Patent Owners, U.S. Pat. No. 9,790,490, Petition for Post Grant Review, filed Jul. 17, 2018.

Exhibit 1011—Lowder et al., "Rapid Evolution of Manifold CRISPR Systems for Plant Genome Editing," Frontiers in Plant Science, 7(1683):1-12 (2016)—*Benson Hill Biosystems, Inc., Petitioner, v. The Broad Institute Inc., Presidents and Fellows of Harvard College & Massachusetts Institute of Technology*, Patent Owners, U.S. Pat. No. 9,790,490, Petition for Post Grant Review, filed Jul. 17, 2018.

Exhibit 1012—Leenay et al., "Identifying and visualizing functional PAM diversity across CRISPR-Cas systems," Mol Cell, 62(1):137-47 (2016)—*Benson Hill Biosystems, Inc., Petitioner, v. The Broad Institute Inc., Presidents and Fellows of Harvard College & Massachusetts Institute of Technology*, Patent Owners, U.S. Pat. No. 9,790,490, Petition for Post Grant Review, filed Jul. 17, 2018.

Exhibit 1013—Makarova & Koonin, "Annotation and Classification of CRISPRCas Systems," Chapter 4 in CRISPR: Methods and Protocols, Methods in Molecular Biology, 1311:47-75 (2015)—*Benson Hill Biosystems, Inc., Petitioner, v. The Broad Institute Inc., Presidents and Fellows of Harvard College & Massachusetts Institute of Technology*, Patent Owners, U.S. Pat. No. 9,790,490, Petition for Post Grant Review, filed Jul. 17, 2018.

Exhibit 1014—HMM Summary Page: TIGR04330 (http://tigrfams.jcvi.org/cgibin/HmmReportPage.cgi?acc=TIGR04330) last visited Jun. 27, 2018—*Benson Hill Biosystems, Inc., Petitioner, v. The Broad Institute Inc., Presidents and Fellows of Harvard College & Massachusetts Institute of Technology*, Patent Owners, U.S. Pat. No.9,790,490, Petition for Post Grant Review, filed Jul. 17, 2018.

Exhibit 1015—Begemann et al., "Characterization and Validation of a Novel Group of Type V, Class 2 Nucleases for in vivo Genome Editing," bioRxiv, doi: http://dx.doi.org/10.1101/192799 (2017)—*Benson Hill Biosystems, Inc., Petitioner, v. The Broad Institute Inc., Presidents and Fellows of Harvard College & Massachusetts Institute of Technology*, Patent Owners, U.S. Pat. No. 9,790,490, Petition for Post Grant Review, filed Jul. 17, 2018.

Exhibit 1016—Ran et al., "In vivo genome editing using *Staphylococcus aureus* Cas 9," Nature, 520(7546):186-91 (2015)—*Benson Hill Biosystems, Inc., Petitioner, v. The Broad Institute Inc., Presidents and Fellows of Harvard College & Massachusetts Institute of Technology*, Patent Owners, U.S. Pat. No. 9,790,490, Petition for Post Grant Review, filed Jul. 17, 2018.

Exhibit 1017—Kleinstiver et al., "Engineered CRISPR-Cas9 nucleases with altered PAM specificities," Nature, 523(7561):481-85 (2015)—*Benson Hill Biosystems, Inc., Petitioner, v. The Broad Institute Inc., Presidents and Fellows of Harvard College & Massachusetts Institute of Technology*, Patent Owners, U.S. Pat. No. 9,790,490, Petition for Post Grant Review, filed Jul. 17, 2018.

Exhibit 1018—Gao et al., "Engineered Cpf1 variants with altered PAM specificities increase genome targeting range," Nature Biotechnology, 35(8):789-92 (2017)—*Benson Hill Biosystems, Inc., Petitioner, v. The Broad Institute Inc., Presidents and Fellows of Harvard College & Massachusetts Institute of Technology*, Patent Owners, U.S. Pat. No. 9,790,490, Petition for Post Grant Review, filed Jul. 17, 2018.

Exhibit 1019—Stella et al., "Structure of the Cpf1 endonuclease R-loop complex after target DNA cleavage," Nature, 546(7659):559-63 (2017)—*Benson Hill Biosystems, Inc., Petitioner, v. The Broad Institute Inc., Presidents and Fellows of Harvard College & Massachusetts Institute of Technology*, Patent Owners, U.S. Pat. No. 9,790,490, Petition for Post Grant Review, filed Jul. 17, 2018.

Exhibit 1020—Hirano et al., "Structure and Engineering of Francisella novicida Cas9," Cell, 164(5):950-61 (2016)—*Benson Hill Biosystems, Inc., Petitioner, v. The Broad Institute Inc., Presidents and Fellows*

(56) References Cited

OTHER PUBLICATIONS of Harvard College & Massachusetts Institute of Technology, Patent Owners, U.S. Pat. No. 9,790,490, Petition for Post Grant Review, filed Jul. 17, 2018.
Exhibit 1021—Fieck et al., "Modifications of the *E. coli* Lac repressor for expression in eukaryotic cells: effects of nuclear signal sequences on protein activity and nuclear accumulation," Nucleic Acids Research, 20(7):1785-91 (1992)—*Benson Hill Biosystems, Inc.*, Petitioner, v. *The Broad Institute Inc., Presidents and Fellows of Harvard College & Massachusetts Institute of Technology*, Patent Owners, U.S. Pat. No. 9,790,490, Petition for Post Grant Review, filed Jul. 17, 2018.
Exhibit 1022—U.S. Pat. No. 8,697,359—*Benson Hill Biosystems, Inc.*, Petitioner, v. *The Broad Institute Inc., Presidents and Fellows of Harvard College & Massachusetts Institute of Technology*, Patent Owners, U.S. Appl. No. 9,790,490, Petition for Post Grant Review, filed Jul. 17, 2018.
Exhibit 1023—Chiu et al., "Engineered GFP as a vital reporter in plants," Current Biology, 6(3):325-30 (1996)—*Benson Hill Biosystems, Inc.*, Petitioner, v. *The Broad Institute Inc., Presidents and Fellows of Harvard College & Massachusetts Institute of Technology*, Patent Owners, U.S. Pat. No. 9,790,490, Petition for Post Grant Review, filed Jul. 17, 2018.
Exhibit 1024—Mali et al., "RNA-Guided Human Genome Engineering via Cas9," Science, 339(6121):823-26 (2013)—*Benson Hill Biosystems, Inc.*, Petitioner, v. *The Broad Institute Inc., Presidents and Fellows of Harvard College & Massachusetts Institute of Technology*, Patent Owners, U.S. Pat. No. 9,790,490, Petition for Post Grant Review, filed Jul. 17, 2018.
Exhibit 1025—Sandy et al., "Mammalian RNAi: a practical guide," BioTechniques, 39:215-24 (2005)—*Benson Hill Biosystems, Inc.*, Petitioner, v. *The Broad Institute Inc., Presidents and Fellows of Harvard College & Massachusetts Institute of Technology*, Patent Owners, U.S. Pat. No. 9,790,490, Petition for Post Grant Review, filed Jul. 17, 2018.
Exhibit 1026—United States Patent Application Publication No. 2013/0302401—*Benson Hill Biosystems, Inc.*, Petitioner, v. *The Broad Institute Inc., Presidents and Fellows of Harvard College & Massachusetts Institute of Technology*, Patent Owners, U.S. Pat. No. 9,790,490, Petition for Post Grant Review, filed Jul. 17, 2018.
Exhibit 1027—International Publication No. WO 2014/118272—*Benson Hill Biosystems, Inc.*, Petitioner, v. *The Broad Institute Inc., Presidents and Fellows of Harvard College & Massachusetts Institute of Technology*, Patent Owners, U.S. Pat. No. 9,790,490, Petition for Post Grant Review, filed Jul. 17, 2018.
Exhibit 1028—Nair et al., "Multivalent N-Acetylgalactosamine-Conjugated siRNA Localizes in Hepatocytes and Elicits Robust RNAi-Mediated Gene Silencing," JACS, 136:16958-63 (2014)—*Benson Hill Biosystems, Inc.*, Petitioner, v. *The Broad Institute Inc., Presidents and Fellows of Harvard College & Massachusetts Institute of Technology*, Patent Owners, U.S. Pat. No. 9,790,490, Petition for Post Grant Review, filed Jul. 17, 2018.
Exhibit 1029—Ludlum et al., "Alkylation of Synthetic Polynucleotides," Science, 145(3630):397-99 (1964)—*Benson Hill Biosystems, Inc.*, Petitioner, v. *The Broad Institute Inc., Presidents and Fellows of Harvard College & Massachusetts Institute of Technology*, Patent Owners, U.S. Pat. No. 9,790,490, Petition for Post Grant Review, filed Jul. 17, 2018.
Exhibit 1030—Glen Research, The Glen Report, 19(1):1-16 (2007)—*Benson Hill Biosystems, Inc.*, Petitioner, v. *The Broad Institute Inc., Presidents and Fellows of Harvard College & Massachusetts Institute of Technology*, Patent Owners, U.S. Pat. No. 9,790,490, Petition for Post Grant Review, filed Jul. 17, 2018.
Exhibit 1031—El-Andaloussi et al., "Exosome-mediated delivery of siRNA in vitro and in vivo," Nat Protoc, 7(12):2112-26 (2012)—*Benson Hill Biosystems, Inc.*, Petitioner, v. *The Broad Institute Inc., Presidents and Fellows of Harvard College & Massachusetts Institute of Technology*, Patent Owners, U.S. Pat. No. 9,790,490, Petition for Post Grant Review, filed Jul. 17, 2018.
Exhibit 1032—Choulika et al., "Transfer of single gene-containing long terminal repeats into the genome of mammalian cells by a retroviral vector carrying the ere gene and the IoxP site," J Virol., 70(3):1792-98 (1996)—*Benson Hill Biosystems, Inc.*, Petitioner, v. *The Broad Institute Inc., Presidents and Fellows of Harvard College & Massachusetts Institute of Technology*, Patent Owners, U.S. Pat. No. 9,790,490, Petition for Post Grant Review, filed Jul. 17, 2018.
Exhibit 1033—Bergemann et al., "Excision of specific DNA-sequences from integrated retroviral vectors via site-specific recombination," Nucleic Acids Research, 23(21):4451-56 (1995)—*Benson Hill Biosystems, Inc.*, Petitioner, v. *The Broad Institute Inc., Presidents and Fellows of Harvard College & Massachusetts Institute of Technology*, Patent Owners, U.S. Pat. No. 9,790,490, Petition for Post Grant Review, filed Jul. 17, 2018.
Exhibit 1034—Dahlman et al., "In vivo endothelial siRNA delivery using polymeric nanoparticles with low molecular weight," Nat Nanotechnol., 9(8):648-55 (2014)—*Benson Hill Biosystems, Inc.*, Petitioner, v. *The Broad Institute Inc., Presidents and Fellows of Harvard College & Massachusetts Institute of Technology*, Patent Owners, U.S. Pat. No. 9,790,490, Petition for Post Grant Review, filed Jul. 17, 2018.
Exhibit 1035—Senis et al., "CRISPR/Cas9-mediated genome engineering: an adeno-associated viral (AAV) vector toolbox," Biotechnol J., 9(11):1402-12 (2014)—*Benson Hill Biosystems, Inc.*, Petitioner, v. *The Broad Institute Inc., Presidents and Fellows of Harvard College & Massachusetts Institute of Technology*, Patent Owners, U.S. Pat. No. 9,790,490, Petition for Post Grant Review, filed Jul. 17, 2018.
Exhibit 1036—Shukla et al., "Precise genome modification in the crop species *Zea mays* using zinc-finger nucleases," Nature, 459(7245):437-41 (2009)—*Benson Hill Biosystems, Inc.*, Petitioner, v. *The Broad Institute Inc., Presidents and Fellows of Harvard College & Massachusetts Institute of Technology*, Patent Owners, U.S. Pat. No. 9,790,490, Petition for Post Grant Review, filed Jul. 17, 2018.
Exhibit 1037—Jinek et al., "A programmable dual-RNA-guided DNA endonuclease in adaptive bacterial immunity," Science, 337(6069):816-21 (2012)—*Benson Hill Biosystems, Inc.*, Petitioner, v. *The Broad Institute Inc., Presidents and Fellows of Harvard College & Massachusetts Institute of Technology*, Patent Owners, U.S. Pat. No. 9,790,490, Petition for Post Grant Review, filed Jul. 17, 2018.
Exhibit 1038—Mojica et al., "Biological significance of a family of regularly spaced repeats in the genomes of Archaea, Bacteria and mitochondria," Mol Microbiol, 36(1):244-46 (2000)—*Benson Hill Biosystems, Inc.*, Petitioner, v. *The Broad Institute Inc., Presidents and Fellows of Harvard College & Massachusetts Institute of Technology*, Patent Owners, U.S. Pat. No. 9,790,490, Petition for Post Grant Review, filed Jul. 17, 2018.
Exhibit 1039—Ishino et al., "Nucleotide Sequence of the lap Gene, ResponsIble for Alkaline Phosphatase Isozyme Conversion in *Escherichia coli*, and Identification of the Gene Product," Journal of Bacteriology, 169(12):5429-33 (1987)—*Benson Hill Biosystems, Inc.*, Petitioner, v. *The Broad Institute Inc., Presidents and Fellows of Harvard College & Massachusetts Institute of Technology*, Patent Owners, U.S. Pat. No. 9,790,490, Petition for Post Grant Review, filed Jul. 17, 2018.
Exhibit 1040—Jansen et al., "Identification of genes that are associated with DNA repeats in prokaryotes," Molecular Microbiology, 43(6):1565-75 (2002)—*Benson Hill Biosystems, Inc.*, Petitioner, v. *The Broad Institute Inc., Presidents and Fellows of Harvard College & Massachusetts Institute of Technology*, Patent Owners, U.S. Pat. No. 9,790,490, Petition for Post Grant Review, filed Jul. 17, 2018.
Exhibit 1041—Bolotin et al., "Clustered regularly interspaced short palindrome repeats (CRISPRs) have spacers of extrachromosomal origin," Microbiology, 151 (Pt 8):2551-61 (2005)—*Benson Hill Biosystems, Inc.*, Petitioner, v. *The Broad Institute Inc., Presidents and Fellows of Harvard College & Massachusetts Institute of Technology*, Patent Owners, U.S. Pat. No. 9,790,490, Petition for Post Grant Review, filed Jul. 17, 2018.
Exhibit 1042—Mojica et al., "Intervening sequences of regularly spaced prokaryotic repeats derive from foreign genetic elements," J Mol Evol, 60(2):174-82 (2005)—*Benson Hill Biosystems, Inc.*,

(56) References Cited

OTHER PUBLICATIONS

Petitioner, v. *The Broad Institute Inc., Presidents and Fellows of Harvard College & Massachusetts Institute of Technology*, Patent Owners, U.S. Pat. No. 9,790,490, Petition for Post Grant Review, filed Jul. 17, 2018.
Exhibit 1043—Pourcel, "CRISPR elements in Yersinia pestis acquire new repeats by preferential uptake of bacteriophage DNA, and provide additional tools for evolutionary studies," Microbiology, 151(Pt3):653-3 (2005)—*Benson Hill Biosystems, Inc.*, Petitioner, v. *The Broad Institute Inc., Presidents and Fellows of Harvard College & Massachusetts Institute of Technology*, Patent Owners, U.S. Pat. No. 9,790,490, Petition for Post Grant Review, filed Jul. 17, 2018.
Exhibit 1044—Barrangou et al., "CRISPR provides acquired resistance against viruses in prokaryotes," Science, 315(5819):1709-12 (2007)—*Benson Hill Biosystems, Inc.*, Petitioner, v. *The Broad Institute Inc., Presidents and Fellows of Harvard College & Massachusetts Institute of Technology*, Patent Owners, U.S. Pat. No. 9,790,490, Petition for Post Grant Review, filed Jul. 17, 2018.
Exhibit 1045—Haft et al., "A Guild of 45 CRISPR-Associated (Cas) Protein Families and Multiple CRISPR/Cas Subtypes Exist in Prokaryotic Genomes," PLOS Computational Biology, 1(6):474-83 (2005)—*Benson Hill Biosystems, Inc.*, Petitioner, v. *The Broad Institute Inc., Presidents and Fellows of Harvard College & Massachusetts Institute of Technology*, Patent Owners, U.S. Pat. No. 9,790,490, Petition for Post Grant Review, filed Jul. 17, 2018.
Exhibit 1046—Brouns et al., "Small CRISPR RNAs Guide Antiviral Defense in Prokaryotes," Science, 321(5891):960-64 (2008)—*Benson Hill Biosystems, Inc.*, Petitioner, v. *The Broad Institute Inc., Presidents and Fellows of Harvard College & Massachusetts Institute of Technology*, Patent Owners, U.S. Pat. No. 9,790,490, Petition for Post Grant Review, filed Jul. 17, 2018.
Exhibit 1047—Garneau et al., "The CRISPR/Cas bacterial immune system cleaves bacteriophage and plasmid DNA," Nature, 468(7320):67-71 (2010)—*Benson Hill Biosystems, Inc.*, Petitioner, v. *The Broad Institute Inc., Presidents and Fellows of Harvard College & Massachusetts Institute of Technology*, Patent Owners, U.S. Pat. No. 9,790,490, Petition for Post Grant Review, filed Jul. 17, 2018.
Exhibit 1048—Deveau et al., "Phage Response to CRISPR-Encoded Resistance in Streptococcus thermophilus," Journal of Bacteriology, 190(4):1390-1400 (2008)—*Benson Hill Biosystems, Inc.*, Petitioner, v. *The Broad Institute Inc., Presidents and Fellows of Harvard College & Massachusetts Institute of Technology*, Patent Owners, U.S. Pat. No. 9,790,490, Petition for Post Grant Review, filed Jul. 17, 2018.
Exhibit 1049—Mojica et al., "Short motif sequences determine the targets of the prokaryotic CRISPR defence system," Microbiology, 155(Pt3):733-40 (2009)—*Benson Hill Biosystems, Inc.*, Petitioner, v. *The Broad Institute Inc., Presidents and Fellows of Harvard College & Massachusetts Institute of Technology*, Patent Owners, U.S. Pat. No. 9,790,490, Petition for Post Grant Review, filed Jul. 17, 2018.
Exhibit 1050—Anders et al., "Structural basis or PAM-dependent target DNA recognition by the Cas9 endonuclease," Nature, 215(7219):569-73 (2014)—*Benson Hill Biosystems, Inc.*, Petitioner, v. *The Broad Institute Inc., Presidents and Fellows of Harvard College & Massachusetts Institute of Technology*, Patent Owners, U.S. Pat. No. 9,790,490, Petition for Post Grant Review, filed Jul. 17, 2018.
Exhibit 1051—Nishimasu et al., "Crystal Structure of Cas9 in Complex with Guide RNA and Target RNA," Cell, 156(5):935-49 (2014)—*Benson Hill Biosystems, Inc.*, Petitioner, v. *The Broad Institute Inc., Presidents and Fellows of Harvard College & Massachusetts Institute of Technology*, Patent Owners, U.S. Pat. No. 9,790,490, Petition for Post Grant Review, filed Jul. 17, 2018.
Exhibit 1052—Deltcheva et al., "CRISPR RNA maturation by trans-encoded small RNA and host factor RNase III," Nature, 471 (7341):602-07 (2011)—*Benson Hill Biosystems, Inc.*, Petitioner, v. *The Broad Institute Inc., Presidents and Fellows of Harvard College & Massachusetts Institute of Technology*, Patent Owners, U.S. Pat. No. 9,790,490, Petition for Post Grant Review, filed Jul. 17, 2018.
Exhibit 1053—Makarova et al., "Unification of Cas protein families and a simple scenario for the origin and evolution of CRISPR-Cas systems," Biology Direct, 6:38, pp. 1-27 (2011)—*Benson Hill Biosystems, Inc.*, Petitioner, v. *The Broad Institute Inc., Presidents and Fellows of Harvard College & Massachusetts Institute of Technology*, Patent Owners, U.S. Pat. No. 9,790,490, Petition for Post Grant Review, filed Jul. 17, 2018.
Exhibit 1054—Nam et al., "Cas5d protein process pre-crRNA and assembles into a Cascade-like interference complex in Subtype I-C/Dvulg CRISPR-Cas system," Structure, 20(9):1574-84 (2012)—*Benson Hill Biosystems, Inc.*, Petitioner, v. *The Broad Institute Inc., Presidents and Fellows of Harvard College & Massachusetts Institute of Technology*, Patent Owners, U.S. Pat. No. 9,790,490, Petition for Post Grant Review, filed Jul. 17, 2018.
Exhibit 1055—Haurwitz et al., "Sequence- and structure-specific RNA processing by a CRISPR endonuclease," Science, 329(5997):1355-58 (2010)—*Benson Hill Biosystems, Inc.*, Petitioner, v. *The Broad Institute Inc., Presidents and Fellows of Harvard College & Massachusetts Institute of Technology*, Patent Owners, U.S. Pat. No. 9,790,490, Petition for Post Grant Review, filed Jul. 17, 2018.
Exhibit 1056—Hatoum-Aslan et al., "Mature clustered, regularly interspaced, short palindromic repeats RNA (crRNA) length is measured by a ruler mechanism anchored at the precursor processing site," PNAS, 108(52):21218-222 (2011)—*Benson Hill Biosystems, Inc.*, Petitioner, v. *The Broad Institute Inc., Presidents and Fellows of Harvard College & Massachusetts Institute of Technology*, Patent Owners, U.S. Pat. No. 9,790,490, Petition for Post Grant Review, filed Jul. 17, 2018.
Exhibit 1057—Rouillon et al., "Structure of the CRISPR Interference Complex CSM Reveals Key Similarities with Cascade," Molecular Cell, 52:124-34 (2013)—*Benson Hill Biosystems, Inc.*, Petitioner, v. *The Broad Institute Inc., Presidents and Fellows of Harvard College & Massachusetts Institute of Technology*, Patent Owners, U.S. Pat. No. 9,790,490, Petition for Post Grant Review, filed Jul. 17, 2018.
Exhibit 1058—Hale et al., "RNA-Guided RNA Cleavage by a CRISPR RNACas Protein," Cell, 139(5):945-56 (2009)—*Benson Hill Biosystems, Inc.*, Petitioner, v. *The Broad Institute Inc., Presidents and Fellows of Harvard College & Massachusetts Institute of Technology*, Patent Owners, U.S. Pat. No. 9,790,490, Petition for Post Grant Review, filed Jul. 17, 2018.
Exhibit 1059—Vestergaard et al., "CRISPR adaptive immune systems of Archaea," RNA Biology, 11(2):156-67 (2014)—*Benson Hill Biosystems, Inc.*, Petitioner, v. *The Broad Institute Inc., Presidents and Fellows of Harvard College & Massachusetts Institute of Technology*, Patent Owners, U.S. Pat. No. 9,790,490, Petition for Post Grant Review, filed Jul. 17, 2018.
Exhibit 1060—Voskarides & Deltas, "Screening for Mutations in Kidney-Related Genes Using SURVEYOR Nuclease for Cleavage at Heteroduplex Mismatches," Journal of Molecular Diagnostics, 11(4):311-18 (2009)—*Benson Hill Biosystems, Inc.*, Petitioner, v. *The Broad Institute Inc., Presidents and Fellows of Harvard College & Massachusetts Institute of Technology*, Patent Owners, U.S. Pat. No. 9,790,490, Petition for Post Grant Review, filed Jul. 17, 2018.
Exhibit 1061—Findlay et al., "A Digital PCR-Based Method for Efficient and Highly Specific Screening of Genome Edited Cells," PLoS One, 11(4):e0153901 (2016)—*Benson Hill Biosystems, Inc.*, Petitioner, v. *The Broad Institute Inc., Presidents and Fellows of Harvard College & Massachusetts Institute of Technology*, Patent Owners, U.S. Pat. No. 9,790,490, Petition for Post Grant Review, filed Jul. 17, 2018.
Exhibit 1062—Kim et al., "Genotyping with CRISPR-Cas-derived RNA-guided endonucleases," Nat Commun, 5:3157 (2014)—*Benson Hill Biosystems, Inc.*, Petitioner, v. *The Broad Institute Inc., Presidents and Fellows of Harvard College & Massachusetts Institute of Technology*, Patent Owners, U.S. Pat. No. 9,790,490, Petition for Post Grant Review, filed Jul. 17, 2018.
Exhibit 1063—Minton, "How can biochemical reactions within cells differ from those in test tubes?," Journal of Cell Science, 119:2863-69 (2006)—*Benson Hill Biosystems, Inc.*, Petitioner, v. *The Broad Institute Inc., Presidents and Fellows of Harvard College & Massachusetts Institute of Technology*, Patent Owners, U.S. Pat. No. 9,790,490, Petition for Post Grant Review, filed Jul. 17, 2018.

(56) References Cited

OTHER PUBLICATIONS

Exhibit 1064—Ellis, "Macromolecular crowding: obvious but underappreciated," Trends Biochem Sci, 26(10):597-604 (2001)—*Benson Hill Biosystems, Inc.*, Petitioner, v. *The Broad Institute Inc., Presidents and Fellows of Harvard College & Massachusetts Institute of Technology*, Patent Owners, U.S. Pat. No. 9,790,490, Petition for Post Grant Review, filed Jul. 17, 2018.
Exhibit 1065—Nishimasu et al., "Structural Basis for the Altered PAM Recognition by Engineered CRISPR-Cpf1," Mol Cell, 67(1):139-47 (2017)—*Benson Hill Biosystems, Inc.*, Petitioner, v. *The Broad Institute Inc., Presidents and Fellows of Harvard College & Massachusetts Institute of Technology*, Patent Owners, U.S. Pat. No. 9,790,490, Petition for Post Grant Review, filed Jul. 17, 2018.
Exhibit 1066—Shmakov et al., "Diversity and evolution of class 2 CRISPR-Cas systems," Nat Rev Microbiol., 15(3):169-82 (2017)—*Benson Hill Biosystems, Inc.*, Petitioner, v. *The Broad Institute Inc., Presidents and Fellows of Harvard College & Massachusetts Institute of Technology*, Patent Owners, U.S. Pat. No. 9,790,490, Petition for Post Grant Review, filed Jul. 17, 2018.
Exhibit 1067—Aravind et al., "Holliday junction resolvases and related nucleases: identification of new families, phyletic distribution and evolutionary trajectories," Nucleic Acids Research, 28(18):3417-32 (2000)—*Benson Hill Biosystems, Inc.*, Petitioner, v. *The Broad Institute Inc., Presidents and Fellows of Harvard College & Massachusetts Institute of Technology*, Patent Owners, U.S. Pat. No. 9,790,490, Petition for Post Grant Review, filed Jul. 17, 2018.
Exhibit 1068—Chen et al., "Structural asymmetry in the Thermus thermophilus RuvC dimer suggests a basis for sequential strand cleavages during Holiday junction resolution," Nucleic Acids Research, 41(1):648-59 (2013)—*Benson Hill Biosystems, Inc.*, Petitioner, v. *The Broad Institute Inc., Presidents and Fellows of Harvard College & Massachusetts Institute of Technology*, Patent Owners, U.S. Pat. No. 9,790,490, Petition for Post Grant Review, filed Jul. 17, 2018.
Exhibit 1069—Leenay & Beisel, "Deciphering, communicating, and engineering the CRISPR PAM," J Mol Biol., 429(2):177-91 (2017)—*Benson Hill Biosystems, Inc.*, Petitioner, v. *The Broad Institute Inc., Presidents and Fellows of Harvard College & Massachusetts Institute of Technology*, Patent Owners, U.S. Pat. No. 9,790,490, Petition for Post Grant Review, filed Jul. 17, 2018.
Exhibit 1070—Pul et al., "Identification and characterization of *E. coli* CRISPR-cas promoters and their silencing by H-NS," Mol Microbiol, 75(6):1495-512 (2010)—*Benson Hill Biosystems, Inc.*, Petitioner, v. *The Broad Institute Inc., Presidents and Fellows of Harvard College & Massachusetts Institute of Technology*, Patent Owners, U.S. Pat. No. 9,790,490, Petition for Post Grant Review, filed Jul. 17, 2018.
Exhibit 1071—Kim et al., "Highly efficient RNA-guided genome editing in human cells via delivery of purified Cas9 ribonucleoproteins," Genome Res., 24(6):1012-9 (2014)—*Benson Hill Biosystems, Inc.*, Petitioner, v. *The Broad Institute Inc., Presidents and Fellows of Harvard College & Massachusetts Institute of Technology*, Patent Owners, U.S. Pat. No. 9,790,490, Petition for Post Grant Review, filed Jul. 17, 2018.
Exhibit 1072—Transcript of Teleconference with the Board take Nov. 27, 2018—*Benson Hill Biosystems, Inc.*, Petitioner, v. *The Broad Institute Inc., Presidents and Fellows of Harvard College & Massachusetts Institute of Technology*, Patent Owners, U.S. Pat. No. 9,790,490, Petition for Post Grant Review, filed Dec. 4, 2018.
Exhibit 1073—Errata to Transcript of Teleconference with the Board, taken Nov. 27, 2018—*Benson Hill Biosystems, Inc.*, Petitioner, v. *The Broad Institute Inc., Presidents and Fellows of Harvard College & Massachusetts Institute of Technology*, Patent Owners, U.S. Pat. No. 9,790,490, Petition for Post Grant Review, filed Dec. 4, 2018.
Exhibit 2001—Ledford, "Five big mysteries about CRISPR's origins," Nature, 541, 7637, (2017) (last visited Oct. 5, 2018) https://www.nature.com/news/five-big-mysteries-about-crispr-sorigins-1.21294—*Benson Hill Biosystems, Inc.*, Petitioner, v. *The Broad Institute Inc., Presidents and Fellows of Harvard College & Massachusetts Institute of Technology*, Patent Owners, Case PGR2018-00072, U.S. Pat. No. 9,790,490, Patent Owners' Preliminary Response, filed Oct. 24, 2018.
Exhibit 2002—Sapranauskas et al., "The *Streptococcus thermophilus* CRISPR/Cas system provides immunity in *Escherichia coli*," Nucleic Acids Research, 39(21): 9275-9282, (2011)—*Benson Hill Biosystems, Inc.*, Petitioner, v. *The Broad Institute Inc., Presidents and Fellows of Harvard College & Massachusetts Institute of Technology*, Patent Owners, Case PGR2018-00072, U.S. Pat. No. 9,790,490, Patent Owners' Preliminary Response, filed Oct. 24, 2018.
Exhibit 2003—Gasiunas et al., "Cas9-crRNA ribonucleoprotein complex mediates specific DNA cleavage for adaptive immunity in bacteria," PNAS, 10.1073, (2012)—*Benson Hill Biosystems, Inc.*, Petitioner, v. *The Broad Institute Inc., Presidents and Fellows of Harvard College & Massachusetts Institute of Technology*, Patent Owners, Case PGR2018-00072, U.S. Pat. No. 9,790,490, Patent Owners' Preliminary Response, filed Oct. 24, 2018.
Exhibit 2004—Marraffini and Sontheimer, "CRISPR interference limits horizontal gene transfer in *Staphylococci* by targeting DNA," Science, 322(5909): 1843-1845, (2008) (Author Manuscript—supplementary material available on-line)—*Benson Hill Biosystems, Inc.*, Petitioner, v. *The Broad Institute Inc., Presidents and Fellows of Harvard College & Massachusetts Institute of Technology*, Patent Owners, Case PGR2018-00072, U.S. Pat. No. 9,790,490, Patent Owners' Preliminary Response, filed Oct. 24, 2018.
Exhibit 2005—Sinkunas et al., "In vitro reconstruction of cascade-mediated CRISPR immunity in *Streptococcus thermophilus*," The EMBO J, 32, 385-394 (2013) (Supplementary material available online)—*Benson Hill Biosystems, Inc.*, Petitioner, v. *The Broad Institute Inc., Presidents and Fellows of Harvard College & Massachusetts Institute of Technology*, Patent Owners, Case PGR2018-00072, U.S. Pat. No. 9,790,490, Patent Owners' Preliminary Response, filed Oct. 24, 2018.
Exhibit 2006—Jackson, et al., "Crystal structure of the CRISPR RNA-guided surveillance complex from *Escherichia coli\**," Science, 345(6203): 1473-1479 (2014) (Author Manuscript—supplementary material available on-line)—*Benson Hill Biosystems, Inc.*, Petitioner, v. *The Broad Institute Inc., Presidents and Fellows of Harvard College & Massachusetts Institute of Technology*, Patent Owners, Case PGR2018-00072, U.S. Pat. No. 9,790,490, Patent Owners' Preliminary Response, filed Oct. 24, 2018.
Exhibit 2007—Mulepati et al., "Crystal structure of a CRISPR RNA-guided surveillance complex bound to a ssDNA target," Science, 345(6203): 1479-1484, (2014) (Author Manuscript—supplementary material available on-line)—*Benson Hill Biosystems, Inc.*, Petitioner, v. *The Broad Institute Inc., Presidents and Fellows of Harvard College & Massachusetts Institute of Technology*, Patent Owners, Case PGR2018-00072, U.S. Pat. No. 9,790,490, Patent Owners' Preliminary Response, filed Oct. 24, 2018.
Exhibit 2008—Thabet et al., "Evolutionary trends of the transposase-encoding open reading frames A and B (orfA and orfB) of the mycobacterial IS6110 Insertion sequence," PLOS One, 10(6): 1-5, (2015) (Supplementary material available on-line)—*Benson Hill Biosystems, Inc.*, Petitioner, v. *The Broad Institute Inc., Presidents and Fellows of Harvard College & Massachusetts Institute of Technology*, Patent Owners, Case PGR2018-00072, U.S. Pat. No. 9,790,490, Patent Owners' Preliminary Response, filed Octo.
Exhibit 2009—Cong et al., "Multiple genome engineering using CRISPR/Cas system," Science, 339(6121): 819-823 (2013) (Author Manuscript—supplementary material available on-line)—*Benson Hill Biosystems, Inc.*, Petitioner, v. *The Broad Institute Inc., Presidents and Fellows of Harvard College & Massachusetts Institute of Technology*, Patent Owners, Case PGR2018-00072, U.S. Pat. No. 9,790,490, Patent Owners' Preliminary Response, filed Oct. 24, 2018.
Exhibit 2010—Mali et al., "Cas9 transcriptional activators for target specificity screening and paired nickases for cooperative genome engineering," Nat Biotechnol, 31 (9): 833-838, (2013) (Author Manuscript—supplementary material available on-line)—*Benson Hill Biosystems, Inc.*, Petitioner, v. *The Broad Institute Inc., Presidents and Fellows of Harvard College & Massachusetts Institute of Technology*, Patent Owners, Case PGR2018-00072, U.S. Pat. No. 9,790,490, Patent Owners' Preliminary Response, f.

(56) References Cited

OTHER PUBLICATIONS

Exhibit 2011—Pennisi, "The CRISPR craze," Science, 15-17, (2013)—*Benson Hill Biosystems, Inc., Petitioner, v. The Broad Institute Inc., Presidents and Fellows of Harvard College & Massachusetts Institute of Technology*, Patent Owners, Case PGR2018-00072, U.S. Pat. No. 9,790,490, Patent Owners' Preliminary Response, filed Oct. 24, 2018.

Exhibit 2012—Qi et al., "Repurposing CRISPR as an RNA-guided platform for sequence-specific control of gene expression," Cell 152, 1173-1183, (2013) (Supplementary material available on-line)—*Benson Hill Biosystems, Inc., Petitioner, v. The Broad Institute Inc., Presidents and Fellows of Harvard College & Massachusetts Institute of Technology*, Patent Owners, Case PGR2018-00072, U.S. Pat. No. 9,790,490, Patent Owners' Preliminary Response, filed Oct. 24, 2018.

Exhibit 2013—Gilbert et al., "CRISPR-Mediated modular RNA-guided regulation of transcription in Eukaryotes," Cell 154, 442-451, (2013) (Supplementary material available on-line)—*Benson Hill Biosystems, Inc., Petitioner, v. The Broad Institute Inc., Presidents and Fellows of Harvard College & Massachusetts Institute of Technology*, Patent Owners, Case PGR2018-00072, U.S. Pat. No. 9,790,490, Patent Owners' Preliminary Response, filed Oct. 24, 2018.

Exhibit 2014—Wu et al., "Target specificity of the CRISPR-Cas9 system," Quant Biol, 2(2): 59-70, (2014) (Author Manuscript—supplementary material available on-line)—*Benson Hill Biosystems, Inc., Petitioner, v. The Broad Institute Inc., Presidents and Fellows of Harvard College & Massachusetts Institute of Technology*, Patent Owners, Case PGR2018-00072, U.S. Pat. No. 9,790,490, Patent Owners' Preliminary Response, filed Oct. 24, 2018.

Exhibit 2015—Doudna et al., "The newfrontier of genome engineering with CRISPR-Cas9," Science, 346(6213), 1077-1086 (2014)—*Benson Hill Biosystems, Inc., Petitioner, v. The Broad Institute Inc., Presidents and Fellows of Harvard College & Massachusetts Institute of Technology*, Patent Owners, Case PGR2018-00072, U.S. Pat. No. 9,790,490, Patent Owners' Preliminary Response, filed Oct. 24, 2018.

Exhibit 2016—O'Geen et al., "How specific is CRISPR/Cas9 really?" Current Opinion in Chemical Biology, 29: 72-78-, (2015)—*Benson Hill Biosystems, Inc., Petitioner, v. The Broad Institute Inc., Presidents and Fellows of Harvard College & Massachusetts Institute of Technology*, Patent Owners, Case PGR2018-00072, U.S. Pat. No. 9,790,490, Patent Owners' Preliminary Response, filed Oct. 24, 2018.

Exhibit 2017—Chen et al., "Engineering human stem cell lines with inducible gene knockout using CRISPR/Cas9," Cell Stem Cell 17, 233-244 (2015) (Supplementary material available on-line)—*Benson Hill Biosystems, Inc., Petitioner, v. The Broad Institute Inc., Presidents and Fellows of Harvard College & Massachusetts Institute of Technology*, Patent Owners, Case PGR2018-00072, U.S. Pat. No. 9,790,490, Patent Owners' Preliminary Response, filed Oct. 24, 2018.

Exhibit 2018—Dow et al., "Inducible in vivo genome editing with CRISPR/Cas9," Nat Biotechnol, 33(4): 390-394, (2015) (Author Manuscript—supplementary material available on-line)—*Benson Hill Biosystems, Inc., Petitioner, v. The Broad Institute Inc., Presidents and Fellows of Harvard College & Massachusetts Institute of Technology*, Patent Owners, Case PGR2018-00072, U.S. Pat. No. 9,790,490, Patent Owners' Preliminary Response, filed Oct. 24, 2018.

Exhibit 2019—Didovyk et al., "Transcriptional regulation with CRISPR-Cas9: principles, advances and applications," Curr Opin Biotechnol, 40: 177-184, (2016) (Author Manuscript).

Exhibit 2020—Guilinger et al., "Fusion of catalytically inactive Cas9 to FokI nuclease improves the specificity of genome modification," Nat Biotechnol, 32(6): 577-582, (2014) (Author Manuscript—supplementary material available on-line)—*Benson Hill Biosystems, Inc., Petitioner, v. The Broad Institute Inc., Presidents and Fellows of Harvard College & Massachusetts Institute of Technology*, Patent Owners, Case PGR2018-00072, U.S. Pat. No. 9,790,490, Patent Owners' Preliminary Response, filed October.

Exhibit 2021—Horvath et al., "CRISPR/Cas, the immune system of bacteria and archaea," Science 327, 167-170, (2010)—*Benson Hill Biosystems, Inc., Petitioner, v. The Broad Institute Inc., Presidents and Fellows of Harvard College & Massachusetts Institute of Technology*, Patent Owners, Case PGR2018-00072, U.S. Pat. No. 9,790,490, Patent Owners' Preliminary Response, filed Oct. 24, 2018.

Exhibit 2022—Maggio et al., "Adenoviral vector delivery of RNA-guided CRISPR/Cas9 nuclease complexes induces targeted mutagenesis in a diverse array of human cells," Scientific Reports, 4: 5105, 1-11, (2014) (Supplementary material available on-line)—*Benson Hill Biosystems, Inc., Petitioner, v. The Broad Institute Inc., Presidents and Fellows of Harvard College & Massachusetts Institute of Technology*, Patent Owners, Case PGR2018-00072, U.S. Pat. No. 9,790,490, Patent Owners' Preliminary Response, f.

Exhibit 2023—Kwon et al., "Locus-specific histone deacetylation using a synthetic CRISPR-Cas9-based HDAC," NComms 15315, 1-8 (2017) (Supplementary material available on-line)—*Benson Hill Biosystems, Inc., Petitioner, v. The Broad Institute Inc., Presidents and Fellows of Harvard College & Massachusetts Institute of Technology*, Patent Owners, Case PGR2018-00072, U.S. Pat. No. 9,790,490, Patent Owners' Preliminary Response, filed Oct. 24, 2018.

Exhibit 2024—U.S. Patent Application Publication No. 20180148735 (published May 31, 2018) (Benson Hill Biosystems, Inc., applicant)—*Benson Hill Biosystems, Inc., Petitioner, v. The Broad Institute Inc., Presidents and Fellows of Harvard College & Massachusetts Institute of Technology*, Patent Owners, Case PGR2018-00072, U.S. Pat. No. 9,790,490, Patent Owners' Preliminary Response, filed Oct. 24, 2018.

Flatman, "Magnesium Transport across Cell Membranes", Journal of Membrane Biology, 80, 1984, pp. 1-14.

Gao, et al. "Engineered Cpf1 Enzymes with Altered PAM Specificities", BioRxiv Preprint, XP-002769442, 2016, doi:http://dx.doi.org/10.1101/091611, 1-13, including Figure Legends.

Gao, et al. "Engineered Cpf1 variants with altered PAM specificities", Nature Biotechnology, 2017, 1-4, doi:10.1038/nbt.3900, advanced online publication including Supplementary Information.

Guilinger et al., "Fusion of catalytically inactive Cas9 to FokI nuclease improves the specificity of genome modification", Nature Biotechnology, Jun. 2014, vol. 32, No. 6, pp. 577-581.

Haft, D.H., "HMM Summary Page: TIGR04330", 2012 XP-002757584, http://jcvi.org/cgi-bin/tigrfams/HmmReportPage.cgi?acc=TIGR04330.

Kleinstiver, et al. "Engineered CRISPR-Cas9 nucleases with altered PAM specificities," Nature, vol. 523, pp. 481-485, including Research Letter, dated 2015.

Leenay, et al. "Identifying and Visualizing Functional PAM Diversity across CRISPR-Cas Systems", Molecular Cell, 2016, 62:137-147.

Makarova, et al. "An updated evolutionary classification of CRISPR-Cas systems" Nature Reviews—Microbiology, 2015, 13:722-736.

Mali et al., "CAS9 transcriptional activators for target specificity screening and paired nickases for cooperative genome engineering", Nature Biotechnology, Sep. 2013, vol. 31, No. 9, pp. 833-837.

Naito et al., "CRISPRdirect: Software for designing CRISPR/Cas guide RNA with reduced off-target sites", Bioinformatics, 2015, vol. 31, No. 7, pp. 1120-1123.

Pattanayak et al., "High-throughput profiling of off-target DNA cleavage reveals RNA-programmed Cas9 nuclease specificity", Nature Biotechnology, Sep. 2013, vol. 31, No. 9, pp. 839-845.

Ran et al., "Double Nicking by RNA-guided CRISPR Cas9 for enhanced genome editing specificity", Cell, Sep. 2013, vol. 154, pp. 1380-1389.

Schunder et al., "First indication for a functional CRISPR/Cas system in Francisella tularensis", International Journal of Medical Microbiology, 2013, vol. 303, pp. 51-60.

Shmakov et al., "Discovery and Functional Characterization of Diverse Class 2 CRISPR-Cas Systems", Molecular Cell, vol. 60, No. 3, Oct. 22, 2015. pp. 385-397, XP055267512, US.

(56) References Cited

OTHER PUBLICATIONS

Takashi et al., "Crystal structure of Cpf1 in complex with guide RNA and target DNA", Cell, Apr. 2016, vol. 165, No. 4, pp. 949-962.
Type V CRISPR-associated protein Cpfi [*Acidaminococcus* sp. Bv3L6], 2017, NCBI Reference Sequence: WP_02173622.1, Non-redundant Protein Sequence.
Van Der Oost et al., "Unravelling the structural and mechanistic basis of CRISPR-Cas systems", Nature Reviews, Microbiology, Jul. 2014, vol. 12, pp. 479-492.
Van Der Oost, "New tool for genome surgery", Science, Feb. 2013, vol. 339, pp. 768-770.
Vestergaard et al., "CRISPR adaptive immune systems of Archaea", RNA Biology, 2014, vol. 11, No. 2, pp. 156-167.
Wiedenfeft et al, "Structural Basis for DNase Activity of a Conserved Protein Implicated in CRISPR-Mediated Genome Defense", Structure, 17, 2009, pp. 904-912.
Database UniProt [Online] "SubName: Full=CRISPR-associated protein CPf1, subtype PREFRAN {ECO:0000313 | EMBL: AJJ47668.1};", XP002760659, retrieved from EBI accession No. UNIPROT: A0A0B6KQP9, Database accession No. A0A0b6kqp9 sequence, Apr. 1, 2015.
Zetsche et al., "Cpf1 is a single RNA-guided endonuclease of a class 2 CRISPR-Cas system", Cell, Oct. 2015, vol. 163, No. 3, pp. 759-771.
International Search Report issued in International Patent Application No. PCT/EP2016/058442, dated Sep. 2, 2017.
3rd Party Citation D46 from EP Opposition Proceedings for EP Pat. No. 3009511—Barrangou, "Class 2 large effector protein architectures", PowerPoint Presentation Slide, Jun. 20, 2015, 1 page.
3rd Party Citation D47 from EP Opposition Proceedings for EP Pat. No. 3009511—CRIPSR Conference 2015, Website Print-out of Event Announcement, New York, New York, Jun. 18-20, 2015, accessed at https://web.archive.org/web/20150708120205/https://www.crispr2015.com/ on Jul. 30, 2019, 1 page.
3rd Party Citation D48 from EP Opposition Proceedings for EP Pat. No. 3009511—CRIPSR Conference 2015, Conference Program including Schedule of Events, New York, New York, Jun. 18-20, 2015, accessible at https://web.archive.org/web/20151109114832/http:/nebula.wsimg.com/f9aa9f29c2be9e03bc66d1da9e0f2634?AccessKeyId=377234A383373D636692&disposition=0&alloworigin=1, 8 pages.
3rd Party Citation D49 from EP Opposition Proceedings for EP Pat. No. 3009511—Barrangou, et al., "Class 2 large effector protein architectures", Caribou Biosciences Mail—New Systems with PowerPoint Presentation Slide, Jun. 20, 2015, 2 pages.
3rd Party Citation D50 from EP Opposition Proceedings for EP Pat. No. 3009511—Declaration of Prof. Dr. Rodolophe Barrangou with Appendices, Aug. 13, 2019, 33 pages.
3rd Party Citation D51 from EP Opposition Proceedings for EP Pat. No. 3009511—Declaration of Andrew P. May DPhil with Appendices, Aug. 9, 2019, 24 pages.
3rd Party Citation D52 from EP Opposition Proceedings for EP Pat. No. 3009511—Declaration of Rachel E. Haurwitz, PH.D. with Appendices, Aug. 13, 2019, 8 pages.
Amit et al., "Unbiased Reconstruction of a Mammalian Transcriptional Network Mediating Pathogen Responses", Science vol. 326, 2009, pp. 257-263.
Andreakos et al., "Distinct Pathways of LPS-INduced NF-kB Activation and Cytokine Production in Human Myeloid and Nonmyeloid Cells Defined by Selective Utilization of MyD88 and Mal/TIRAP", Blood, vol. 103, No. 6, 2004, pp. 2229-2237.
Assignment from Bernd Zetsche to The Broad Institute Inc. for U.S. Appl. No. 14/975,085 dated Jan. 5, 2016, 2 pages.
Assignment from Feng Zhang to The Broad Institute Inc. for U.S. Appl. No. 14/975,085 dated Dec. 23, 2015, 2 pages.
Assignment from Ian Slaymaker to The Broad Institute Inc. for U.S. Appl. No. 14/975,085 dated Jan. 6, 2016, 2 pages.
Assignments from Inventors, Ian Slaymaker, Omar O. Abudayyeh, Feng Zhang, Jonathan Gootenberg, and Bernd Zetsche to The Broad Institute Inc. or Presidents and Fellows of Harvard College for U.S. Appl. No. 14/975,085 (annex to Summons to attend oral proceedings), Jan. 30, 2017, 15 pages.
Chen et al., "Targeted activation of diverse CRISPR-Cas systems for mammalian genome editing via proximal CRISPR targeting", Nature Communications, vol. 8, Apr. 7, 2017, DOI: 10.1038/ncomms14958, pp. 1-12.
Cho, Seung Woo, et al., "Targeted genome engineering in human cells with the Cas9 RNA-guided endonuclease," Nature Biotechnology, vol. 31 pp. 230-232, including Supplementary Information, 14 pages.
Daligault et al., GenBank Accession No. AJJ47668, Feb. 9, 2015, 2 pages.
D'Astolfo et al., "Efficient Intracellular Delivery of Native Proteins", Cell, vol. 161, Apr. 23, 2015, http://dx.doi.org/10.1016/j.cell.2015.03.028, pp. 674-690.
Declaration of Steven R. Trybus in EPO opposition proceedings concerning European Patent No. 3 009 511 dated Sep. 14, 2018, 13 pages.
Expert Declaration of Dmitrij Frishman with Exhibits dated Aug. 12, 2019, 25 pages.
Fagerlund et al., "The Cpf1 CRISPR-Cas protein expands genome-editing tools", Genome Biology, vol. 16, No. 251, Nov. 7, 2015, DOI 10.1186/s13059-015-0824-9, pp. 1-3.
GEO Accession No. GSE2706 (Expression Profile Analysis for TANK, obtained from http://www.ncbi.nlm.nih.gov/geo/tools/profileGraph.cgi?ID=GDS1249:207616_s_at, Nov. 7, 2014, 2 pages.
Ghosh et al., "Toll-like Receptor (TLR) 2-9 Agonists-lnduced Cytokines and Chemokines: I. Comparison with T Cell Receptor-Induced Responses", Cellular Immunology, vol. 243, 2006, pp. 48-57.
Graham et al., "Resources for the design of CRISPR gene editing experiments", Genome Biology, vol. 16, No. 260, Nov. 27, 2015, DOI 10.1186/s13059-015-0823-x, pp. 1-21.
Hsu, et al., "DNA targeting specificity of RNA-guided Cas9 nucleases," Nature Biotechnology, vol. 31, 2013, pp. 827-834.
Hwang W., et al., "Efficient In Vivo Genome Editing Using RNA-Guided Nucleases," Nature Biotechnology, vol. 31, No. 3, Mar. 2013, pp. 227-229 (12 pages).
Jiang et al., "Demonstration of CRISPR/Cas9/sgRNA-mediated targeted gene modification in *Arabidopsis*. tobacco, sorghum and rice", Nucleic Acids Research, vol. 41, No. 20, e188, Sep. 2, 2013, pp. 1-12.
Kawagoe et al., "TANK is a Negative Regulator of Toll-Like Receptor Signaling and is Critical for the Prevention of Autoimmune Nephritis", Nature Immunology, vol. 10, No. 9, 2009, pp. 965-973.
Kim et al., "Genome-wide analysis reveals specificities of Cpf1 endonucleases in human cells", Nature Biotechnology, vol. 34, No. 8, Jun. 6, 2016 (corrected Jul. 18, 2016), pp. 863-888.
Krawczyk et al., "Toll-like Receptor-Induced Changes in Glycolytic Metabolism Regulate Dendritic Cell Activation", Blood, vol. 115, No. 23, 2010, pp. 4742-4749.
Liu et al., "C2c1-sgRNA Complex Structure Reveals RNA-Guided DNA Cleavage Mechanism", Molecular Cell, vol. 65, Jan. 19, 2017, pp. 310-322.
Liu et al., "Two Distant Catalytic Sites Are Responsible for C2c2 RNase Activities", Cell, vol. 168, Jan. 12, 2017, pp. 121-134.
Lund et al., "Toll-like Receptor 9-Mediated Recognition of Herpes Simplex Virus-2 by Plasmacytoid Dendritic Cells", J. Exp. Med., vol. 198, No. 3, Aug. 4, 2003, pp. 513-520.
Lundgren et al., Methods in Molecular Biology, vol. 1311, Chapters 1 and 4, 2015, pp. 1-21 and 47-75.
Mastroianni, et al., "Group II Intron-Based Gene Targeting Reactions in Eukaryotes" Plos One, vol. 3, 2008, pp. 1-15, 15 pages. Doi:10.1371/journal.pone.0003121.
Napolitani et al., "Selected Toll-like Receptor Agonist Combinations Synergistically Trigger a T Helper Type 1-Polarizing Program in Dendritic Cells", Nature Immunology, vol. 6, No. 8, 2005, pp. 769-776.
New England Biolabs, "NEBuffer 3 product information", Feb. 26, 2018, 3 pages.

(56) References Cited

OTHER PUBLICATIONS

Nishimasu et al., "Crystal Structure of Cas9 in Complex with Guide RNA and Target RNA," Cell, 156(5):935-49 (2014).
Nishimasu et al.,"Crystal Structure of *Staphylococcus aureus* Cas9", Cell, 2015, vol. 162, pp. 1113-1126, Supplemental Information.
Prakash et al., "Targeted delivery of antisense oligonucleotides to hepatocytes using triantennary N-acetyl galactosamine improves potency 10-fold in mice", Nucleic Acids Research, vol. 42, No. 13, Jul. 3, 2014, doi: 10.1093/nar/gku531, pp. 8796-8807.
Reindl et al., "Abstract: A Pan-Specific Inhibitor of the Polo-Box Domains of Polo-Like Kinases Arrests Cancer Cells in Mitosis", Chem Bio Chem, vol. 10, Apr. 6, 2009, pp. 1145-1148. Downloaded from http://onlinelibrary.wiley.com/doi/10.1002/cbic.2009000559/, abstract on Jan. 4, 2012.
Ruse et al., "New Players in TLR-Mediated Innate Immunity: P13K and Small Rho GTPases", Immunologic Research, vol. 34, 2006, pp. 33-48.
Sadowski et al., "The sequence-structure relationship and protein function prediction", Current Opinion in Structural Biology, vol. 19 pp. 2009, 357-362 (6 pages).
Sander, et al., "CRISPR-Cas systems for editing, regulating and targeting genomes," Nature Biotechnology, vol. 32, 2014, pp. 347-355, 9 pages.
ScienceDirect Excerpt—D'Astolfo et al., "Efficient Intracellular Delivery of Native Proteins", Cell, vol. 161, Issue 3, Apr. 23, 2015, pp. 674-690 (article provided separately—excerpt 1 page only).
Seffernick et al., "Melamine Deaminase and Atrazine Chlorohydrolase: 98 Percent Identical but Functionally Different", Journal Bacteriology, vol. 183, 2001, 2405-2410, (8 pages).
Sequence listing filed for EP Application No. 16150428.7.
Slaymaker et al.,"Rationally engineered Cas9 nucleases with improved specificity", Science, vol. 351, No. 6268, Jan. 1, 2016, pp. 84-88.
Strebhardt, "Multifaceted Polo-like Kinases: Drug Targets and Antitargets for Cancer Therapy", Nature Reviews, vol. 9, Aug. 2010, pp. 643-660.
Supporting Online Material (43 pages) for Amit et al., "Unbiased Reconstruction of a Mammalian Transcriptional Network Mediating Pathogen Responses", Science, vol. 326, 2009, pp. 257-263.
Tang et al., "Identification of Dehalobacter reductive dehalogenases that catalyse dichlorination of chloroform, 1,1,1-trichloroethane and 1,2-dichloroethane", Philosophical Transactions of the Royal Society B, vol. 368, 2013, pp. 1-10 (10 pages).
Termeer et al., "Oligosaccharides of Hyaluronan Activate Dendritic Cells via Toll-like Receptor 4", Journal of Experimental Medicine, vol. 195, No. 1, 2002, pp. 99-111.
Witkowski et al., "Conversation of a β-Ketoacyl Synthase to a Malonyl Decarboxylase by Replacement of the Active-Site Cysteine with Glutamine", Biochemistry, vol. 38, 1999, pp. 11643-11650.
Xie, et al. "RNA-Guided Genome Editing in Plants Using a CRISPR-Cas System" Molecular Plant, vol. 6, Nov. 2013, 1975-1983, 9 pages.
Xie, K, et al., "Boosting CRISPR/Cas9 multiplex editing capability with the endogenous tRNA-processing system", Proc. Natl. Acad. Sci. U.S.A., 2015, vol. 112. pp. 3570-3575.
Yang et al., "Making and Breaking Nucleic Acids: Two-Mg2-Ion Catalysis and Substrate Specificity", Molecular Cell, vol. 22, Apr. 7, 2006, pp. 5-13.
Yang et al., "PAM—Development Target DNA Recognition and Cleavage by C2c1 CRISPR-Cas Endonuclease", Cell, vol. 167, Dec. 15, 2016, pp. 1814-1828.
Wu et al., "Correction of a Genetic Disease in Mouse via Use of CRISPR-Cas9," Cell Stem Cell, Brief Report, vol. 13, Dec. 5, 2013, pp. 659-662.
Guo, et al., "Protein Tolerance to Random Amino Acid Change", The National Academy of Sciences, PNAS, Jun. 22, 2004, vol. 101, No. 25, pp. 9205-9210.
Third Party Observations filed in EP Appl. Ser. No. 19172057.2 dated Dec. 21, 2020 (14 pages).
Bikard et al., "Programmable repression and activation of bacterial gene expression using an engineered CRISPR-Cas system," Nucleic Acids Research, 2013, vol. 41, No. 15 (pp. 7429-7437).
Cai et al., "Targeted transgene integration in plant cells using designed zinc finger nucleases," Plant Molecular Biology, 2009, vol. 69 (pp. 699-709).
Gen Bank Accession No. A0Q7Q2.1, RecName: Full=CRISPR—associated endonuclease Cpf1; AltName: Full=FnCpf1, publicly available Dec. 2015, printed as pp. 1/2-2/2. (Year: 2015).
Gen Bank Accession No. U2UMQ6.1, Rec Name: Full=CRISPR-associated endonuclease Cpf1; AltName: Full=AsCpf1, publicly available Dec. 2015, printed as pp. 1/2-2/2. (Year: 2015).
Ledfrod, "Bacteria yield new gene cutter," Nature, Oct. 1, 2015, vol. 526 (p. 17).
Lee et al., "Site-specific integration in CHO cells mediated by CRISPR/Cas9 and homology-directed DNA repair pathway," Scientific Reports, Feb. 25, 2015, vol. 5 (pp. 1-11).
Leinonen et al., "The EMBL sequence version archive," Bioinformatics, 2003 vol. 19, No. 14 (pp. 1861-1862).
Qi et al., "Repurposing CRISPR as an RNA-Guided Platform for Sequence-Specific Control of Gene Expression," Cell, Feb. 28, 2013, vol. 152 (pp. 1173-1183).
Yamano et al., "Crystal Structure of Cpf1 in Complex with Guide RNA and Target DNA," Cell, vol. 165, May 5, 2016 (pp. 949-962).
Zhu et al., "A CRISPR/Cas-Mediated Selection-free Knockin Strategy in Human Embryonic Stem Cells," Stem Cell Reports, Jun. 9, 2015, vol. 4, (pp. 1103-1111).
U.S. Appl. No. 15/566,528, filed Oct. 13, 2017.
Konermann et al., "Genome-scale transcriptional activation by an engineered CRISPR-Cas9 complex," Nature, Jan. 29, 2015, vol. 517, pp. 583-588 (18 pages).
Gao, L., et al., Engineered Cpf1 enzymes with altered PAM specificities. bioRxiv preprint doi: https://doi.org/10.1101/091611, Dec. 4, 2016, pp. Jan. 1/14-14/14, pp. 1/3-3/3 of Figs, and pp. S1-S8.
Gen Bank Accession No. WP_051666128.1, publicly available Aug. 16, 2015, printed as p. 1/1.
Doudna et al., "The new frontier of genome engineering with CRISPR-Cas9," Science, Nov. 28, 2014, vol. 346 (pp. 1077-1087).
Rohmer et al., Gen Bank accession No. A0Q7Q2, Dec. 9, 2015 (3 pages).
Singh et al., "Protein Engineering Approaches in the Post-Genomic Era," Current Protein and Peptide Science, 2018, vol. 19, No. 1 (pp. 5-15).

* cited by examiner

A.

B.

Figure 3A

```
505317677 Methanomethylophilus alvus              ..................................................MDAKEPTGQYPLSKTRFELRPI.....GRTNDMLEA.......S.GYLAEDRHRAE..CY.PRAKELLDDMHRAPLNRVLPQI
545612232 Acidaminococcus sp BV3L6 8              ..................................................MTQEEGTNLYQVSKTRFELIPQ.....GKTLKHIQE.......Q.GFIEEDKARMD..HY.KELKPIIDRIYKTYADQCLQIV
851218172 Candidatus Methanoplasma termitum 10    ..................................................MNNYDEFTKLYPIQNTIRFELKFQ....GRTMEHLET.......F.NFPEEDRDRAE..KY.KILKEAIDEYHKKPIDEHLTRM
737666241 Lachnospiraceae                         ..................................................MSFLEKFTNCYSLSKTIRFKATRV....GRTQENIDN......K.RGVKKLLDRKYLSFINDVLHSI
(unreadable) 1                                    ..................................................MSIYQEFVNKYSLSKTLRFELIPQ....GKTLENIKA......DY.MKAKQIIDKYHQFFIEEILSSV 505317677 Methanomethylophilus alvus              ...................................QDADGYRGLFARPALDE.................AMRIAKEMGNESDIEV........................LEAF...NGF.SVFRTGY
545612232 Acidaminococcus sp BV3L6 8              ....GRTDNLTLDAINKRHAEIVRGLFNARLFNGK.................VLKQLGTVTTEHENAL............................................LRSF...DKF.TTYFSGF
851218172 Candidatus Methanoplasma termitum 10    ....K....DDR...FKDLFSKRLFSEL........................LKEETYRKGMHQEIDA.............................................LKSF...DKF.SGYFIGL
737666241 Lachnospiraceae bacterium ND2006 14    ....G....NEG...YKSLFKKDIIE..T.......................ILPEFLDDKDEIAL................................................VNSF...NGF.TTAFTGF
(unreadable) 1                                    ....D....SEK...FKNLFNQMLIDAKK.......................GGESDKILMEKQSKDNGIEFKANSDITDIDEALEI.........................IRSF...KGW.TTYFKGF 505317677 Methanomethylophilus alvus              HESRENIY.SDE.......DM.VSVAYRITEDNPPRFVSMALIPDKLNESHPD.......................I..ISEVSGNLGVDD.........................
545612232 Acidaminococcus sp BV3L6 8              YENEKNVF.SAE.......DISTAIPHRIVQDNFPKFKENCHIFTRLITAVPS.............................LREHFENVKKAIGIFVSTS................
851218172 Candidatus Methanoplasma termitum 10    BENRKNMY.SDG.......DRITAISNRIVNENFPNFLDNLQKYCEARKYPE.............................WLIKAESALVAHNIK...................
737666241 Lachnospiraceae bacterium ND2006 14    FDNRERMF.SEB.......AKSTSIAFRCINEMLTRYISNRMDIFSRV..DAIF.............................DKHEVQEIRKEKILNSDYD...............
(unreadable) 1                                    HENRKNVY.SSN.......DIPTSIIYRIVDDNLPKFLENKAKYESL.KDEAP............................EAINYEQIKKDLAEELTFDIDYKTSEVNQRVFS 505317677 Methanomethylophilus alvus              IGNYFDVSNYNNFLSQAGIDD......YMHIIGG...KTTEDGLIQAFNVVLN..LRHQKOP...........GFE....KI........QFKQLYKQLLSVRTSK
545612232 Acidaminococcus sp BV3L6 8              IEEVFSFPYNQLFTQTQIDL.......YNQLLGGIS.RKAGTEKIKGLNEVLN.LAIQKND............ET...A.HIIASLPHRFIPLFKQLLSDRNTL
851218172 Candidatus Methanoplasma termitum 10    NDEVFSLEYTMKVLNQEGIQR......YNLALGGIV.TKSGE.KWKGLNDALN.LRHQSEK............SSK...G.RI.......HNTFLFKQLLSEKEEF
737666241 Lachnospiraceae bacterium ND2006 14    VEDFFEGEPNFV.TQEGIDV.......YNAIIGGFV.TESGE.KIKGLNEYIN.LYNQRTK............Q.KL....PKFKFLYKQVLSDRESL
(unreadable) 1                                    LDEVFEIANFNNYLMCSGITK......FNTIIGGKF.VNGENTRKGINEYIN.LYSQQIN.............DNT..L.KK.......YKMSVLFKQLLSDTBSK 505317677 Methanomethylophilus alvus              SYIPKQFDNSKE.................MVDCICDY..VSKIERSETVER...............ALKIVRNI..........S..SFDLRGIFVNKK.NLR
545612232 Acidaminococcus sp BV3L6 8              SPILEEFKSDEE.................VIQSECKY..KILLRNERVLET................AEALFNEL.........N..SIDLTHIPISHK.KLE
851218172 Candidatus Methanoplasma termitum 10    SYIPDVFTEDSQ.................LLPSIGGF..FAQIEN..DRDG.............NIFDRALELISSY.......A..EYDERIYIRQA.DIN
737666241 Lachnospiraceae bacterium ND2006 14    SFYQEGYSDEE.................VLEVFRNT..LNKRMSEIFSSIK...............KLEKFKNF.........D..EYSSAGIFVRDGPAIS
(unreadable) 1                                    SFVIDKLEDDSD................VVTTMQSF..YEQIAAFKTVEE.................KSIKETLSLLFDDL..........KAQKLDSKIYFRNDKSLT 505317677 Methanomethylophilus alvus              ILSNKL.............IGDMDAIETALMHSSSSE..........................NDKKSVYDSAEAFTLDDIFSSVKKF....................
545612232 Acidaminococcus sp BV3L6 8              TISSAL.............CDHMFTLRNALIYERRISE.........................LTGKIFK.SAKEKVQRSLK.HEDINLQEITSAAG...........
851218172 Candidatus Methanoplasma termitum 10    PVSNVI.............FGEWGTLGGLMRSYKADS..........................INDRNLE.RTCKKVDKWLD.SKEFALSDVLEAIKFT.........
737666241 Lachnospiraceae bacterium ND2006 14    TISKDI.............FGEWNVIRDKWWNAEYDDI.........................HLKKKAVVTE.KYRODBRKSFFKIGSFSLEQIQBYADAD......GN
(unreadable) 1                                    DLSQQV.............FDDYSVIGTAVLEYITQQ..........................IAPKNLIDFPSK.HEQELIKKTEKAKYLSKETIKLALHEP.....NKHRDTIR
```

Figure 3B

Figure 3C

NUCLEASE-MEDIATED GENOME EDITING

CROSS-REFERENCE TO RELATED APPLICATIONS

This application is a Continuation of U.S. application Ser. No. 15/566,528, filed Oct. 13, 2017, which is the National Phase of International Patent Application No. PCT/EP2016/058442, filed Apr. 15, 2016, published on Oct. 20, 2016 as WO 2016/166340 A1, which claims priority to United Kingdom Patent Application No. 1506509.7, filed Apr. 16, 2015, U.S. Provisional Application No. 62/269,143, filed Dec. 18, 2015 and U.S. Provisional Application No. 62/312,724, filed Mar. 24, 2016. The contents of these applications are herein incorporated by reference in their entirety.

SEQUENCE LISTING

The instant application contains a Sequence Listing which has been submitted in ASCII format via EFS-WEB and is hereby incorporated by reference in its entirety. Said ASCII copy, created on Sep. 23, 2019, is named 114203-5773_SL.txt and is 73,301 bytes in size.

FIELD OF THE INVENTION

The invention relates to the field of genetic engineering tools, methods and techniques for genome or gene editing. Such editing or manipulation of polynucleotide sequences, including structural or control gene sequences has application in many fields of health and biotechnology, for example gene therapy treatments of humans or animals, plant and animal breeding, and improvement of industrial organisms, e.g. by altering enzymes and metabolic pathways, particularly microorganisms; also in the areas of synthetic biology and algal biofuel production for example. Also the invention further relates to research tools and methods for use in basic scientific research involving molecular genetics.

BACKGROUND TO THE INVENTION

Site-specific nucleases can permit the generation of double strand breaks (DSBs) at selected positions along a strand of DNA. In an organism of interest, this enables DSBs to be made at pre-determined positions in the genome. The creation of such breaks by site-specific nucleases prompts the endogenous cellular repair machinery to be repurposed in order to insert, delete or modify DNA at desired positions in the genome of interest. Targeted DNA cleavage mediated by site-specific nucleases is therefore an important basic research tool which has facilitated the functional determination and annotation of specific genes but amongst other things has also enabled the targeted mutation, addition, replacement or modification of genes in organisms of agricultural, industrial or commercial significance. As the genetic basis of both desirable and undesirable organismal phenotypes is uncovered through DNA sequencing, the ability to generate targeted alterations at specific genomic loci is fundamental to the genetic engineering of useful traits and in the development of clinical treatments for diseases with a genetic basis.

Other site specific nuclease approaches involve single strand target nucleic acid breaks, whether singly or in combination.

During the past decade, a range of molecular tools have been developed to allow for specific genetic engineering in general, and for dedicated editing of eukaryotic genomes in particular. Initially Zinc-Finger Nucleases (ZFNs) were developed, followed by Transcription Activator-Like Effector Nucleases (TALEN5). Recently, a revolution has been caused by the development of the CRISPR-associated Cas9 nuclease, as a very efficient, generic and cheap alternative for dedicated genome surgery in a range of eukaryotic cells (from yeast and plant to zebrafish and human) (reviewed by Van der Oost 2013, Science 339: 768-770, and Charpentier and Doudna, 2013, Nature 495: 50-51).

Many useful site-specific nucleases have been discovered in and isolated from prokaryotes. Just like eukaryotes, prokaryotic organisms possess a variable set of defence systems to protect themselves against viruses. The defence strategies that protect their microbial host against invading DNA mainly rely on general (innate) immunity systems, such as the well-known restriction enzymes.

A major recent discovery in this area has been the demonstration of a specific (adaptive) immunity system in bacteria and archaea. This adaptive immune system consists of clustered regularly interspaced palindromic repeats (CRISPR), and CRISPR-associated Cas genes that encode the Cas proteins. The CRISPR-Cas system uses small CRISPR RNAs that guide effector Cas proteins to complementary invading nucleic acids, eventually neutralizing the invasion. Two classes of Cas effector complexes are distinguished: multi-subunit complexes (e.g. *E. coli* Cascade) and single-protein systems (e.g. *Streptococcus pyogenes* Cas9) (Van der Oost et al., 2014, Nature Rev. Microbial. 12: 479-492).

Molecular analyses of CRISPR-Cas have provided the foundation for the development of genome engineering tools. Cas9 is a relatively simple CRISPR-Cas effector complex that can be functionally expressed in a wide range of prokaryotic and eukaryotic cells. Importantly, the RNA guide of Cas9 can easily be manipulated to specifically target any sequence of interest. Although adjusting the specificity for a certain target gene is also possible with the TALEN system, a drawback of this system is that this requires laborious protein engineering. In case of Cas9, only a short oligonucleotide has to be generated and cloned, saving time and money. Applications of the Cas9 system include general genetic engineering (disruption, repair and integration of genes), control of gene expression (stimulation and silencing) and gene labelling (imaging). Co-expression of Cas9 with different guides allows for multiplexing, for instance generating multiple knockouts simultaneously.

The CRISPR-Cas system allows target-specific cleavage of genomic DNA guided by Cas9 nuclease in complex with a guide RNA (gRNA) that complementarily binds to a 20 nucleotide targeted sequence. Alteration of the sequence of the gRNA therefore allows the Cas9 endonuclease to be programmed to cut double-stranded DNA at sites complementary to the 20-base-pair guide RNA. The Cas9 system has been used to modify genomes in multiple cells and organisms.

Compared with alternative genome editing systems (Zinc Finger Nucleases, TALEN), engineering by Cas9 is very efficient, cheap, and fast.

Despite these developments, the Cas9 system still has some practical draw-backs. Firstly, based on an intrinsic self/non-self-discrimination mechanism, Cas9 requires a sequence motif (protospacer adjacent motif, PAM) in the flanking region adjacent to the target sequence. The PAM-requirement imposes a significant design limitation on the endonuclease system, excluding potential target sites.

Secondly, although RNA-guided nucleases such as Cas9 incorporate guide RNAs which direct cleavage of specific target sites and therefore exhibit a reduction in the significant off-target activity observed in most other available nucleases, a certain level of off-target cleavage still occurs (Pattanayak et al., 2013, Nat. Biotechnol. 31: 839-843), that is, cleavage of genomic sequences that differ from the intended target sequence by one or more nucleotides. Generally, 15-17 nucleotides are required for base pairing with a 20 nucleotide complementary target; the tolerance for mismatches having been hypothesized to explain reported off-target problems. The imperfect specificity of engineered site-specific binding can lead to unintended insertion, modification or deletion of genomic loci during a gene targeting event, which has been associated with cellular toxicity. The consequences of such off target cleavage events resulting in undesired alterations of genomic loci other than the desired target can be extremely serious in a clinical context.

The sequence-specific cleavage of the intended nuclease target site in the absence of, or with only minimal background off-target cleavage activity is a prerequisite for high-efficiency genomic manipulation in basic research applications and especially in avoiding the cleavage of unintended genes during targeted genomic modifications associated with clinical applications of the site-specific endonuclease technologies, particularly since the resulting double-stranded breaks result in stable, heritable genome modifications.

Despite a great deal of attention being focussed on addressing these undesired features of the Cas9 system, to date they remain largely unresolved.

Imprecise specificity in particular continues to remain a difficulty and has only partially been addressed by expanding the to-be-recognised target sequence by dimers of catalytically inactivated Cas9 fused to the nuclease domain of FokI (dCas9-FokI) (Guilinger et al., 2014, Nat. Biotechnol. 32: 577-582). In addition, engineered nickase variants of Cas9 (in which one of the two nuclease sites is disrupted) have been demonstrated to facilitate homology directed repair in eukaryotic genomes with increased specificity and reduced off-target activity (Ran et al., 2013, Cell 154: 1380-1389. Also, Mali et al., 2013, Nat. Biotechnol. 31: 833-838).

WO 2015/035139 describes compositions, methods, systems, and kits for controlling the activity and/or improving the specificity of RNA-programmable endonucleases, such as Cas9. For example, guide RNAs (gRNAs) are engineered to exist in an "on" or "off" state, which control the binding and hence cleavage activity of RNA-programmable endonucleases. Also described are mRNA-sensing gRNAs that modulate the activity of RNA-programmable endonucleases, based on the presence or absence of a target mRNA. Some gRNAs are described that modulate the activity of an RNA-programmable endonuclease based on the presence or absence of an extended DNA (xDNA).

Another approach to mitigate off-target activity has centred on the development of software packages to aid in the guide RNA design process by undertaking exhaustive target sequence searches against genomic reference sequences, allowing the selection of target sequences with minimal off-target cleavage effects (Naito et al., 2015, Bioinformatics 31: 1120-1123). However, this merely enables efficient exploration of the target sequence space available for guide sequence design rather than directly addressing the inherent limitations of CRISPR-Cas9 as a genome editing tool.

Thus, currently available nucleases, including CRISPR-Cas9 systems, are not in their current state of development necessarily suitable for the majority of clinical applications or indeed many other target-sensitive genome editing applications. There is a continuing need for genome editing tools with greater inherent specificity and reliability than is currently available in the art.

Schunder et al. provided the first indication of a functional CRISPR/Cas system in *Francisella tularensis* (Schunder et al., 2013, *International Journal of Medical Microbiology* 303: 51-60). However, until now the structure and functionality of the system has remained unclear.

Subsequently, a classification of all known CRISPR adaptive immune systems of Archaea based primarily on their concatenated Cas protein sequences was provided by Vestergaard et al. in which Cas_Cpf1 was identified as a single protein interference system lacking Cas3, Cas5, Cas7 and Cas8, reminiscent of Cas9 in bacterial Type II systems despite not appearing to share any structural domains (Vestergaard et al., 2014, *RNA biology* 11.2 {2014): 156-167).

SUMMARY OF THE INVENTION

In seeking to overcome certain practical disadvantages associated with the Cas9 systems, the inventors provide a novel nuclease (Cpf1) unrelated to Cas9 for application as a gene editing tool. Cpf1 has been found to have uniquely advantageous mechanistic features such as a single nuclease domain and an upstream PAM motif and finds application as an improved tool for dedicated genome editing in general, and for repairing genetic disorders of human stem cells. Additionally, the Cpf1 nuclease can function as part of a multiplex engineering system for micro-organisms.

Accordingly, the present invention provides an isolated polypeptide or fragment thereof, comprising the amino acid sequence SEQ ID NO: 1 or a sequence of at least 60% identity therewith, and having a nuclease activity.

In preferred aspects, the polypeptide or fragment comprises an amino acid sequence of at least 75%; preferably at least 85%; more preferably at least 90%; even more preferably at least 95% of SEQ ID NO:1.

The invention is based on reference SEQ ID NO:1 but includes any variant sequence having the defined percentage identity therewith. Such percentage identities include any of the following: a reference nucleic or amino acid sequence and sequences of at least a certain percentage identity are disclosed, e.g. at least 60%, then optionally the percentage identity may be different. For example: a percentage identity which is selected from one of the following: at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5% or at least 99.8%. Such sequence identity with a SEQ ID NO: 1 amino acid sequence is a function of the number of identical positions shared by the sequences in a selected comparison window, taking into account the number of gaps, and the length of each gap, which need to be introduced for optimal alignment of the two sequences.

In all aforementioned aspects of the present invention, amino acid residues may be substituted conservatively or non-conservatively. Conservative amino acid substitutions refer to those where amino acid residues are substituted for other amino acid residues with similar chemical properties (e.g., charge or hydrophobicity) and therefore do not alter the functional properties of the resulting polypeptide. Similarly it will be appreciated by the skilled reader that nucleic acid sequences may be substituted conservatively or non-conservatively without affecting the function of the polypeptide. Conservatively modified nucleic acids are those substituted for nucleic acids which encode identical or functionally identical variants of the amino acid sequences. It will be appreciated by the skilled reader that each codon in a nucleic acid (except AUG and UGG; typically the only codons for methionine or tryptophan, respectively) can be modified to yield a functionally identical molecule. Accordingly, each silent variation (i.e. synonymous codon) of a polynucleotide or polypeptide, which encodes a polypeptide of the present invention, is implicit in each described polypeptide sequence.

The present invention provides a polypeptide or fragment having nuclease activity and comprising the amino acid sequence motif: FQIYN (SEQ ID NO: 2). This corresponds to residues 786-790 of SEQ ID NO:1.

The present invention also provides a polypeptide or fragment having nuclease activity and comprising the amino acid sequence motif: FQIYNK (SEQ ID NO: 3). This corresponds to residues 786-791 of SEQ ID NO:1.

The present invention also provides a polypeptide or fragment having nuclease activity and comprising the amino acid sequence motif: FQIYNKD (SEQ ID NO: 4). This corresponds to residues 786-792 of SEQ ID NO:1.

The present invention also provides a polypeptide or fragment having nuclease activity and comprising the amino acid sequence motif: $X^1X^2X^3 X^4X^5$FQIYNKD$X^6X^7$ corresponding to residues 781-794 of SEQ ID NO:1, wherein $X^1$ is one of G or K, $X^2$ is one of K, S or D, $X^3$ is one of L or I, $X^4$ is one of Y or F, $X^5$ is one of L or M, $X^6$ is one of F or Y and $X^7$ is one of S, A or V (SEQ ID NO: 5).

In another aspect the present invention provides a polypeptide or fragment having nuclease activity and comprising the amino acid sequence motif: GKLYLFQIYNKDFS (SEQ ID NO: 6). This corresponds to residues 781-794 of SEQ ID NO:1.

The amino acid sequence motif may instead comprise residues selected from 784-794, 785-794, 786-794, 787-794, 788-794 or 789-794 of SEQ ID NO: 1. The motif may be selected from residues 783-793, 783-792, 783-791, 783-790, 783-789 or 783-788 of SEQ ID NO:1. Also, the motif may be selected from residues 784-793, 785-792 or 786-790 of SEQ ID NO:1.

Alternatively, in aspects of the invention where a catalytically inactive version of Cpf1 is provided, the RuvC domain may comprise a Glu (E) residue, and short motif Glu-Ile-Asp (GID).

Alternatively, in aspects of the invention where a catalytically inactive version of Cpf1 is provided, the RuvC domain may comprise a Glu (E) residue, and short motif Gly-Ile-Asp (GID).

In aspects of the invention where a catalytically inactive version of Cpf1 is provided, the RuvC domain may comprise a Glu (E) residue, and short motif Glu-Ile-Asp (EID).

In aspects of the invention where a catalytically inactive version of Cpf1 is provided, the RuvC domain may comprise a Glu (E) residue, and short motif Ser-Ile-Asp (SID).

In aspects of the invention where a catalytically inactive version of Cpf1 is provided, the RuvC domain may comprise the amino acid sequence motif: $X^8$IDRGER wherein $X^8$ is one of G or S (SEQ ID NO: 7).

In aspects of the invention where a catalytically inactive version of Cpf1 is provided, the RuvC domain may comprise the amino acid sequence motif: DANGAY (SEQ ID NO: 8).

In aspects of the invention where a catalytically inactive version of Cpf1 is provided, the RuvC domain may comprise the amino acid sequence motif: E$X^9$LN wherein $X^9$ is one of D, N or E (SEQ ID NO: 9).

In aspects of the invention where a catalytically inactive version of Cpf1 is provided, the RuvC domain may comprise the amino acid sequence motif: EDLN (SEQ ID NO: 10).

A polypeptide or fragment of the invention may be defined both in terms of the reference sequence SEQ ID NO:1 and any percentage variant thereof, in combination with any of the aforementioned amino acid motifs as essential features.

In any aspect of the invention herein, the protein or polypeptide may have an RuvC (nuclease) domain.

In accordance with the invention, the RuvC domain may comprise a short motif GID.

In accordance with the invention, the RuvC domain may comprise a short motif SID.

In accordance with the invention, the RuvC domain may comprise a Glu (E) residue, and short motif GID.

The RuvC domain may comprise a Glu (E) residue, and short motif SID.

Where the RuvC domain comprises a Glu (E) residue, and short motif GID or SID, the D (aspartate) residue of the motif may be a catalytic residue.

The RuvC domain may comprise the amino acid sequence motif $X^8$IDRGER (SEQ ID NO: 7) wherein $X^8$ is one of G or S. For example, the protein or polypeptide may have an RuvC (nuclease) domain, wherein the RuvC domain comprises the amino acid sequence motif SIDRGER (SEQ ID NO: 11).

Where the RuvC domain comprises an amino acid sequence motif GIDRGER (SEQ ID NO: 12) or SIDRGER (SEQ ID NO: 11), the D (aspartate) residue of the motif may be a catalytic residue.

The protein or polypeptide may have an RuvC (nuclease) domain, wherein the RuvC domain may comprise the amino acid sequence motif DANGAY (SEQ ID NO: 8).

Where the RuvC domain comprises an amino acid sequence motif DANGAY (SEQ ID NO: 8), the D (aspartate) residue of the motif may be a catalytic residue.

The protein or polypeptide may have an RuvC (nuclease) domain, wherein the RuvC domain may comprise the amino acid sequence motif: E$X^9$LN wherein $X^9$ is one of D, N or E (SEQ ID NO: 9). For example, the protein or polypeptide may have an RuvC (nuclease) domain, wherein the RuvC domain comprises the amino acid sequence motif: EDLN. Where the RuvC domain comprises an amino acid sequence motif EDLN (SEQ ID NO: 10), ENLN (SEQ ID NO: 13) or EELN (SEQ ID NO: 14), theE (glutamate) residue of the motif may be a catalytic residue.

In accordance with the invention, the polypeptide or fragment may have an RuvC (nuclease) domain comprising a Glu (E) residue, and the amino acid sequence motifs SID and DANGAY (SEQ ID NO: 8).

Optionally, the polypeptide or fragment may have an RuvC (nuclease) domain comprising a Glu (E) residue, and the amino acid sequence motifs SID and EDLN (SEQ ID NO: 10).

Optionally, the polypeptide or fragment may have an RuvC (nuclease) domain comprising a Glu (E) residue, and the amino acid sequence motifs SID, DANGAY (SEQ ID NO: 8) and EDLN (SEQ ID NO: 10).

Optionally, the RuvC (nuclease) domain may comprise the amino acid sequence motif: $X^8$IDRGER wherein X8 is one of G or S, and the amino acid sequence motif DANGAY (SEQ ID NO: 8).

Optionally, the RuvC (nuclease) domain may comprise the amino acid sequence motif: $X^8$IDRGER wherein $X^8$ is one of G or S (SEQ ID NO: 7), and the amino acid sequence motif: $EX^9LN$ wherein X: is one of D, N or E (SEQ ID NO: 9).

Optionally, the RuvC (nuclease) domain may comprise the amino acid sequence motif: $X^8$IDRGER wherein X8 is one of G or S (SEQ ID NO: 7), and the amino acid sequence motif: EDLN (SEQ ID NO: 10).

Optionally, the RuvC (nuclease) domain may comprise the amino acid sequence motif: $X^8$IDRGER wherein $X^8$ is one of G or S (SEQ ID NO: 7), and the amino acid sequence motif: DANGAY (SEQ ID NO: 8) and the amino acid sequence motif: $EX^{9L}N$ wherein $X^9$ is one of D, N or E (SEQ ID NO: 9).

Optionally, the RuvC (nuclease) domain may comprise the amino acid sequence motif: $X^8$IDRGER wherein $X^8$ is one of G or S (SEQ ID NO: 7), and the amino acid sequence motifs DANGAY (SEQ ID NO: 8) and EDLN (SEQ ID NO: 10).

Preferably, the RuvC (nuclease) domain will comprise the amino acid sequence motifs: SIDRGER (SEQ ID NO: 11), DANGAY (SEQ ID NO: 8) and EDLN (SEQ ID NO: 10).

In other aspects, the polypeptide or fragment may have an Arginine-rich motif.

The Arginine-rich motif may comprise the amino acid sequence motif: $X^{10}YX^{11}X^{12}X^{13}LX^{14}X^{15}X^{16}EX^{17}X^{18}X^{19}X^{20}X^{21}ARX^{22}X^{23}$, wherein $X^{10}$ is one of D or N, $X^{11}$ is one of R, Q or H, $X^{12}$ is one of K, E, S or D, $X^{13}$ is one of A, K or L, $X^{14}$ is one of D, N or A, $X^{15}$ is one of V, N, Q, K or A, $X^{16}$ is one of R, K or I, $X^{17}$ is one of Y, K or I, $X^{18}$ is one of D or E, $X^{19}$ is one of N, R or M, $X^{20}$ is one of K, V, F or D, $X^{21}$ is one of E, A, D or S, $X^{22}$ is one of R, Q or K and $X^{23}$ is one of N, A, S or D (SEQ ID NO: 15).

The Arginine-rich motif may comprise the amino acid sequence motif:

DYRKALDVREYDNKEARRN, (SEQ ID NO: 16)

DYQKKLDNREKERVAARQA, (SEQ ID NO: 17)

DYREKLNQREIEMKDARQS, (SEQ ID NO: 18)

DYHSLLDKKEKERFEARQN, (SEQ ID NO: 19)
or

NYHDKLAAIEKDRDSARKD. (SEQ ID NO: 20)

In accordance with the invention, the polypeptide or fragment may have an RuvC (nuclease) domain comprising a Glu (E) residue, and the amino acid sequence motifs Ser-Ile-Asp (SID), DANGAY (SEQ ID NO: 8) and EDLN (SEQ ID NO: 10) the amino acid sequence motif. Preferably, the RuvC (nuclease) domain will comprise the amino acid sequence motif: $X^8$IDRGER wherein $X^8$ is one of G or S (SEQ ID NO: 7), and the amino acid sequence motifs DANGAY (SEQ ID NO: 8) and EDLN (SEQ ID NO: 10). More preferably, the RuvC (nuclease) domain will comprise the amino acid sequence motifs: SIDRGER (SEQ ID NO: 11), DANGAY (SEQ ID NO: 8) and EDLN (SEQ ID NO: 10).

In further embodiments a polypeptide or fragment of any aspect of the invention preferably does not comprise an HNH (nuclease) domain. Additionally or alternatively, in yet a further embodiment, a polypeptide or fragment of any aspect of the invention does not comprise a recognition lobe that is typically present in Cas9. Certain polypeptides or fragments of the invention may have nuclease activity that is provided by a single site in the polypeptide.

Other polypeptides or fragments of the invention may further comprise a zinc finger-domain, although the metal-binding site (typically 4 amino acids, Cys and/or His) is not complete in all Cpf1 variants.

Polypeptides or fragments of the invention may have a nuclease activity which is single strand cleavage, e.g. nickase activity.

Preferably, two subunits of Cpf1 may be used in a dimeric arrangement where nuclease domains of each of the two subunits cleave individual DNA strands. Preferably, such a dimer may be a homodimer where the RuvC-like domains of each of the two subunits cleave individual DNA strands. Alternatively, Cpf1 polypeptides of the invention may be engineered to contain more than one nuclease domain, native or otherwise, which permit cleavage of both DNA strands.

Polypeptide or fragments of the invention preferably have binding affinity for a guide RNA molecule.

In other aspects, a polypeptide or fragment of the invention may have a guide RNA comprising a sequence substantially complementary to a sequence comprised in a target nucleic acid strand.

In further embodiments, a polypeptide or fragment of the invention preferably has binding affinity for a polynucleotide sequence motif in a target nucleic acid strand. This sequence motif is usually known as a protospacer adjacent motif (PAM) sequence. Preferably the nucleotide sequence motif is at least 3 contiguous nucleic acid residues.

The PAM is located on the target (adjacent to protospacer). Typically, the SEED domain of the guide RNA (the region most likely responsible for initial guide/target base pairing) is complementary to the target nucleic acid sequence. Preferably, the SEED part of the guide does not tolerate mismatches.

In order to further improve the polypeptides or fragments of the invention, additional amino acids may be added, preferably by way of a fusion to the N or C terminus. The additional amino acid sequence may have nucleic acid or chromatin modifying, visualising, transcription activating or transcription repressing activity and is preferably translationally fused through expression in natural or artificial protein expression systems, or covalently linked by a chemical synthesis step to the at least one subunit; preferably the at least one functional moiety is fused or linked to at least the region of the N terminus and/or the region of the C terminus.

The additional amino acid sequence having nucleic acid or chromatin modifying, activating, repressing or visualising activity may be a protein; optionally selected from a helicase, a nuclease, a nuclease-helicase, a DNA methyltransferase (e.g. Dam), or DNA demethylase, a histone methyltransferase, a histone demethylase, an acetylase, a deacetylase, a phosphatase, a kinase, a transcription (co-) activator, an RNA polymerase subunit, a transcription repressor, a DNA binding protein, a DNA structuring protein, a marker protein, a reporter protein, a fluorescent protein, a ligand binding protein (e.g. mCherry or a heavy metal binding protein), a signal peptide (e.g. TAT-signal sequence), a subcellular localisation sequence (e.g. nuclear localisation sequence) or an antibody epitope.

When the protein is a nuclease, it may be one selected from a type II restriction endonuclease such as FokI, or a mutant or an active portion thereof. Preferably, one protein complex of the invention may be fused to the N terminal domain of Fokl and another protein complex of the invention may be fused to the C terminal domain of Fokl. These two protein complexes may then be used together (in a dimeric configuration) to achieve an advantageous locus specific double stranded cut in a nucleic acid, whereby the location of the cut in the genetic material is at the design and choice of the user, as guided by the RNA component (defined and described below) and due to presence of a so-called "protospacer adjacent motif" (PAM) sequence in the target nucleic acid strand (also described in more detail below).

In a preferred embodiment, a protein or polypeptide of the invention has an additional amino acid sequence which is a modified restriction endonuclease, e.g. Fokl. The modification is preferably in the catalytic domain. In preferred embodiments, the modified Fokl is KKR Sharkey or ELD Sharkey, which is fused to the Cpf1 protein. In a preferred application of these complexes of the invention, two of these complexes (KKR Sharkey and ELD Sharkey) may be together in combination. A heterodimer pair of protein complexes employing differently modified Fokl has particular advantage in targeted double stranded cutting of nucleic acid. If homodimers are used then it is possible that there is more cleavage at non-target sites due to non-specific activity. A heterodimer approach advantageously increases the fidelity of the cleavage in a sample of material.

Advantageously the above modifications can permit a user to select in a predetermined manner a precise genetic locus which is desired to be cleaved, tagged or otherwise altered in some way, e.g. methylation, using any of the nucleic acid or chromatin modifying, visualising, transcription activating or transcription repressing entities defined herein. The other component part of the system is an RNA molecule which acts as a guide for directing the complexes of the invention to the correct locus on DNA or RNA intending to be modified, cut or tagged.

In further embodiments, a polypeptide or fragment of the invention is preferably bound to a guide RNA and to a target nucleic acid. In this form a complex is formed which provides targeted DNA strand nuclease activity, wherein a desired target locus is cleaved.

In another aspect the present invention provides a polynucleotide comprising a polynucleotide sequence encoding a polypeptide or fragment of the invention as hereinbefore defined.

In further aspect, the present invention provides an expression vector comprising a polynucleotide as aforementioned.

The invention also provides an expression vector as defined above, further comprising a nucleotide sequence encoding a guide RNA which has substantial complementarity to a desired sequence in the target nucleic acid strand. Guide RNA in the native state is a single RNA consisting of a crRNA.

The invention further provides an expression vector of the invention which is preferably a viral vector, e.g. Adenovirus, or Adena-associated Virus (AAV).

In other aspects, the invention provides a host cell transformed to express a polypeptide or fragment of the invention as hereinbefore described.

Typically, the expression vector DNA can be delivered to the host cell by transformation, electroporation or virus (AAV). Also, RNA can be delivered into a host cell by injection or electroporation. Proteins can be delivered to cells via electroporation, peptide (HIV) tags. In another aspect the present invention provides a host cell as hereinbefore described, additionally transformed to contain a guide RNA comprising a sequence substantially complementary to a sequence comprised in a target nucleic acid strand in the host cell.

The invention includes any host cell transformed with an expression vector as hereinbefore described.

The invention also provides a method of cleaving a target nucleic acid strand at a specific locus, comprising exposing the target nucleic acid to a polypeptide or fragment of the invention, and with a guide RNA molecule which comprises a sequence substantially complementary to a sequence comprised in the target nucleic acid strand.

The invention further provides a method of cleaving a target nucleic acid strand at a specific locus in the genome of a cell of an organism, comprising transforming the cell with an expression vector of the invention as described herein, and transforming the cell with a vector which expresses a guide RNA comprising a sequence substantially complementary to a sequence comprised in a target nucleic acid strand.

In further aspect, the invention provides a method of cleaving a target nucleic acid strand at a specific locus in the genome of a cell of an organism, comprising transforming the cell with an expression vector of the invention as described herein.

In another aspect the present invention provides a method of non-homologous end joining gene editing comprising (a) transforming the cell with an expression vector of the invention, and transforming the cell with a vector which expresses a guide RNA comprising a sequence substantially complementary to a sequence comprised in a target nucleic acid strand; or (b) transforming the cell with an expression vector of the invention. In these aspects of the invention the polypeptides of the invention are modified or used to cause double stranded breaks.

In a further aspect the invention provides a method of homologous end joining gene editing comprising (a) transforming the cell with an expression vector of the invention, and transforming the cell with a vector which expresses a guide RNA comprising a sequence substantially complementary to a sequence comprised in a target nucleic acid strand; or (b) transforming the cell with an expression vector of the invention; so as to create a double strand break at a desired locus in the genetic material, and exposing the genetic material to a polynucleotide sequence which has end regions complementary to the broken end regions of the genetic material.

DETAILED DESCRIPTION

The protein of amino acid sequence SEQ ID NO: 1 is a large protein (about 1300 amino acids) that contains an RuvC-like nuclease domain homologous to the respective domains of Cas9 and transposable element ORF-B, along with an arginine-rich region similar to that in Cas9 and a Zinc Finger (absent in Cas9 but shared with ORF-8), but lacks the HNH nuclease domain that is present in all Cas9 proteins.

The invention will now be described in detail with reference to the examples and to the drawings in which:

FIG. 1 shows the domain structure of the novel CRISPR-Cas nuclease, Cpf1. Three RuvC nuclease domains, a Zinc-finger and an arginine-rich domain that allows for interaction with RNA guide and DNA target are shown.

Figure 2:
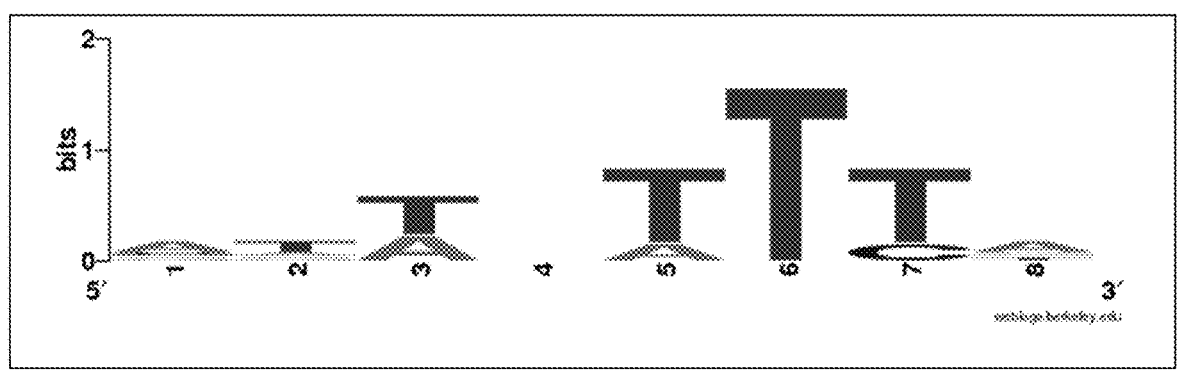
Figure 2:
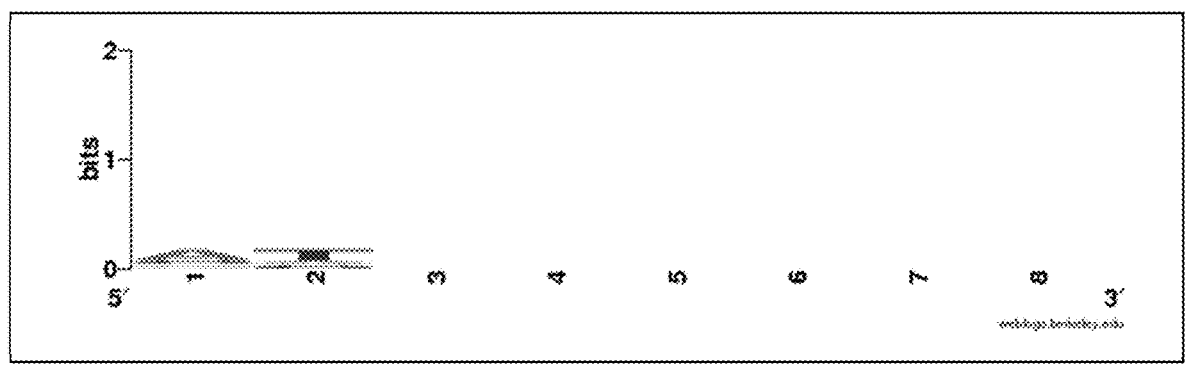

FIG. 2 shows the results of an in silico analysis of conserved Protospacer Adjacent Motif (PAM). Panel A shows a Weblogo based on 5' flanks of protospacers depicted in Table 1. Panel 8 shows a Weblogo based on 3' flanks of protospacers depicted in Table 1.

Figure 3B:
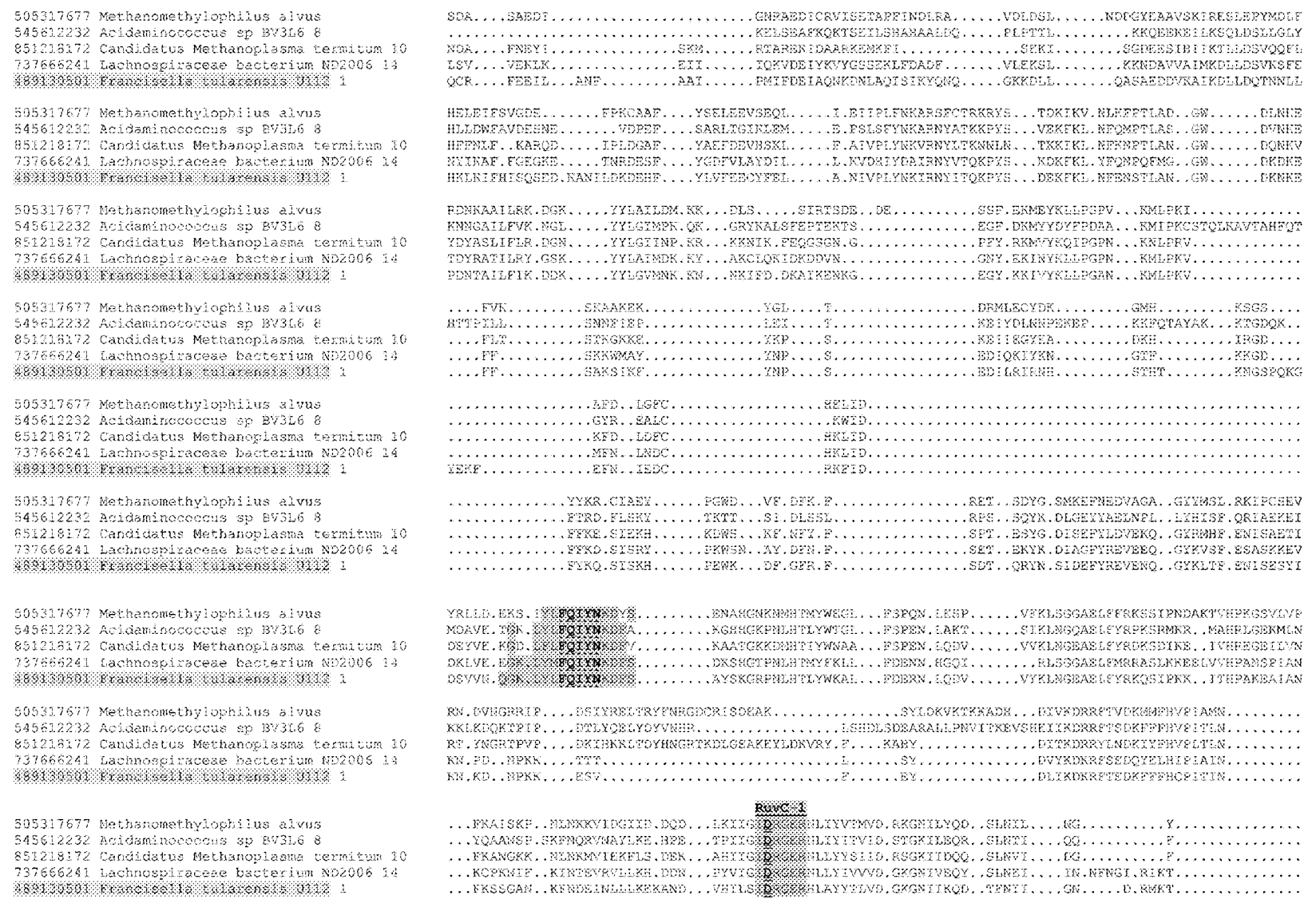
Figure 3C:
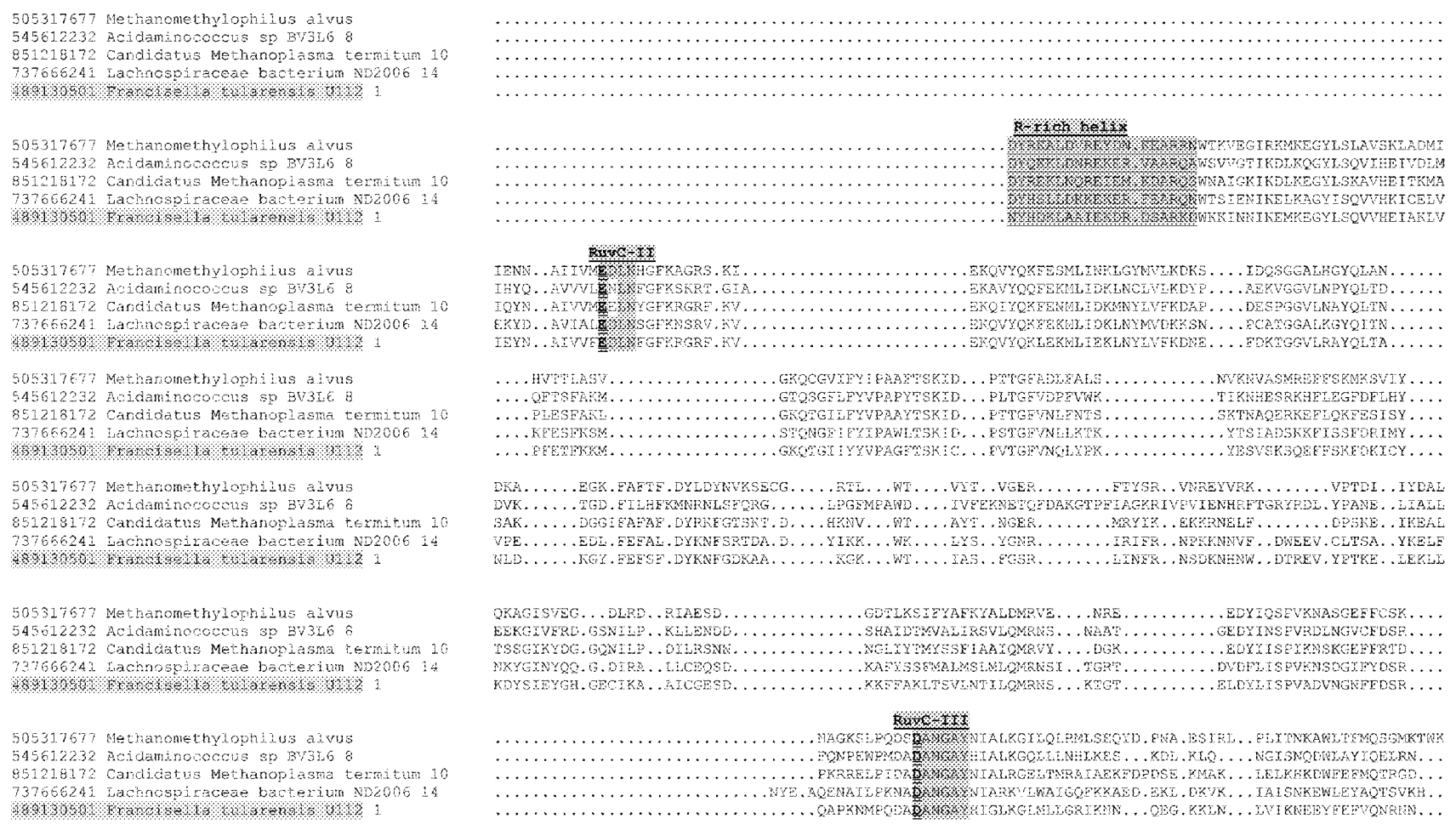

FIGS. 3A-3C show the results of a multiple alignment of the Cpf1 protein family_(SEQ ID NOS 32, 33, 36, 34 and 35, respectively, in order of appearance). Each sequence is labelled with GenBank Identifier (GI) number and systematic name of an organism. Predicted secondary structure (SS) is shown by shading. Active site residues of RuvC-like domain(s) are shown as bold and double underlined. Potential bridge helix is shown by shading and with single underline. The amino acid sequence FQIYN (SEQ ID NO: 2) is also indicated in bold, by shading and dotted underline.

EXAMPLE 1—NOVEL NUCLEASES FOR GENE EDITING

Specific examples are (1) CRISPR-associated Cpf1 from the marine bacterium *Francisella novicida* (Fn-Cpf1), and (2) CRISPR-associated Cpf1 from the archaean *Methanomethylophylus alvus* strain Mx1201 (Mai-Cpf1) that resides in the human gut.

Without the inventors wishing to be bound by any particular theory, Cpf1 recognises the crRNA in a sequence-specific manner, after which cleavage occurs of the double stranded RNA segment, and eventually formation of an effector complex consisting of Cpf1 and a single crRNA guide. Cpf1 may operate as a dimer, with the RuvC-like domains of each of the two subunits cleaving individual DNA strands. Alternatively, Cpf1 may contain more than one nuclease domain which permits cleavage of both DNA strands. Alternatively, one or more RuvC domains of Cpf1 may exhibit unusual flexibility that allows for cleavage of both strands.

The following examples were performed in parallel for the bacterial Fno-Cpf1 and archaeal Mai-Cpf1 protein variants:

Cloning is carried out of the entire CRISPR locus, including cas operon (cpf1-cas4-cas1-cas2), leader region, CRISPR array, and flanking regions (approximately 10 kb) in low-copy vector (e.g. pACYC184) in an *E. coli* K12 strain; no details are known about the maturation of the guide, which may be similar to that of Cas9 (tracrRNA/ RNaselll), or may be similar to that of Cascade (Cash-like ribonuclease, although that is not part of cpf1 operons), or may be unique. Further detailed materials and methods are provided in Sapranauskas et al., 2011, Nucleic Acids Res.39: 9275-9282.

Standard procedures were used to optimize chances for functional protein production of the selected Cpf1 proteins in *E. coli*: (i) by performing codon harmonization design to adjust cpf1 nucleotide sequences (see Angov et al., 2008, PLoS One 3, e2189); (ii) by including N-terminal or C-terminal strepII tag, that will allow for affinity purification; (iii) by cloning synthetic gene in T7 expression vector (e.g. pET24d) and transform plasmid to non-production strain of *E. coli* (e.g. JM109, lacking T7 RNA polymerase gene), (iv) transferring plasmid via second transformation to production strain of *E. coli* (e.g., BL21(DE3), containing T7 RNA polymerase gene under control of rhamnose promoter, that allows for accurate tuning of expression, (v) varying expression conditions (medium, inducer concentration, induction time), (vi) using optimal conditions for liter-scale cultivation, after which cells are harvested and mechanically disrupted to obtain cell-free extract (small volumes by sonication; large volumes by French Press), (vii) separating membrane and soluble fractions, and perform affinity purification using streptactin resin, (viii) testing relevant fractions by SDS-PAGE, and storing the pure protein for subsequent analyses.

As well as the above, additionally, the predicted crRNA gene is sequenced, or a single-guide RNA (sgRNA) gene is made, e.g. by adding 4 nucleotide synthetic loops (Jinek et al., 2012, Science 337: 816-821); RNA genes residing either on the same plasmid as cpf1 gene, or on a separate plasmid.

Additionally, a catalytically inactive Cpf1 mutant is made (RuvC active site contains conserved glutamate (E) as well as GID motif).

Additionally, a catalytically inactive Cpf1 mutant is made (RuvC active site contains conserved glutamate (E) as well as SID motif).

Also, N-terminal or C-terminal fusions are made of the Cpf1 mutant with FokI nuclease domain with differently connecting linkers (as described for Cas9; see Guilinger et al., 2014, Nat. Biotechnol. 32: 577-82).

Example 2—Biochemical Characterization of Cpf1 Nucleases

These experiments characterize guide surveillance and target cleavage. The CRISPR system is an adaptive immunity system in bacteria and archaea. The CRISPR arrays consist of identical repeats (e.g. 30 bp) and variable spacers (e.g. 35 bp). The adaptive nature of the CRISPR system relies on regular acquisition of new spacers, often corresponding to fragments (protospacers) derived from viruses. Acquisition generally depends on the selection of a protospacer based on the presence of a protospacer adjacent motif (PAM). The presence of this motif is crucial for the eventual interference by the CRISPR-associated effector complex (e.g. Cas9) with its crRNA guide. The PAM motif allows for self versus non-self discrimination: the potential target sequences (i.e. complementary to the crRNA guide sequence) reside both on the host's genome (the self CRISPR array) as well as on the invader's genome (the non-self protospacer); the presence of the protospacer in the invader DNA triggers the effector complex to bind it in a step-wise manner; when perfect base pairing occurs between the sequence of the protospacer immediately adjacent to the PAM (the so-called seed sequence), then base pairing as a zipper, eventually leading to a state of Cas9 to catalyse cleavage of the target DNA strands (see Jinek et al., 2012, Science 337: 816-821; also Gasiunas et al., 2012, PNAS 109: E2579-E2586).

In silico analysis of the Cpf1-associated PAM by BLAST analysis of the CRISPR spacers of the cpf1-loci. BLAST analysis of some spacers shows several homologous sequences (90-100% identity), (Table 1). The most promising hits concern identical sequences of virus genes in general, and genes of prophages in particular. Prophages are derived from lysogenic viruses, the genomes of which have integrated in the genome of bacteria. As is the case with eukaryotic viruses, the host range of prokaryotic viruses is often rather limited; hence, when the matching prophage is found in a bacterium that is closely related to the bacterium that has the corresponding spacer sequence in its CRISPR array, this gives some confidence that it is a real hit. In other words, it may well be that the prophage resembles a virus that has attempted to infected the CRISPR-containing bacterium, but the invasion has resulted in spacer acquisition and virus immunity of the latter bacterium.

TABLE 1

| Fn sub species Spacer# | Host of prophage, target gene accession number | | Alignment of Fn sub species spacer with protospacer (plus 8 nt flanks on both sides) | SEQ ID NO: |
|---|---|---|---|---|
| Francisella novicida U112 #1 | Francisella novicida 3523, hypo prot AEE26301.1 | spacer protospacer | 5' AGATTAAAAGGTAATTCTATCTTGTTGAG<br>\|\|\|\|\|\|\|\|\|\|\|\|\|\|\|\|\|\|\|o\|\|\|\|\|\|\|\|<br>5' ATAATTTAAGATTAAAAGGTAATTCTATTTTG TTGAGATCTGAGC | 21<br><br>22 |
| Francisella novicida U112 #2 | Francisella novicida 3523, intergenic sequence in prophage | Spacer protospacer | 5'        TAGCGATTTATGAAGGTCATTTTTTT<br>\|\|\|\|\|\|\|\|\|\|\|\|\|\|\|\|\|\|\|\|\|\|\|\|\|<br>5' CTAAATTATAGCGATTTATGAAGGTCATTTTT TTAAAAAGTT | 23<br><br>24 |
| Francisella novicida Fx1 #1 | Francisella novicida 3523, hypo prot AEE26295.1, "phage major tail tube protein" | Spacer protospacer | 5' ATGGATTATTACTTAACTGGAGTGTTTAC<br>\|\|\|\|\|\|\|\|\|\|\|\|\|\|\|\|\|\|\|\|\|o\|\|\|\|\|\|o\|\|\|<br>5' AATGTTCAATGGATTATTACTTAATTGGAGTG TCTACGTCGATGG | 25<br><br>26 |
| Francisella novicida FTG #1 | Francisella novicida 3523, hypo prot YP_0058240 59.1 | Spacer protospacer | 5' GCCACAAATACTACAAAAAATAACTTAA<br>\|\|oo\|\|\|\|\|\|\|\|\|\|\|\|\|\|\|\|\|\|\|<br>5' ATTTTTTGGCTCCAAATACTACAAAAAATAAC TTAAACTTTGAA | 27<br><br>28 |
| Francisella novicida GA99-3549 #1 | Francisella novicida 3523, hypo prot FN3523_1009, "baseplate_J" | Spacer protospacer | 5' ATTGTCAAAACATAAGCAGCTGCTTCAAATAT<br>\|o\|\|\|o\|oo\|\|\|\|\|\|\|\|\|\|o\|\|\|\|\|\|\|\|\|\|\|<br>5' GGTCTTTTACTGTTATTACATAAGCAGCCGCT TCAAATATCTTAGCAA | 29<br><br>30 |

Analysis of the sequences flanking the protospacers in the prophage genes resulted in a T-rich conserved motif; interestingly, this motif does not reside downstream the protospacer (as in the Cas9 system), but rather upstream. Though not wishing to be bound by particular theory, the inventors find that Cpf1 of the invention requires a PAM-like motif (3-4 nucleotides) for binding a target DNA molecule that is complementary to the guide, has a seed sequence (8-10 nucleotides) in which no mismatches are allowed, and has a single nuclease site that allows for nicking of the base paired target DNA strand.

PAM motifs of Cpf1 and variants of the invention were also characterized using the approach of Jiang et al., 2013, Nat. Biotechnol. 31: 233-239). Two derivatives of *E. coli* BL21(DE3) were used, initially transformed either with a target-plasmid or with a non-target plasmid; two variant target plasmids used have a similar part (GFP marker, KmR marker, origin of replication) and a variable part with target sequence (protospacer) with an associated degenerate PAM (5-8 variable nucleotides) either upstream or downstream of the protospacer); next, this strain was transformed with a Cpf1-expression plasmid (includes design-CRISPR with single-guide RNA (sgRNA, CmR-marker); screening for transformants was on plates with chloramphenicol (Cm) (not kanamycin (Km)), and screening for non-fluorescent colonies, indicating loss-of-target-plasmid. As the plasmids with the correct PAMs will be lost, DNA Deep Seq was performed of appropriate PCR products of the entire pool of target plasmid, before and after transformation. The differences reveal the PAM (Bikard et al., 2013, Nucleic Acids Res. 41: 7429-7437).

PAM signatures were confirmed by in vitro characterization of cleavage activity of BsCas9/sgRNA; assays reveal optimal conditions (temperature, buffer/pH, salt, metals).

Presence of a seed sequence in the PAM was established according to methods described by Jinek et al., 2012, Science 337: 816-821.

Example 3—Bacterial Engineering

Performing of high-throughput engineering of bacterial genome with nuclease variants. Without wishing to be bound by particular theory, the inventors expect that Cpf1/ guide complexes of the invention allow for specific targeting of genomic DNA. Multiplex targeting can be established by using a design CRISPR together with a matching crRNA.

The experiments provide application of Cpf1 and variants of the invention. Cas9 is tested in parallel as a reference.

Gene knock-in/knock-out (insertion/disruption of any sequence) is performed. The host strain *E. coli* K12 (LacZ+, GFP−) was engineered as follows: the gene encoding a variant of the Green Fluorescent Protein (GFPuv) is inserted in the lacZ gene, resulting in a clear phenotype (LacZ−, GFP+). The cpf1 gene was introduced on a plasmid (or derivatives of those plasmids), together with a fragment that allows for homologous recombination of the target sequence. A target (protospacer) sequence was selected, with an appropriate adjacently located PAM sequence; a corresponding guide designed, consisting of the crRNA (with spacer complementary to target protospacer) and the crRNA gene (as adapted from the method described for Cas9 by Jiang et al. (2013a) *RNA-guided editing of bacterial genomes using CRISPR-Cas systems*. Nat. Biotechnol. 31: 233-239).

Gene expression silencing (using catalytically inactivated Cas9, was as described: dCas9 derivative of Spy-Cas9; (Bikard et al., 2013, Nucleic Acids Res. 41: 7429-7437; Qi et al., 2013, Cell 152: 1173-1183);) by binding at promoter (RNA polymerase binding site) of target gene, or of target genes using a multiplex approach (using a design CRISPR).

Gene expression activation; as above (silencing); binding upstream binding site of RNA polymerase, with Cas9 fused to activation domain (as has been described for Spy-Cas9) (Bikard et al., 2013, Nucleic Acids Res. 41: 7429-7437).

Fusion of inactivated Cpf1 and the Fokl nuclease domain (described in Example 1 were compared with an active Cpf1 in different experimental set-ups. This required two simultaneous interactions of guides and targets, that results in a major improvement of cleavage at the desired site.

Example 4—Human Stem Cell Engineering

Targeted editing of disease-causing genetic mutations would be an elegant and effective treatment for genetic disease. Recently discovered gene editing systems such as Cas9, allow the specific targeting of disease-causing mutations in the genome, and can be used to functionally repair or permanently disable mutated genes. The efficiency of gene editing systems has been demonstrated in a laboratory setting, and are now routinely used in genome editing of a wide variety of cell types from many different species, including human. However, despite the success of these systems in the research setting, clinical application of gene editing systems is hampered by the lack of a suitable delivery system to introduce gene-editing technologies into patient cells in a safe, transient and efficient manner. Several labs are working on the development of recombinant viral vectors which can be used to deliver gene editing systems into patient cells, but prolonged expression of for example CRISPR/Cas9 from such vectors will increase the likelihood of off-target effects and is therefore not ideal. Intracellular delivery of recombinant gene editing protein and synthetic CRISPR RNA would be an effective, non-integrating and transient method for the application of gene editing technology in patient cells.

Recently a novel method has been developed that allows the transduction of native proteins into virtually any cell type (D'Astolfo et al., 2015, Cell, 161: 674-690). This technology, termed iTOP, for induced Transduction by Osmocytosis and Propanebetaine, is based on a combination of small molecule compounds, which trigger the uptake and intracellular release of native protein. iTOP is highly efficient, routinely achieving transduction efficiencies of >90% of cells, and works on a wide variety of primary cell types. It has been demonstrated that iTOP-mediated transduction of recombinant Cas9 protein and in vitro transcribed sgRNA allows for highly efficient gene editing in difficult-to-transfect cell types including human stem cells. Upon iTOP-CRISPR/Cas9 transduction, >70% bi-allelic gene targeting has been reported in human ES cells without the need for drug-selection of transduced cells.

Key advantages of iTOP over existing technologies are: (i) the ability to transduce primary (stem) cells with native protein at very high efficiency, (ii) the non-integrating, transient nature of protein mediated gene editing, ensuring safety and minimizing off-target effects, and (iii) the tight control of dosage and timing of the delivered protein. We have demonstrated that iTOP-CRISPR/Cas9 is an effective tool to modify a large variety of primary (patient) cell types. However, due to size and protein solubility issues, production of recombinant Cas9 is hampering broad-scale (clinical) adoption of this system. Cpf1 could solve these problems and pave the way for the development of novel therapies to treat genetic disease.

The iTOP technology will be used to allow efficient intracellular delivery of Cpf1 into human stem cells. The advantage of iTOP is its highly flexible approach. First, NaCl-mediated hypertonicity induces intracellular uptake op protein via a process called macropinocytosis (D'Astolfo op. cit.)). Second, a propanebetaine transduction compound (NDSB-201 or gamma-aminobutyric acid (GABA) or others triggers the intracellular release of protein from the macropinosome vesicles. In addition to these compounds, osmoprotectants such as glycerol and glycine are added to help cells to cope with the NaCl-induced hypertonic stress. By varying the concentration of NaCl, the concentration and type of transduction compound and/or the concentration and type of osmoprotectants, the iTOP system can be adapted and optimised to meet the specific requirements of the cargo protein and/or the target cells. iTOP parameters were optimized to allow efficient gene editing of human embryonic stem cells (hESCs), targeting the endogenous WDR85 gene by Cpf1 (equipped with an N- or C-terminal nuclear localization signal (NLS)), as recently shown for Cas9.

In the following sequence listing, the amino acid residues Glu Xaa Asp (single underlined) are the GID motif of an RuvC domain. Therefore in the SEQ ID NO: 1, the Xaa residue may be I.

The amino acid residues lie Asp Arg Gly Glu Arg (double underlined) include the IDR residues of an RuvC domain.

The amino acid residues Phe Glu Asp (triple underlined) include the E residue making up part of the active site residues of an RuvC domain.

Example 5 Multiple Alignment of Cpf1 Proteins

FIGS. 3A-3C show the results of an Multiple alignment of Cpf1 proteins. The alignment was built using MUSCLE program and modified manually on the basis of local PSI-BLAST pairwise alignments and HHpred output. Each sequence is labelled with GenBank Identifier (GI) number and systematic name of an organism. Five sequences analysis in this work are marked by the respective numbers. Secondary structure (SS) was predicted by Jpred and is shown is shown by shading. CONSENSUS was calculated for each alignment column by scaling the sum-of-pairs score within the column between those of a homogeneous column (the same residue in all aligned sequences) and a random column with homogeneity cutoff 0.8. Active site residues of RuvC-like domain(s) are shown as bold and double underlined. Potential bridge helix is shown by shading and with single underline. The amino acid sequence FQIYN (SEQ ID NO: 2) is also indicated in bold, by shading and dotted underline.

```
SEQUENCE LISTING

<110>    wageningen universiteit

<120>    cpf1 Nuclease

<130>    RAW/P223284GB

<160>    1

<170>    Patentin version 3.5

<210>    1

<211>    1304

<212>    PRT

<213>    Artificial sequence

<220>

<223>    Cpf1

<220>

<221>    misc_feature

<222>    (439)..(439)

<223>    Xaa can be any naturally occurring amino acid

<220>

<221>    misc_feature

<222>    (504)..(504)

<223>    Xaa can be any naturally occurring amino acid

<220>

<221>    misc_feature

<222>    (521)..(521)

<223>    Xaa can be any naturally occurring amino acid

<220>

<221>    misc_feature

<222>    (539)..(539)

<223>    Xaa can be any naturally occurring amino acid

<220>

<221>    misc_feature

<222>    (800)..(800)

<223>    Xaa can be any naturally occurring amino acid

<400>    1
```

Met ser Ile Tyr Gln Glu Phe Val Asn Lys Tyr Ser Leu Ser Lys Thr
1               5                   10                  15

Leu Arg Phe Glu Leu Ile Pro Gln Gly Lys Thr Leu Glu Asn Ile Lys
            20                  25                  30

Ala Arg Gly Leu Ile Leu Asp Asp Glu Lys Arg Ala Lys Asp Tyr Lys
        35                  40                  45

Lys Ala Lys Gln Ile Ile Asp Lys Tyr His Gln Phe Phe Ile Glu Glu
    50                  55                  60

Ile Leu Ser Ser Val Cys Ile Ser Glu Asp Leu Leu Gln Asn Tyr Ser
65                  70                  75                  80

-continued

```
Asp Val Tyr Phe Lys Leu Lys Lys Ser Asp Asp Asn Leu Gln Lys
                 85                  90                  95

Asp Phe Lys Ser Ala Lys Asp Thr Ile Lys Lys Gln Ile Ser Glu Tyr
            100                 105                 110

Ile Lys Asp Ser Glu Lys Phe Lys Asn Leu Phe Asn Gln Asn Leu Ile
        115                 120                 125

Asp Ala Lys Lys Gly Gln Glu Ser Asp Leu Ile Leu Trp Leu Lys Gln
    130                 135                 140

Ser Lys Asp Asn Gly Ile Glu Leu Phe Lys Ala Asn Ser Asp Ile Thr
145                 150                 155                 160

Asp Ile Asp Glu Ala Leu Glu Ile Ile Lys Ser Phe Lys Gly Trp Thr
                165                 170                 175

Thr Tyr Phe Lys Gly Phe His Glu Asn Arg Lys Asn val Tyr ser ser
            180                 185                 190

Asp Asp Ile Pro Thr ser Ile Ile Tyr Arg Ile val Asp Asp Asn Leu
        195                 200                 205

Pro Lys Phe Leu Glu Asn Lys Ala Lys Tyr Glu Ser Leu Lys Asp Lys
    210                 215                 220

Ala Pro Glu Ala Ile Asn Tyr Glu Gln Ile Lys Lys Asp Leu Ala Glu
225                 230                 235                 240

Glu Leu Thr Phe Asp Ile Asp Tyr Lys Thr ser Glu Val Asn Gln Arg
                245                 250                 255

Val Phe Ser Leu Asp Glu Val Phe Glu Ile Ala Asn Phe Asn Asn Tyr
            260                 265                 270

Leu Asn Gln ser Gly Ile Thr Lys Phe Asn Thr Ile Ile Gly Gly Lys
        275                 280                 285

Phe val Asn Gly Glu Asn Thr Lys Arg Lys Gly Ile Asn Glu Tyr [[r]]Ile
    290                 295                 300

Asn Leu Tyr Ser Gln Gln Ile Asn Asp Lys Thr Leu Lys Lys Tyr Lys
305                 310                 315                 320

Met Ser Val Leu Phe Lys Gln Ile Leu Ser Asp Thr Glu Ser Lys Ser
                325                 330                 335

Phe val Ile Asp Lys Leu Glu Asp Asp Ser Asp Val Val Thr Thr Met
            340                 345                 350

Gln ser Phe Tyr Glu Gln Ile Ala Ala Phe Lys Thr Val Glu Glu Lys
        355                 360                 365

Ser Ile Lys Glu Thr Leu Ser Leu Leu Phe Asp Asp Leu Lys Ala Gln
    370                 375                 380

Lys Leu Asp Leu Ser Lys Ile Tyr Phe Lys Asn Asp Lys Ser Leu Thr
385                 390                 395                 400

Asp Leu ser Gln Gln val Phe Asp Asp Tyr ser val Ile Gly Thr Ala
                405                 410                 415

Val Leu Glu Tyr Ile Thr Gln Gln Val Ala Pro Lys Asn Leu Asp Asn
            420                 425                 430

Pro ser Lys Lys Glu Gln Xaa Leu Ile Ala Lys Lys Thr Glu Lys Ala
        435                 440                 445

Lys Tyr Leu Ser Leu Glu Thr Ile Lys Leu Ala Leu Glu Glu Phe Asn
    450                 455                 460

Lys His Arg Asp Ile Asp Lys Gln cys Arg Phe Glu Glu Ile Leu Ala
465                 470                 475                 480

Asn Phe Ala Ala Ile Pro Met Ile Phe Asp Glu Ile Ala Gln Asn Lys
                485                 490                 495

Asp Asn Leu Ala Gln Ile Ser Xaa Lys Tyr Gln Asn Gln Gly Lys Lys
            500                 505                 510
```

-continued

```
Asp Leu Leu Gln Ala ser Ala Glu xaa Asp val Lys Ala Ile Lys Asp
            515                 520                 525
Leu Leu Asp Gln Thr Asn Asn Leu Leu His Xaa Leu Lys Ile Phe His
            530                 535                 540
Ile ser Gln Ser Glu Asp Lys Ala Asn Ile Leu Asp Lys Asp Glu His
545                 550                 555                 560
Phe Tyr Leu Val Phe Glu Glu Cys Tyr Phe Glu Leu Ala Asn Ile Val
                565                 570                 575
Pro Leu Tyr Asn Lys Ile Arg Asn Tyr Ile Thr Gln Lys Pro Tyr Ser
            580                 585                 590
Asp Glu Lys Phe Lys Leu Asn Phe Glu Asn Ser Thr Leu Ala Asn Gly
            595                 600                 605
Trp Asp Lys Asn Lys Glu Pro Asp Asn Thr Ala Ile Leu Phe Ile Lys
            610                 615                 620
Asp Asp Lys Tyr Tyr Leu Gly val Met Asn Lys Lys Asn Asn Lys Ile
625                 630                 635                 640
Phe Asp Asp Lys Ala Ile Lys Glu ASn Lys Gly Glu Gly Tyr Lys Lys
                645                 650                 655
Ile val Tyr Lys Leu Leu Pro Gly Ala Asn Lys Met Leu Pro Lys val
            660                 665                 670
Phe Phe Ser Ala Lys Ser Ile Lys Phe Tyr Asn Pro Ser Glu Asp Ile
            675                 680                 685
Leu Arg Ile Arg Asn His Ser Thr His Thr Lys Asn Gly Asn Pro Gln
            690                 695                 700
Lys Gly Tyr Glu Lys Phe Glu Phe Asn Ile Glu Asp cys Arg Lys Phe
705                 710                 715                 720
Ile Asp Phe Tyr Lys Glu Ser Ile Ser Lys His Pro Glu Trp Lys Asp
                725                 730                 735
Phe Gly Phe Arg Phe Ser Asp Thr Gln Arg Tyr Asn Ser Ile Asp Glu
            740                 745                 750
Phe Tyr Arg Glu val Glu Asn Gln Gly Tyr Lys Leu Thr Phe Glu Asn
            755                 760                 765
Ile Ser Glu Ser Tyr Ile Asp Ser Val Val Asn Gln Gly Lys Leu Tyr
            770                 775                 780
Leu Phe Gln Ile Tyr Asn Lys Asp Phe Ser Ala Tyr Ser Lys Gly Xaa
785                 790                 795                 800
Pro Asn Leu His Thr Leu Tyr Trp Lys Ala Leu Phe Asp Glu Arg Asn
                805                 810                 815
Leu Gln Asp Val Val Tyr Lys Leu Asn Gly Glu Ala Glu Leu Phe Tyr
            820                 825                 830
Arg Lys Gln Ser Ile Pro Lys Lys Ile Thr His Pro Ala Lys Glu Ala
            835                 840                 845
Ile Ala Asn Lys Asn Lys Asp Asn Pro Lys Lys Glu Ser Val Phe Glu
850                 855                 860
Tyr Asp Leu Ile Lys Asp Lys Arg Phe Thr Glu Asp Lys Phe Phe Phe
865                 870                 875                 880
His Cys Pro Ile Thr Ile Asn Phe Lys Ser Ser Gly Ala Asn Lys Phe
                885                 890                 895
Asn Asp Glu Ile Asn Leu Leu Leu Lys Glu Lys Ala Asn Asp Val His
            900                 905                 910
Ile Leu Ser Ile Asp Arg Gly Glu Arg His Leu Ala Tyr Tyr Thr Leu
            915                 920                 925
Val Asp Gly Lys Gly Asn Ile Ile Lys Gln Asp Thr Phe Asn Ile Ile
            930                 935                 940
```

-continued

```
Gly Asn Asp Arg Met Lys Thr Asn Tyr His Asp Lys Leu Ala Ala Ile
945                 950                 955                 960

Glu Lys Asp Arg Asp Ser Ala Arg Lys Asp Trp Lys Lys Ile Asn Asn
            965                 970                 975

Ile Lys Glu Met Lys Glu Gly Tyr Leu Ser Gln Val Val His Glu Ile
            980                 985                 990

Ala Lys Leu val Ile Glu Tyr Asn Ala Ile Val Val Phe Glu Asp Leu
            995                 1000                1005

Asn Phe Gly Phe Lys Arg Gly Arg Phe Lys Val Glu Lys Gln Val
        1010                1015                1020

Tyr Gln Lys Leu Glu Lys Met Leu Ile Glu Lys Leu Asn Tyr Leu
        1025                1030                1035

Val Phe Lys Asp Asn Glu Phe Asp Lys Thr Gly Gly Val Leu Arg
        1040                1045                1050

Ala Tyr Gln Leu Thr Ala Pro Phe Glu Thr Phe Lys Lys Met Gly
        1055                1060                1065

Lys Gln Thr Gly Ile Ile Tyr Tyr Val Pro Ala Gly Phe Thr Ser
        1070                1075                1080

Lys Ile Cys Pro Val Thr Gly Phe Val Asn Gln Leu Tyr Pro Lys
        1085                1090                1095

Tyr Glu Ser Val Ser Lys Ser Gln Glu Phe Phe Ser Lys Phe Asp
        1100                1105                1110

Lys Ile Cys Tyr Asn Leu Asp Lys Gly Tyr Phe Glu Phe Ser Phe
        1115                1120                1125

Asp Tyr Lys Asn Phe Gly Asp Lys Ala Ala Lys Gly Lys Trp Thr
        1130                1135                1140

Ile Ala Ser Phe Gly Ser Arg Leu Ile Asn Phe Arg Asn Ser Asp
        1145                1150                1155

Lys Asn His Asn Trp Asp Thr Arg Glu Val Tyr Pro Thr Lys Glu
        1160                1165                1170

Leu Glu Lys Leu Leu Lys Asp Tyr Ser Ile Glu Tyr Gly His Gly
        1175                1180                1185

Glu Cys Ile Lys Ala Ala Ile Cys Gly Glu Ser Asp Lys Lys Phe
        1190                1195                1200

Phe Ala Lys Leu Thr Ser Val Leu Asn Thr Ile Leu Gln Met Arg
        1205                1210                1215

Asn Ser Lys Thr Gly Thr Glu Leu Asp Tyr Leu Ile Ser Pro Val
        1220                1225                1230

Ala Asp Val Asn Gly Asn Phe Phe Asp Ser Arg Gln Ala Pro Lys
        1235                1240                1245

Asn Met Pro Gln Asp Ala Asp Ala Asn Gly Ala Tyr His Ile Gly
        1250                1255                1260

Leu Lys Gly Leu Met Leu Leu Asp Arg Ile Lys Asn Asn Gln Glu
        1265                1270                1275

Gly Lys Lys Leu Asn Leu Val Ile Lys Asn Glu Glu Tyr Phe Glu
        1280                1285                1290

Phe Val Gln Asn Arg Asn Asn Ser ser Lys Ile
        1295                1300
```

SEQUENCE LISTING

<160> NUMBER OF SEQ ID NOS: 36

<210> SEQ ID NO 1
<211> LENGTH: 1304
<212> TYPE: PRT
<213> ORGANISM: Artificial Sequence
<220> FEATURE:
<223> OTHER INFORMATION: Description of Artificial Sequence: Synthetic
      Cpf1 consensus sequence
<220> FEATURE:
<221> NAME/KEY: MOD_RES
<222> LOCATION: (439)..(439)
<223> OTHER INFORMATION: Any naturally occurring amino acid
<220> FEATURE:
<221> NAME/KEY: MOD_RES
<222> LOCATION: (504)..(504)
<223> OTHER INFORMATION: Any naturally occurring amino acid
<220> FEATURE:
<221> NAME/KEY: MOD_RES
<222> LOCATION: (521)..(521)
<223> OTHER INFORMATION: Any naturally occurring amino acid
<220> FEATURE:
<221> NAME/KEY: MOD_RES
<222> LOCATION: (539)..(539)
<223> OTHER INFORMATION: Any naturally occurring amino acid
<220> FEATURE:
<221> NAME/KEY: MOD_RES
<222> LOCATION: (800)..(800)
<223> OTHER INFORMATION: Any naturally occurring amino acid

<400> SEQUENCE: 1

Met Ser Ile Tyr Gln Glu Phe Val Asn Lys Tyr Ser Leu Ser Lys Thr
1               5                   10                  15

Leu Arg Phe Glu Leu Ile Pro Gln Gly Lys Thr Leu Glu Asn Ile Lys
            20                  25                  30

Ala Arg Gly Leu Ile Leu Asp Asp Glu Lys Arg Ala Lys Asp Tyr Lys
        35                  40                  45

Lys Ala Lys Gln Ile Ile Asp Lys Tyr His Gln Phe Phe Ile Glu Glu
    50                  55                  60

Ile Leu Ser Ser Val Cys Ile Ser Glu Asp Leu Leu Gln Asn Tyr Ser
65                  70                  75                  80

Asp Val Tyr Phe Lys Leu Lys Lys Ser Asp Asp Asn Leu Gln Lys
                85                  90                  95

Asp Phe Lys Ser Ala Lys Asp Thr Ile Lys Lys Gln Ile Ser Glu Tyr
            100                 105                 110

Ile Lys Asp Ser Glu Lys Phe Lys Asn Leu Phe Asn Gln Asn Leu Ile
        115                 120                 125

Asp Ala Lys Lys Gly Gln Glu Ser Asp Leu Ile Leu Trp Leu Lys Gln
    130                 135                 140

Ser Lys Asp Asn Gly Ile Glu Leu Phe Lys Ala Asn Ser Asp Ile Thr
145                 150                 155                 160

Asp Ile Asp Glu Ala Leu Glu Ile Ile Lys Ser Phe Lys Gly Trp Thr
                165                 170                 175

Thr Tyr Phe Lys Gly Phe His Glu Asn Arg Lys Asn Val Tyr Ser Ser
            180                 185                 190

Asp Asp Ile Pro Thr Ser Ile Ile Tyr Arg Ile Val Asp Asp Asn Leu
        195                 200                 205

Pro Lys Phe Leu Glu Asn Lys Ala Lys Tyr Glu Ser Leu Lys Asp Lys
    210                 215                 220

Ala Pro Glu Ala Ile Asn Tyr Glu Gln Ile Lys Lys Asp Leu Ala Glu
225                 230                 235                 240

Glu Leu Thr Phe Asp Ile Asp Tyr Lys Thr Ser Glu Val Asn Gln Arg

```
            245                 250                 255
Val Phe Ser Leu Asp Glu Val Phe Glu Ile Ala Asn Phe Asn Asn Tyr
            260                 265                 270
Leu Asn Gln Ser Gly Ile Thr Lys Phe Asn Thr Ile Ile Gly Gly Lys
            275                 280                 285
Phe Val Asn Gly Glu Asn Thr Lys Arg Lys Gly Ile Asn Glu Tyr Ile
            290                 295                 300
Asn Leu Tyr Ser Gln Gln Ile Asn Asp Lys Thr Leu Lys Lys Tyr Lys
305                 310                 315                 320
Met Ser Val Leu Phe Lys Gln Ile Leu Ser Asp Thr Glu Ser Lys Ser
                325                 330                 335
Phe Val Ile Asp Lys Leu Glu Asp Asp Ser Asp Val Val Thr Thr Met
                340                 345                 350
Gln Ser Phe Tyr Glu Gln Ile Ala Ala Phe Lys Thr Val Glu Glu Lys
                355                 360                 365
Ser Ile Lys Glu Thr Leu Ser Leu Leu Phe Asp Asp Leu Lys Ala Gln
            370                 375                 380
Lys Leu Asp Leu Ser Lys Ile Tyr Phe Lys Asn Asp Lys Ser Leu Thr
385                 390                 395                 400
Asp Leu Ser Gln Gln Val Phe Asp Asp Tyr Ser Val Ile Gly Thr Ala
                405                 410                 415
Val Leu Glu Tyr Ile Thr Gln Gln Val Ala Pro Lys Asn Leu Asp Asn
            420                 425                 430
Pro Ser Lys Lys Glu Gln Xaa Leu Ile Ala Lys Lys Thr Glu Lys Ala
            435                 440                 445
Lys Tyr Leu Ser Leu Glu Thr Ile Lys Leu Ala Leu Glu Glu Phe Asn
            450                 455                 460
Lys His Arg Asp Ile Asp Lys Gln Cys Arg Phe Glu Glu Ile Leu Ala
465                 470                 475                 480
Asn Phe Ala Ala Ile Pro Met Ile Phe Asp Glu Ile Ala Gln Asn Lys
                485                 490                 495
Asp Asn Leu Ala Gln Ile Ser Xaa Lys Tyr Gln Asn Gln Gly Lys Lys
            500                 505                 510
Asp Leu Leu Gln Ala Ser Ala Glu Xaa Asp Val Lys Ala Ile Lys Asp
            515                 520                 525
Leu Leu Asp Gln Thr Asn Asn Leu Leu His Xaa Leu Lys Ile Phe His
            530                 535                 540
Ile Ser Gln Ser Glu Asp Lys Ala Asn Ile Leu Asp Lys Asp Glu His
545                 550                 555                 560
Phe Tyr Leu Val Phe Glu Glu Cys Tyr Phe Glu Leu Ala Asn Ile Val
                565                 570                 575
Pro Leu Tyr Asn Lys Ile Arg Asn Tyr Ile Thr Gln Lys Pro Tyr Ser
            580                 585                 590
Asp Glu Lys Phe Lys Leu Asn Phe Glu Asn Ser Thr Leu Ala Asn Gly
            595                 600                 605
Trp Asp Lys Asn Lys Glu Pro Asp Asn Thr Ala Ile Leu Phe Ile Lys
            610                 615                 620
Asp Asp Lys Tyr Tyr Leu Gly Val Met Asn Lys Lys Asn Asn Lys Ile
625                 630                 635                 640
Phe Asp Asp Lys Ala Ile Lys Glu Asn Lys Gly Glu Gly Tyr Lys Lys
                645                 650                 655
Ile Val Tyr Lys Leu Leu Pro Gly Ala Asn Lys Met Leu Pro Lys Val
            660                 665                 670
```

```
Phe Phe Ser Ala Lys Ser Ile Lys Phe Tyr Asn Pro Ser Glu Asp Ile
            675                 680                 685

Leu Arg Ile Arg Asn His Ser Thr His Thr Lys Asn Gly Asn Pro Gln
    690                 695                 700

Lys Gly Tyr Glu Lys Phe Glu Phe Asn Ile Glu Asp Cys Arg Lys Phe
705                 710                 715                 720

Ile Asp Phe Tyr Lys Glu Ser Ile Ser Lys His Pro Glu Trp Lys Asp
                725                 730                 735

Phe Gly Phe Arg Phe Ser Asp Thr Gln Arg Tyr Asn Ser Ile Asp Glu
            740                 745                 750

Phe Tyr Arg Glu Val Glu Asn Gln Gly Tyr Lys Leu Thr Phe Glu Asn
            755                 760                 765

Ile Ser Glu Ser Tyr Ile Asp Ser Val Val Asn Gln Gly Lys Leu Tyr
    770                 775                 780

Leu Phe Gln Ile Tyr Asn Lys Asp Phe Ser Ala Tyr Ser Lys Gly Xaa
785                 790                 795                 800

Pro Asn Leu His Thr Leu Tyr Trp Lys Ala Leu Phe Asp Glu Arg Asn
                805                 810                 815

Leu Gln Asp Val Val Tyr Lys Leu Asn Gly Glu Ala Glu Leu Phe Tyr
            820                 825                 830

Arg Lys Gln Ser Ile Pro Lys Lys Ile Thr His Pro Ala Lys Glu Ala
            835                 840                 845

Ile Ala Asn Lys Asn Lys Asp Asn Pro Lys Lys Glu Ser Val Phe Glu
850                 855                 860

Tyr Asp Leu Ile Lys Asp Lys Arg Phe Thr Glu Asp Lys Phe Phe Phe
865                 870                 875                 880

His Cys Pro Ile Thr Ile Asn Phe Lys Ser Ser Gly Ala Asn Lys Phe
                885                 890                 895

Asn Asp Glu Ile Asn Leu Leu Leu Lys Glu Lys Ala Asn Asp Val His
                900                 905                 910

Ile Leu Ser Ile Asp Arg Gly Glu Arg His Leu Ala Tyr Tyr Thr Leu
    915                 920                 925

Val Asp Gly Lys Gly Asn Ile Ile Lys Gln Asp Thr Phe Asn Ile Ile
    930                 935                 940

Gly Asn Asp Arg Met Lys Thr Asn Tyr His Asp Lys Leu Ala Ala Ile
945                 950                 955                 960

Glu Lys Asp Arg Asp Ser Ala Arg Lys Asp Trp Lys Lys Ile Asn Asn
                965                 970                 975

Ile Lys Glu Met Lys Glu Gly Tyr Leu Ser Gln Val Val His Glu Ile
                980                 985                 990

Ala Lys Leu Val Ile Glu Tyr Asn Ala Ile Val Val Phe Glu Asp Leu
            995                 1000                1005

Asn Phe Gly Phe Lys Arg Gly Arg Phe Lys Val Glu Lys Gln Val
    1010                1015                1020

Tyr Gln Lys Leu Glu Lys Met Leu Ile Glu Lys Leu Asn Tyr Leu
    1025                1030                1035

Val Phe Lys Asp Asn Glu Phe Asp Lys Thr Gly Gly Val Leu Arg
    1040                1045                1050

Ala Tyr Gln Leu Thr Ala Pro Phe Glu Thr Phe Lys Lys Met Gly
    1055                1060                1065

Lys Gln Thr Gly Ile Ile Tyr Tyr Val Pro Ala Gly Phe Thr Ser
    1070                1075                1080
```

Lys Ile Cys Pro Val Thr Gly Phe Val Asn Gln Leu Tyr Pro Lys
    1085                1090                1095

Tyr Glu Ser Val Ser Lys Ser Gln Glu Phe Phe Ser Lys Phe Asp
    1100                1105                1110

Lys Ile Cys Tyr Asn Leu Asp Lys Gly Tyr Phe Glu Phe Ser Phe
    1115                1120                1125

Asp Tyr Lys Asn Phe Gly Asp Lys Ala Ala Lys Gly Lys Trp Thr
    1130                1135                1140

Ile Ala Ser Phe Gly Ser Arg Leu Ile Asn Phe Arg Asn Ser Asp
    1145                1150                1155

Lys Asn His Asn Trp Asp Thr Arg Glu Val Tyr Pro Thr Lys Glu
    1160                1165                1170

Leu Glu Lys Leu Leu Lys Asp Tyr Ser Ile Glu Tyr Gly His Gly
    1175                1180                1185

Glu Cys Ile Lys Ala Ala Ile Cys Gly Glu Ser Asp Lys Lys Phe
    1190                1195                1200

Phe Ala Lys Leu Thr Ser Val Leu Asn Thr Ile Leu Gln Met Arg
    1205                1210                1215

Asn Ser Lys Thr Gly Thr Glu Leu Asp Tyr Leu Ile Ser Pro Val
    1220                1225                1230

Ala Asp Val Asn Gly Asn Phe Phe Asp Ser Arg Gln Ala Pro Lys
    1235                1240                1245

Asn Met Pro Gln Asp Ala Asp Ala Asn Gly Ala Tyr His Ile Gly
    1250                1255                1260

Leu Lys Gly Leu Met Leu Leu Asp Arg Ile Lys Asn Asn Gln Glu
    1265                1270                1275

Gly Lys Lys Leu Asn Leu Val Ile Lys Asn Glu Glu Tyr Phe Glu
    1280                1285                1290

Phe Val Gln Asn Arg Asn Asn Ser Ser Lys Ile
    1295                1300

<210> SEQ ID NO 2
<211> LENGTH: 5
<212> TYPE: PRT
<213> ORGANISM: Artificial Sequence
<220> FEATURE:
<223> OTHER INFORMATION: Description of Artificial Sequence: Synthetic
      Residues 786 - 791 of Cpf1 consensus sequence (SEQ ID NO: 1)

<400> SEQUENCE: 2

Phe Gln Ile Tyr Asn
1               5

<210> SEQ ID NO 3
<211> LENGTH: 6
<212> TYPE: PRT
<213> ORGANISM: Artificial Sequence
<220> FEATURE:
<223> OTHER INFORMATION: Description of Artificial Sequence: Synthetic
      Residues 786 - 791 of Cpf1 consensus sequence (SEQ ID NO: 1)

<400> SEQUENCE: 3

Phe Gln Ile Tyr Asn Lys
1               5

<210> SEQ ID NO 4
<211> LENGTH: 7
<212> TYPE: PRT
<213> ORGANISM: Artificial Sequence
<220> FEATURE:

<223> OTHER INFORMATION: Description of Artificial Sequence: Synthetic
      Residues 786 - 792 of Cpf1 consensus sequence (SEQ ID NO: 1)

<400> SEQUENCE: 4

Phe Gln Ile Tyr Asn Lys Asp
1               5

<210> SEQ ID NO 5
<211> LENGTH: 14
<212> TYPE: PRT
<213> ORGANISM: Artificial Sequence
<220> FEATURE:
<223> OTHER INFORMATION: Description of Artificial Sequence: Synthetic
      Residues 781 - 794 of Cpf1 consensus sequence (SEQ ID NO: 1)
<220> FEATURE:
<221> NAME/KEY: MOD_RES
<222> LOCATION: (1)..(1)
<223> OTHER INFORMATION: Gly or Lys
<220> FEATURE:
<221> NAME/KEY: MOD_RES
<222> LOCATION: (2)..(2)
<223> OTHER INFORMATION: Lys, Ser or Asp
<220> FEATURE:
<221> NAME/KEY: MOD_RES
<222> LOCATION: (3)..(3)
<223> OTHER INFORMATION: Leu or Ile
<220> FEATURE:
<221> NAME/KEY: MOD_RES
<222> LOCATION: (4)..(4)
<223> OTHER INFORMATION: Tyr or Phe
<220> FEATURE:
<221> NAME/KEY: MOD_RES
<222> LOCATION: (5)..(5)
<223> OTHER INFORMATION: Leu or Met
<220> FEATURE:
<221> NAME/KEY: MOD_RES
<222> LOCATION: (13)..(13)
<223> OTHER INFORMATION: Phe or Tyr
<220> FEATURE:
<221> NAME/KEY: MOD_RES
<222> LOCATION: (14)..(14)
<223> OTHER INFORMATION: Ser, Ala or Val

<400> SEQUENCE: 5

Xaa Xaa Xaa Xaa Xaa Phe Gln Ile Tyr Asn Lys Asp Xaa Xaa
1               5                   10

<210> SEQ ID NO 6
<211> LENGTH: 14
<212> TYPE: PRT
<213> ORGANISM: Artificial Sequence
<220> FEATURE:
<223> OTHER INFORMATION: Description of Artificial Sequence: Synthetic
      Residues 781 - 794 of Cpf1 consensus sequence (SEQ ID NO: 1)

<400> SEQUENCE: 6

Gly Lys Leu Tyr Leu Phe Gln Ile Tyr Asn Lys Asp Phe Ser
1               5                   10

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      RuvC domain of catalytically inactive Cpf1
<220> FEATURE:
<221> NAME/KEY: MOD_RES
<222> LOCATION: (1)..(1)
<223> OTHER INFORMATION: Gly or Ser

<400> SEQUENCE: 7

```
Xaa Ile Asp Arg Gly Glu Arg
1               5

<210> SEQ ID NO 8
<211> LENGTH: 6
<212> TYPE: PRT
<213> ORGANISM: Artificial Sequence
<220> FEATURE:
<223> OTHER INFORMATION: Description of Artificial Sequence: Synthetic
      RuvC domain of catalytically inactive Cpf1

<400> SEQUENCE: 8

Asp Ala Asn Gly Ala Tyr
1               5

<210> SEQ ID NO 9
<211> LENGTH: 4
<212> TYPE: PRT
<213> ORGANISM: Artificial Sequence
<220> FEATURE:
<223> OTHER INFORMATION: Description of Artificial Sequence: Synthetic
      RuvC domain of catalytically inactive Cpf1
<220> FEATURE:
<221> NAME/KEY: MOD_RES
<222> LOCATION: (2)..(2)
<223> OTHER INFORMATION: Asp, Asn or Glu

<400> SEQUENCE: 9

Glu Xaa Leu Asn
1

<210> SEQ ID NO 10
<211> LENGTH: 4
<212> TYPE: PRT
<213> ORGANISM: Artificial Sequence
<220> FEATURE:
<223> OTHER INFORMATION: Description of Artificial Sequence: Synthetic
      RuvC domain of catalytically inactive Cpf1

<400> SEQUENCE: 10

Glu Asp Leu Asn
1

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Synthetic
      RuvC domain

<400> SEQUENCE: 11

Ser Ile Asp Arg Gly Glu Arg
1               5

<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence: Synthetic
      RuvC domain

<400> SEQUENCE: 12

Gly Ile Asp Arg Gly Glu Arg
1               5

<210> SEQ ID NO 13
```

```
<211> LENGTH: 4
<212> TYPE: PRT
<213> ORGANISM: Artificial Sequence
<220> FEATURE:
<223> OTHER INFORMATION: Description of Artificial Sequence: Synthetic
      RuvC domain

<400> SEQUENCE: 13

Glu Asn Leu Asn
1

<210> SEQ ID NO 14
<211> LENGTH: 4
<212> TYPE: PRT
<213> ORGANISM: Artificial Sequence
<220> FEATURE:
<223> OTHER INFORMATION: Description of Artificial Sequence: Synthetic
      RuvCdomain

<400> SEQUENCE: 14

Glu Glu Leu Asn
1

<210> SEQ ID NO 15
<211> LENGTH: 19
<212> TYPE: PRT
<213> ORGANISM: Artificial Sequence
<220> FEATURE:
<223> OTHER INFORMATION: Description of Artificial Sequence: Synthetic
      Arginine-rich motif
<220> FEATURE:
<221> NAME/KEY: MOD_RES
<222> LOCATION: (1)..(1)
<223> OTHER INFORMATION: Asp or Asn
<220> FEATURE:
<221> NAME/KEY: MOD_RES
<222> LOCATION: (3)..(3)
<223> OTHER INFORMATION: Arg, Gln or His
<220> FEATURE:
<221> NAME/KEY: MOD_RES
<222> LOCATION: (4)..(4)
<223> OTHER INFORMATION: Lys, Glu, Ser or Asp
<220> FEATURE:
<221> NAME/KEY: MOD_RES
<222> LOCATION: (5)..(5)
<223> OTHER INFORMATION: Ala, Lys or Leu
<220> FEATURE:
<221> NAME/KEY: MOD_RES
<222> LOCATION: (7)..(7)
<223> OTHER INFORMATION: Asp, Asn or Ala
<220> FEATURE:
<221> NAME/KEY: MOD_RES
<222> LOCATION: (8)..(8)
<223> OTHER INFORMATION: Val, Asn, Gln, Lys or Ala
<220> FEATURE:
<221> NAME/KEY: MOD_RES
<222> LOCATION: (9)..(9)
<223> OTHER INFORMATION: Arg, Lys or Ile
<220> FEATURE:
<221> NAME/KEY: MOD_RES
<222> LOCATION: (11)..(11)
<223> OTHER INFORMATION: Tyr, Lys or Ile
<220> FEATURE:
<221> NAME/KEY: MOD_RES
<222> LOCATION: (12)..(12)
<223> OTHER INFORMATION: Asp or Glu
<220> FEATURE:
<221> NAME/KEY: MOD_RES
<222> LOCATION: (13)..(13)
<223> OTHER INFORMATION: Asn, Arg or Met
<220> FEATURE:
<221> NAME/KEY: MOD_RES
<222> LOCATION: (14)..(14)
<223> OTHER INFORMATION: Lys, Val, Phe or Asp
<220> FEATURE:
```

```
<221> NAME/KEY: MOD_RES
<222> LOCATION: (15)..(15)
<223> OTHER INFORMATION: Glu, Ala, Asp or Ser
<220> FEATURE:
<221> NAME/KEY: MOD_RES
<222> LOCATION: (18)..(18)
<223> OTHER INFORMATION: Arg, Gln or Lys
<220> FEATURE:
<221> NAME/KEY: MOD_RES
<222> LOCATION: (19)..(19)
<223> OTHER INFORMATION: Asn, Ala, Ser or Asp

<400> SEQUENCE: 15

Xaa Tyr Xaa Xaa Xaa Leu Xaa Xaa Xaa Glu Xaa Xaa Xaa Xaa Xaa Ala
1               5                   10                  15

Arg Xaa Xaa

<210> SEQ ID NO 16
<211> LENGTH: 19
<212> TYPE: PRT
<213> ORGANISM: Artificial Sequence
<220> FEATURE:
<223> OTHER INFORMATION: Description of Artificial Sequence: Synthetic
      Arginine-rich motif

<400> SEQUENCE: 16

Asp Tyr Arg Lys Ala Leu Asp Val Arg Glu Tyr Asp Asn Lys Glu Ala
1               5                   10                  15

Arg Arg Asn

<210> SEQ ID NO 17
<211> LENGTH: 19
<212> TYPE: PRT
<213> ORGANISM: Artificial Sequence
<220> FEATURE:
<223> OTHER INFORMATION: Description of Artificial Sequence: Synthetic
      Arginine-rich motif

<400> SEQUENCE: 17

Asp Tyr Gln Lys Lys Leu Asp Asn Arg Glu Lys Glu Arg Val Ala Ala
1               5                   10                  15

Arg Gln Ala

<210> SEQ ID NO 18
<211> LENGTH: 19
<212> TYPE: PRT
<213> ORGANISM: Artificial Sequence
<220> FEATURE:
<223> OTHER INFORMATION: Description of Artificial Sequence: Synthetic
      Arginine-rich motif

<400> SEQUENCE: 18

Asp Tyr Arg Glu Lys Leu Asn Gln Arg Glu Ile Glu Met Lys Asp Ala
1               5                   10                  15

Arg Gln Ser

<210> SEQ ID NO 19
<211> LENGTH: 19
<212> TYPE: PRT
<213> ORGANISM: Artificial Sequence
<220> FEATURE:
<223> OTHER INFORMATION: Description of Artificial Sequence: Synthetic
      Arginine-rich motif
```

-continued

<400> SEQUENCE: 19

Asp Tyr His Ser Leu Leu Asp Lys Lys Glu Lys Glu Arg Phe Glu Ala
1               5                   10                  15

Arg Gln Asn

<210> SEQ ID NO 20
<211> LENGTH: 19
<212> TYPE: PRT
<213> ORGANISM: Artificial Sequence
<220> FEATURE:
<223> OTHER INFORMATION: Description of Artificial Sequence: Synthetic
      Arginine-rich motif

<400> SEQUENCE: 20

Asn Tyr His Asp Lys Leu Ala Ala Ile Glu Lys Asp Arg Asp Ser Ala
1               5                   10                  15

Arg Lys Asp

<210> SEQ ID NO 21
<211> LENGTH: 29
<212> TYPE: DNA
<213> ORGANISM: Francisella novicida

<400> SEQUENCE: 21
agattaaaag gtaattctat cttgttgag                                   29

<210> SEQ ID NO 22
<211> LENGTH: 45
<212> TYPE: DNA
<213> ORGANISM: Francisella novicida

<400> SEQUENCE: 22
ataatttaag attaaaaggt aattctattt tgttgagatc tgagc                 45

<210> SEQ ID NO 23
<211> LENGTH: 26
<212> TYPE: DNA
<213> ORGANISM: Francisella novicida

<400> SEQUENCE: 23
tagcgattta tgaaggtcat tttttt                                      26

<210> SEQ ID NO 24
<211> LENGTH: 42
<212> TYPE: DNA
<213> ORGANISM: Francisella novicida

<400> SEQUENCE: 24
ctaaattata gcgatttatg aaggtcattt ttttaaaaag tt                    42

<210> SEQ ID NO 25
<211> LENGTH: 29
<212> TYPE: DNA
<213> ORGANISM: Francisella novicida

<400> SEQUENCE: 25
atggattatt acttaactgg agtgtttac                                   29

<210> SEQ ID NO 26
<211> LENGTH: 45
<212> TYPE: DNA
<213> ORGANISM: Francisella novicida

<400> SEQUENCE: 26
aatgttcaat ggattattac ttaattggag tgtctacgtc gatgg 45

<210> SEQ ID NO 27
<211> LENGTH: 28
<212> TYPE: DNA
<213> ORGANISM: Francisella novicida

<400> SEQUENCE: 27
gccacaaata ctacaaaaaa taacttaa 28

<210> SEQ ID NO 28
<211> LENGTH: 44
<212> TYPE: DNA
<213> ORGANISM: Francisella novicida

<400> SEQUENCE: 28 atttttggc tccaaatact acaaaaaata acttaaactt tgaa 44

<210> SEQ ID NO 29
<211> LENGTH: 32
<212> TYPE: DNA
<213> ORGANISM: Francisella novicida

<400> SEQUENCE: 29
attgtcaaaa cataagcagc tgcttcaaat at 32

<210> SEQ ID NO 30
<211> LENGTH: 48
<212> TYPE: DNA
<213> ORGANISM: Francisella novicida

<400> SEQUENCE: 30
ggtcttttac tgttattaca taagcagccg cttcaaatat cttagcaa 48

<210> SEQ ID NO 31
<211> LENGTH: 10
<212> TYPE: PRT
<213> ORGANISM: Artificial Sequence
<220> FEATURE:
<223> OTHER INFORMATION: Description of Artificial Sequence: Synthetic
isolated polypeptide or fragment thereof having a
nuclease activity

<400> SEQUENCE: 31

Tyr Leu Phe Gln Ile Tyr Asn Lys Asp Phe
1 5 10

<210> SEQ ID NO 32
<211> LENGTH: 1184
<212> TYPE: PRT
<213> ORGANISM: Methanomethylophilus alvus

<400> SEQUENCE: 32

Met Asp Ala Lys Glu Phe Thr Gly Gln Tyr Pro Leu Ser Lys Thr Leu
1 5 10 15

Arg Phe Glu Leu Arg Pro Ile Gly Arg Thr Trp Asp Asn Leu Glu Ala
20 25 30

Ser Gly Tyr Leu Ala Glu Asp Arg His Arg Ala Glu Cys Tyr Pro Arg
35 40 45

Ala Lys Glu Leu Leu Asp Asp Asn His Arg Ala Phe Leu Asn Arg Val
50 55 60

```
Leu Pro Gln Ile Gln Asp Ala Asp Gly Tyr Lys Gly Leu Phe Ala Lys
 65                  70                  75                  80

Pro Ala Leu Asp Glu Ala Met Lys Ile Ala Lys Glu Asn Gly Asn Glu
                 85                  90                  95

Ser Asp Ile Glu Val Leu Glu Ala Phe Asn Gly Phe Ser Val Tyr Phe
            100                 105                 110

Thr Gly Tyr His Glu Ser Arg Glu Asn Ile Tyr Ser Asp Glu Asp Met
        115                 120                 125

Val Ser Val Ala Tyr Arg Ile Thr Glu Asp Asn Phe Pro Arg Phe Val
    130                 135                 140

Ser Asn Ala Leu Ile Phe Asp Lys Leu Asn Glu Ser His Pro Asp Ile
145                 150                 155                 160

Ile Ser Glu Val Ser Gly Asn Leu Gly Val Asp Asp Ile Gly Lys Tyr
                165                 170                 175

Phe Asp Val Ser Asn Tyr Asn Phe Leu Ser Gln Ala Gly Ile Asp
            180                 185                 190

Asp Tyr Asn His Ile Ile Gly Gly His Thr Thr Glu Asp Gly Leu Ile
        195                 200                 205

Gln Ala Phe Asn Val Val Leu Asn Leu Arg His Gln Lys Asp Pro Gly
    210                 215                 220

Phe Glu Lys Ile Gln Phe Lys Gln Leu Tyr Lys Gln Ile Leu Ser Val
225                 230                 235                 240

Arg Thr Ser Lys Ser Tyr Ile Pro Lys Gln Phe Asp Asn Ser Lys Glu
                245                 250                 255

Met Val Asp Cys Ile Cys Asp Tyr Val Ser Lys Ile Glu Lys Ser Glu
            260                 265                 270

Thr Val Glu Arg Ala Leu Lys Leu Val Arg Asn Ile Ser Ser Phe Asp
        275                 280                 285

Leu Arg Gly Ile Phe Val Asn Lys Lys Asn Leu Arg Ile Leu Ser Asn
290                 295                 300

Lys Leu Ile Gly Asp Trp Asp Ala Ile Glu Thr Ala Leu Met His Ser
305                 310                 315                 320

Ser Ser Ser Glu Asn Asp Lys Lys Ser Val Tyr Asp Ser Ala Glu Ala
                325                 330                 335

Phe Thr Leu Asp Asp Ile Phe Ser Ser Val Lys Lys Phe Ser Asp Ala
            340                 345                 350

Ser Ala Glu Asp Ile Gly Asn Arg Ala Glu Asp Ile Cys Arg Val Ile
        355                 360                 365

Ser Glu Thr Ala Pro Phe Ile Asn Asp Leu Arg Ala Val Asp Leu Asp
    370                 375                 380

Ser Leu Asn Asp Asp Gly Tyr Glu Ala Ala Val Ser Lys Ile Arg Glu
385                 390                 395                 400

Ser Leu Glu Pro Tyr Met Asp Leu Phe His Glu Leu Glu Ile Phe Ser
                405                 410                 415

Val Gly Asp Glu Phe Pro Lys Cys Ala Ala Phe Tyr Ser Glu Leu Glu
            420                 425                 430

Glu Val Ser Glu Gln Leu Ile Glu Ile Pro Leu Phe Asn Lys Ala
        435                 440                 445

Arg Ser Phe Cys Thr Arg Lys Arg Tyr Ser Thr Asp Lys Ile Lys Val
    450                 455                 460

Asn Leu Lys Phe Pro Thr Leu Ala Asp Gly Trp Asp Leu Asn Lys Glu
465                 470                 475                 480
```

```
Arg Asp Asn Lys Ala Ile Leu Arg Lys Asp Gly Lys Tyr Tyr Leu
            485                 490                 495

Ala Ile Leu Asp Met Lys Lys Asp Leu Ser Ser Ile Arg Thr Ser Asp
                500                 505                 510

Glu Asp Glu Ser Ser Phe Glu Lys Met Glu Tyr Lys Leu Leu Pro Ser
            515                 520                 525

Pro Val Lys Met Leu Pro Lys Ile Phe Val Lys Ser Lys Ala Ala Lys
            530                 535                 540

Glu Lys Tyr Gly Leu Thr Asp Arg Met Leu Glu Cys Tyr Asp Lys Gly
545                 550                 555                 560

Met His Lys Ser Gly Ser Ala Phe Asp Leu Gly Phe Cys His Glu Leu
                565                 570                 575

Ile Asp Tyr Tyr Lys Arg Cys Ile Ala Glu Tyr Pro Gly Trp Asp Val
            580                 585                 590

Phe Asp Phe Lys Phe Arg Glu Thr Ser Asp Tyr Gly Ser Met Lys Glu
            595                 600                 605

Phe Asn Glu Asp Val Ala Gly Ala Gly Tyr Tyr Met Ser Leu Arg Lys
            610                 615                 620

Ile Pro Cys Ser Glu Val Tyr Arg Leu Leu Asp Glu Lys Ser Ile Tyr
625                 630                 635                 640

Leu Phe Gln Ile Tyr Asn Lys Asp Tyr Ser Glu Asn Ala His Gly Asn
                645                 650                 655

Lys Asn Met His Thr Met Tyr Trp Glu Gly Leu Phe Ser Pro Gln Asn
                660                 665                 670

Leu Glu Ser Pro Val Phe Lys Leu Ser Gly Gly Ala Glu Leu Phe Phe
            675                 680                 685

Arg Lys Ser Ser Ile Pro Asn Asp Ala Lys Thr Val His Pro Lys Gly
            690                 695                 700

Ser Val Leu Val Pro Arg Asn Asp Val Asn Gly Arg Arg Ile Pro Asp
705                 710                 715                 720

Ser Ile Tyr Arg Glu Leu Thr Arg Tyr Phe Asn Arg Gly Asp Cys Arg
                725                 730                 735

Ile Ser Asp Glu Ala Lys Ser Tyr Leu Asp Lys Val Lys Thr Lys Lys
            740                 745                 750

Ala Asp His Asp Ile Val Lys Asp Arg Arg Phe Thr Val Asp Lys Met
            755                 760                 765

Met Phe His Val Pro Ile Ala Met Asn Phe Lys Ala Ile Ser Lys Pro
            770                 775                 780

Asn Leu Asn Lys Lys Val Ile Asp Gly Ile Ile Asp Asp Gln Asp Leu
785                 790                 795                 800

Lys Ile Ile Gly Ile Asp Arg Gly Glu Arg Asn Leu Ile Tyr Val Thr
                805                 810                 815

Met Val Asp Arg Lys Gly Asn Ile Leu Tyr Gln Asp Ser Leu Asn Ile
                820                 825                 830

Leu Asn Gly Tyr Asp Tyr Arg Lys Ala Leu Asp Val Arg Glu Tyr Asp
            835                 840                 845

Asn Lys Glu Ala Arg Arg Asn Trp Thr Lys Val Glu Gly Ile Arg Lys
850                 855                 860

Met Lys Glu Gly Tyr Leu Ser Leu Ala Val Ser Lys Leu Ala Asp Met
865                 870                 875                 880

Ile Ile Glu Asn Asn Ala Ile Ile Val Met Glu Asp Leu Asn His Gly
                885                 890                 895

Phe Lys Ala Gly Arg Ser Lys Ile Glu Lys Gln Val Tyr Gln Lys Phe
```

```
                900             905             910
        Glu Ser Met Leu Ile Asn Lys Leu Gly Tyr Met Val Leu Lys Asp Lys
                    915             920             925

Ser Ile Asp Gln Ser Gly Gly Ala Leu His Gly Tyr Gln Leu Ala Asn
                        930             935             940

His Val Thr Thr Leu Ala Ser Val Gly Lys Gln Cys Gly Val Ile Phe
        945             950             955             960

Tyr Ile Pro Ala Ala Phe Thr Ser Lys Ile Asp Pro Thr Thr Gly Phe
                        965             970             975

Ala Asp Leu Phe Ala Leu Ser Asn Val Lys Asn Val Ala Ser Met Arg
                        980             985             990

Glu Phe Phe Ser Lys Met Lys Ser Val Ile Tyr Asp Lys Ala Glu Gly
                    995             1000            1005

Lys Phe Ala Phe Thr Phe Asp Tyr Leu Asp Tyr Asn Val Lys Ser
                1010            1015            1020

Glu Cys Gly Arg Thr Leu Trp Thr Val Tyr Thr Val Gly Glu Arg
                1025            1030            1035

Phe Thr Tyr Ser Arg Val Asn Arg Glu Tyr Val Arg Lys Val Pro
                1040            1045            1050

Thr Asp Ile Ile Tyr Asp Ala Leu Gln Lys Ala Gly Ile Ser Val
                1055            1060            1065

Glu Gly Asp Leu Arg Asp Arg Ile Ala Glu Ser Asp Gly Asp Thr
                1070            1075            1080

Leu Lys Ser Ile Phe Tyr Ala Phe Lys Tyr Ala Leu Asp Met Arg
                1085            1090            1095

Val Glu Asn Arg Glu Glu Asp Tyr Ile Gln Ser Pro Val Lys Asn
                1100            1105            1110

Ala Ser Gly Glu Phe Phe Cys Ser Lys Asn Ala Gly Lys Ser Leu
                1115            1120            1125

Pro Gln Asp Ser Asp Ala Asn Gly Ala Tyr Asn Ile Ala Leu Lys
                1130            1135            1140

Gly Ile Leu Gln Leu Arg Met Leu Ser Glu Gln Tyr Asp Pro Asn
                1145            1150            1155

Ala Glu Ser Ile Arg Leu Pro Leu Ile Thr Asn Lys Ala Trp Leu
                1160            1165            1170

Thr Phe Met Gln Ser Gly Met Lys Thr Trp Lys
                1175            1180

<210> SEQ ID NO 33
<211> LENGTH: 1265
<212> TYPE: PRT
<213> ORGANISM: Acidaminococcus sp. BV3L6 8

<400> SEQUENCE: 33

Met Thr Gln Phe Glu Gly Phe Thr Asn Leu Tyr Gln Val Ser Lys Thr
1               5                   10                  15

Leu Arg Phe Glu Leu Ile Pro Gln Gly Lys Thr Leu Lys His Ile Gln
                20                  25                  30

Glu Gln Gly Phe Ile Glu Glu Asp Lys Ala Arg Asn Asp His Tyr Lys
            35                  40                  45

Glu Leu Lys Pro Ile Ile Asp Arg Ile Tyr Lys Thr Tyr Ala Asp Gln
        50                  55                  60

Cys Leu Gln Leu Val Gly Arg Thr Asp Asn Leu Thr Asp Ala Ile Asn
65                  70                  75                  80
```

```
Lys Arg His Ala Glu Ile Tyr Lys Gly Leu Phe Lys Ala Glu Leu Phe
                85                  90                  95

Asn Gly Lys Val Leu Lys Gln Leu Gly Thr Val Thr Thr Thr Glu His
            100                 105                 110

Glu Asn Ala Leu Leu Arg Ser Phe Asp Lys Phe Thr Thr Tyr Phe Ser
            115                 120                 125

Gly Phe Tyr Glu Asn Arg Lys Asn Val Phe Ser Ala Glu Asp Ile Ser
        130                 135                 140

Thr Ala Ile Pro His Arg Ile Val Gln Asp Asn Phe Pro Lys Phe Lys
145                 150                 155                 160

Glu Asn Cys His Ile Phe Thr Arg Leu Ile Thr Ala Val Pro Ser Leu
                165                 170                 175

Arg Glu His Phe Glu Asn Val Lys Lys Ala Ile Gly Ile Phe Val Ser
                180                 185                 190

Thr Ser Ile Glu Glu Val Phe Ser Phe Pro Phe Tyr Asn Gln Leu Leu
        195                 200                 205

Thr Gln Thr Gln Ile Asp Leu Tyr Asn Gln Leu Leu Gly Gly Ile Ser
        210                 215                 220

Arg Glu Ala Gly Thr Glu Lys Ile Lys Gly Leu Asn Glu Val Leu Asn
225                 230                 235                 240

Leu Ala Ile Gln Lys Asn Asp Glu Thr Ala His Ile Ile Ala Ser Leu
                245                 250                 255

Pro His Arg Phe Ile Pro Leu Phe Lys Gln Ile Leu Ser Asp Arg Asn
                260                 265                 270

Thr Leu Ser Phe Ile Leu Glu Glu Phe Lys Ser Asp Glu Glu Val Ile
        275                 280                 285

Gln Ser Phe Cys Lys Tyr Lys Thr Leu Leu Arg Asn Glu Asn Val Leu
        290                 295                 300

Glu Thr Ala Glu Ala Leu Phe Asn Glu Leu Asn Ser Ile Asp Leu Thr
305                 310                 315                 320

His Ile Phe Ile Ser His Lys Lys Leu Glu Thr Ile Ser Ser Ala Leu
                325                 330                 335

Cys Asp His Trp Asp Thr Leu Arg Asn Ala Leu Tyr Glu Arg Arg Ile
                340                 345                 350

Ser Glu Leu Thr Gly Lys Ile Thr Lys Ser Ala Lys Glu Lys Val Gln
        355                 360                 365

Arg Ser Leu Lys His Glu Asp Ile Asn Leu Gln Glu Ile Ile Ser Ala
        370                 375                 380

Ala Gly Lys Glu Leu Ser Glu Ala Phe Lys Gln Lys Thr Ser Glu Ile
385                 390                 395                 400

Leu Ser His Ala His Ala Ala Leu Asp Gln Pro Leu Pro Thr Thr Leu
                405                 410                 415

Lys Lys Gln Glu Glu Lys Glu Ile Leu Lys Ser Gln Leu Asp Ser Leu
                420                 425                 430

Leu Gly Leu Tyr His Leu Leu Asp Trp Phe Ala Val Asp Glu Ser Asn
            435                 440                 445

Glu Val Asp Pro Glu Phe Ser Ala Arg Leu Thr Gly Ile Lys Leu Glu
            450                 455                 460

Met Glu Pro Ser Leu Ser Phe Tyr Asn Lys Ala Arg Asn Tyr Ala Thr
465                 470                 475                 480

Lys Lys Pro Tyr Ser Val Glu Lys Phe Lys Leu Asn Phe Gln Met Pro
            485                 490                 495

Thr Leu Ala Ser Gly Trp Asp Val Asn Lys Glu Lys Asn Asn Gly Ala
```

```
                500             505             510
Ile Leu Phe Val Lys Asn Gly Leu Tyr Tyr Leu Gly Ile Met Pro Lys
            515             520             525

Gln Lys Gly Arg Tyr Lys Ala Leu Ser Phe Glu Pro Thr Glu Lys Thr
        530             535             540

Ser Glu Gly Phe Asp Lys Met Tyr Tyr Asp Tyr Phe Pro Asp Ala Ala
545             550             555             560

Lys Met Ile Pro Lys Cys Ser Thr Gln Leu Lys Ala Val Thr Ala His
                565             570             575

Phe Gln Thr His Thr Thr Pro Ile Leu Leu Ser Asn Asn Phe Ile Glu
            580             585             590

Pro Leu Glu Ile Thr Lys Glu Ile Tyr Asp Leu Asn Asn Pro Glu Lys
        595             600             605

Glu Pro Lys Lys Phe Gln Thr Ala Tyr Ala Lys Lys Thr Gly Asp Gln
    610             615             620

Lys Gly Tyr Arg Glu Ala Leu Cys Lys Trp Ile Asp Phe Thr Arg Asp
625             630             635             640

Phe Leu Ser Lys Tyr Thr Lys Thr Thr Ser Ile Asp Leu Ser Ser Leu
                645             650             655

Arg Pro Ser Ser Gln Tyr Lys Asp Leu Gly Glu Tyr Tyr Ala Glu Leu
            660             665             670

Asn Pro Leu Leu Tyr His Ile Ser Phe Gln Arg Ile Ala Glu Lys Glu
        675             680             685

Ile Met Asp Ala Val Glu Thr Gly Lys Leu Tyr Leu Phe Gln Ile Tyr
    690             695             700

Asn Lys Asp Phe Ala Lys Gly His His Gly Lys Pro Asn Leu His Thr
705             710             715             720

Leu Tyr Trp Thr Gly Leu Phe Ser Pro Glu Asn Leu Ala Lys Thr Ser
                725             730             735

Ile Lys Leu Asn Gly Gln Ala Glu Leu Phe Tyr Arg Pro Lys Ser Arg
            740             745             750

Met Lys Arg Met Ala His Arg Leu Gly Glu Lys Met Leu Asn Lys Lys
        755             760             765

Leu Lys Asp Gln Lys Thr Pro Ile Pro Asp Thr Leu Tyr Gln Glu Leu
    770             775             780

Tyr Asp Tyr Val Asn His Arg Leu Ser His Asp Leu Ser Asp Glu Ala
785             790             795             800

Arg Ala Leu Leu Pro Asn Val Ile Thr Lys Glu Val Ser His Glu Ile
                805             810             815

Ile Lys Asp Arg Arg Phe Thr Ser Asp Lys Phe Phe Phe His Val Pro
            820             825             830

Ile Thr Leu Asn Tyr Gln Ala Ala Asn Ser Pro Ser Lys Phe Asn Gln
        835             840             845

Arg Val Asn Ala Tyr Leu Lys Glu His Pro Glu Thr Pro Ile Ile Gly
    850             855             860

Ile Asp Arg Gly Glu Arg Asn Leu Ile Tyr Ile Thr Val Ile Asp Ser
865             870             875             880

Thr Gly Lys Ile Leu Glu Gln Arg Ser Leu Asn Thr Ile Gln Gln Phe
                885             890             895

Asp Tyr Gln Lys Lys Leu Asp Asn Arg Glu Lys Glu Arg Val Ala Ala
            900             905             910

Arg Gln Ala Trp Ser Val Val Gly Thr Ile Lys Asp Leu Lys Gln Gly
        915             920             925
```

-continued

```
Tyr Leu Ser Gln Val Ile His Glu Ile Val Asp Leu Met Ile His Tyr
            930                 935                 940
Gln Ala Val Val Val Leu Glu Asn Leu Asn Phe Gly Phe Lys Ser Lys
945                 950                 955                 960
Arg Thr Gly Ile Ala Glu Lys Ala Val Tyr Gln Gln Phe Glu Lys Met
                965                 970                 975
Leu Ile Asp Lys Leu Asn Cys Leu Val Leu Lys Asp Tyr Pro Ala Glu
            980                 985                 990
Lys Val Gly Gly Val Leu Asn Pro Tyr Gln Leu Thr Asp Gln Phe Thr
        995                 1000                1005
Ser Phe Ala Lys Met Gly Thr Gln Ser Gly Phe Leu Phe Tyr Val
    1010                1015                1020
Pro Ala Pro Tyr Thr Ser Lys Ile Asp Pro Leu Thr Gly Phe Val
    1025                1030                1035
Asp Pro Phe Val Trp Lys Thr Ile Lys Asn His Glu Ser Arg Lys
    1040                1045                1050
His Phe Leu Glu Gly Phe Asp Phe Leu His Tyr Asp Val Lys Thr
    1055                1060                1065
Gly Asp Phe Ile Leu His Phe Lys Met Asn Arg Asn Leu Ser Phe
    1070                1075                1080
Gln Arg Gly Leu Pro Gly Phe Met Pro Ala Trp Asp Ile Val Phe
    1085                1090                1095
Glu Lys Asn Glu Thr Gln Phe Asp Ala Lys Gly Thr Pro Phe Ile
    1100                1105                1110
Ala Gly Lys Arg Ile Val Pro Val Ile Glu Asn His Arg Phe Thr
    1115                1120                1125
Gly Arg Tyr Arg Asp Leu Tyr Pro Ala Asn Glu Leu Ile Ala Leu
    1130                1135                1140
Leu Glu Glu Lys Gly Ile Val Phe Arg Asp Gly Ser Asn Ile Leu
    1145                1150                1155
Pro Lys Leu Leu Glu Asn Asp Asp Ser His Ala Ile Asp Thr Met
    1160                1165                1170
Val Ala Leu Ile Arg Ser Val Leu Gln Met Arg Asn Ser Asn Ala
    1175                1180                1185
Ala Thr Gly Glu Asp Tyr Ile Asn Ser Pro Val Arg Asp Leu Asn
    1190                1195                1200
Gly Val Cys Phe Asp Ser Arg Phe Gln Asn Pro Glu Trp Pro Met
    1205                1210                1215
Asp Ala Asp Ala Asn Gly Ala Tyr His Ile Ala Leu Lys Gly Gln
    1220                1225                1230
Leu Leu Leu Asn His Leu Lys Glu Ser Lys Asp Leu Lys Leu Gln
    1235                1240                1245
Asn Gly Ile Ser Asn Gln Asp Trp Leu Ala Tyr Ile Gln Glu Leu
    1250                1255                1260
Arg Asn
    1265
```

<210> SEQ ID NO 34
<211> LENGTH: 1187
<212> TYPE: PRT
<213> ORGANISM: Unknown
<220> FEATURE:
<223> OTHER INFORMATION: Description of Unknown:
      Lachnospiraceae sequence

<400> SEQUENCE: 34

```
Met Ser Lys Leu Glu Lys Phe Thr Asn Cys Tyr Ser Leu Ser Lys Thr
1               5                   10                  15
Leu Arg Phe Lys Ala Ile Pro Val Gly Lys Thr Gln Glu Asn Ile Asp
            20                  25                  30
Asn Lys Arg Leu Leu Val Glu Asp Glu Lys Arg Ala Glu Asp Tyr Lys
        35                  40                  45
Gly Val Lys Lys Leu Leu Asp Arg Tyr Tyr Leu Ser Phe Ile Asn Asp
    50                  55                  60
Val Leu His Ser Ile Gly Asn Glu Gly Tyr Lys Ser Leu Phe Lys Lys
65                  70                  75                  80
Asp Ile Ile Glu Thr Ile Leu Pro Glu Phe Leu Asp Asp Lys Asp Glu
                85                  90                  95
Ile Ala Leu Val Asn Ser Phe Asn Gly Phe Thr Thr Ala Phe Thr Gly
            100                 105                 110
Phe Phe Asp Asn Arg Glu Asn Met Phe Ser Glu Glu Ala Lys Ser Thr
        115                 120                 125
Ser Ile Ala Phe Arg Cys Ile Asn Glu Asn Leu Thr Arg Tyr Ile Ser
    130                 135                 140
Asn Met Asp Ile Phe Glu Lys Val Asp Ala Ile Phe Asp Lys His Glu
145                 150                 155                 160
Val Gln Glu Ile Lys Glu Lys Ile Leu Asn Ser Asp Tyr Asp Val Glu
                165                 170                 175
Asp Phe Phe Glu Gly Glu Phe Phe Asn Phe Val Leu Thr Gln Glu Gly
            180                 185                 190
Ile Asp Val Tyr Asn Ala Ile Ile Gly Gly Phe Val Thr Glu Ser Gly
        195                 200                 205
Glu Lys Ile Lys Gly Leu Asn Glu Tyr Ile Asn Leu Tyr Asn Gln Lys
    210                 215                 220
Thr Lys Gln Lys Leu Pro Lys Phe Lys Pro Leu Tyr Lys Gln Val Leu
225                 230                 235                 240
Ser Asp Arg Glu Ser Leu Ser Phe Tyr Gly Glu Gly Tyr Thr Ser Asp
                245                 250                 255
Glu Glu Val Leu Glu Val Phe Arg Asn Thr Leu Asn Lys Asn Ser Glu
            260                 265                 270
Ile Phe Ser Ser Ile Lys Lys Leu Glu Lys Leu Phe Lys Asn Phe Asp
        275                 280                 285
Glu Tyr Ser Ser Ala Gly Ile Phe Val Lys Asn Gly Pro Ala Ile Ser
    290                 295                 300
Thr Ile Ser Lys Asp Ile Phe Gly Glu Trp Asn Val Ile Arg Asp Lys
305                 310                 315                 320
Trp Asn Ala Glu Tyr Asp Asp Ile His Leu Lys Lys Lys Ala Val Val
                325                 330                 335
Thr Glu Lys Tyr Glu Asp Asp Arg Arg Lys Ser Phe Lys Lys Ile Gly
            340                 345                 350
Ser Phe Ser Leu Glu Gln Leu Gln Glu Tyr Ala Asp Ala Asp Leu Ser
        355                 360                 365
Val Val Glu Lys Leu Lys Glu Ile Ile Ile Gln Lys Val Asp Glu Ile
    370                 375                 380
Tyr Lys Val Tyr Gly Ser Ser Glu Lys Leu Phe Asp Ala Asp Phe Val
385                 390                 395                 400
Leu Glu Lys Ser Leu Lys Lys Asn Asp Ala Val Val Ala Ile Met Lys
                405                 410                 415
```

```
Asp Leu Leu Asp Ser Val Lys Ser Phe Glu Asn Tyr Ile Lys Ala Phe
            420                 425                 430

Phe Gly Glu Gly Lys Glu Thr Asn Arg Asp Glu Ser Phe Tyr Gly Asp
            435                 440                 445

Phe Val Leu Ala Tyr Asp Ile Leu Leu Lys Val Asp His Ile Tyr Asp
450                 455                 460

Ala Ile Arg Asn Tyr Val Thr Gln Lys Pro Tyr Ser Lys Asp Lys Phe
465                 470                 475                 480

Lys Leu Tyr Phe Gln Asn Pro Gln Phe Met Gly Gly Trp Asp Lys Asp
                485                 490                 495

Lys Glu Thr Asp Tyr Arg Ala Thr Ile Leu Arg Tyr Gly Ser Lys Tyr
            500                 505                 510

Tyr Leu Ala Ile Met Asp Lys Lys Tyr Ala Lys Cys Leu Gln Lys Ile
            515                 520                 525

Asp Lys Asp Val Asn Gly Asn Tyr Glu Lys Ile Asn Tyr Lys Leu
530                 535                 540

Leu Pro Gly Pro Asn Lys Met Leu Pro Lys Val Phe Phe Ser Lys Lys
545                 550                 555                 560

Trp Met Ala Tyr Tyr Asn Pro Ser Glu Asp Ile Gln Lys Ile Tyr Lys
                565                 570                 575

Asn Gly Thr Phe Lys Lys Gly Asp Met Phe Asn Leu Asn Asp Cys His
            580                 585                 590

Lys Leu Ile Asp Phe Phe Lys Asp Ser Ile Ser Arg Tyr Pro Lys Trp
            595                 600                 605

Ser Asn Ala Tyr Asp Phe Asn Phe Ser Glu Thr Glu Lys Tyr Lys Asp
            610                 615                 620

Ile Ala Gly Phe Tyr Arg Glu Val Glu Glu Gln Gly Tyr Lys Val Ser
625                 630                 635                 640

Phe Glu Ser Ala Ser Lys Lys Glu Val Asp Lys Leu Val Glu Gly
                645                 650                 655

Lys Leu Tyr Met Phe Gln Ile Tyr Asn Lys Asp Phe Ser Asp Lys Ser
            660                 665                 670

His Gly Thr Pro Asn Leu His Thr Met Tyr Phe Lys Leu Leu Phe Asp
            675                 680                 685

Glu Asn Asn His Gly Gln Ile Arg Leu Ser Gly Gly Ala Glu Leu Phe
            690                 695                 700

Met Arg Arg Ala Ser Leu Lys Lys Glu Glu Leu Val Val His Pro Ala
705                 710                 715                 720

Asn Ser Pro Ile Ala Asn Lys Asn Pro Asp Asn Pro Lys Lys Thr Thr
                725                 730                 735

Thr Leu Ser Tyr Asp Val Tyr Lys Asp Lys Arg Phe Ser Glu Asp Gln
            740                 745                 750

Tyr Glu Leu His Ile Pro Ile Ala Ile Asn Lys Cys Pro Lys Asn Ile
            755                 760                 765

Phe Lys Ile Asn Thr Glu Val Arg Val Leu Leu Lys His Asp Asp Asn
            770                 775                 780

Pro Tyr Val Ile Gly Ile Asp Arg Gly Glu Arg Asn Leu Leu Tyr Ile
785                 790                 795                 800

Val Val Val Asp Gly Lys Gly Asn Ile Val Glu Gln Tyr Ser Leu Asn
                805                 810                 815

Glu Ile Ile Asn Asn Phe Asn Gly Ile Arg Ile Lys Thr Asp Tyr His
            820                 825                 830
```

```
Ser Leu Leu Asp Lys Lys Glu Lys Glu Arg Phe Glu Ala Arg Gln Asn
            835                 840                 845

Trp Thr Ser Ile Glu Asn Ile Lys Glu Leu Lys Ala Gly Tyr Ile Ser
    850                 855                 860

Gln Val Val His Lys Ile Cys Glu Leu Val Glu Lys Tyr Asp Ala Val
865                 870                 875                 880

Ile Ala Leu Glu Asp Leu Asn Ser Gly Phe Lys Asn Ser Arg Val Lys
                885                 890                 895

Val Glu Lys Gln Val Tyr Gln Lys Phe Glu Lys Met Leu Ile Asp Lys
            900                 905                 910

Leu Asn Tyr Met Val Asp Lys Lys Ser Asn Pro Cys Ala Thr Gly Gly
        915                 920                 925

Ala Leu Lys Gly Tyr Gln Ile Thr Asn Lys Phe Glu Ser Phe Lys Ser
    930                 935                 940

Met Ser Thr Gln Asn Gly Phe Ile Phe Tyr Ile Pro Ala Trp Leu Thr
945                 950                 955                 960

Ser Lys Ile Asp Pro Ser Thr Gly Phe Val Asn Leu Leu Lys Thr Lys
                965                 970                 975

Tyr Thr Ser Ile Ala Asp Ser Lys Lys Phe Ile Ser Ser Phe Asp Arg
            980                 985                 990

Ile Met Tyr Val Pro Glu Glu Asp Leu Phe Glu Phe Ala Leu Asp Tyr
        995                 1000                1005

Lys Asn Phe Ser Arg Thr Asp Ala Asp Tyr Ile Lys Lys Trp Lys
    1010                1015                1020

Leu Tyr Ser Tyr Gly Asn Arg Ile Arg Ile Phe Arg Asn Pro Lys
    1025                1030                1035

Lys Asn Asn Val Phe Asp Trp Glu Glu Val Cys Leu Thr Ser Ala
    1040                1045                1050

Tyr Lys Glu Leu Phe Asn Lys Tyr Gly Ile Asn Tyr Gln Gln Gly
    1055                1060                1065

Asp Ile Arg Ala Leu Leu Cys Glu Gln Ser Asp Lys Ala Phe Tyr
    1070                1075                1080

Ser Ser Phe Met Ala Leu Met Ser Leu Met Leu Gln Met Arg Asn
    1085                1090                1095

Ser Ile Thr Gly Arg Thr Asp Val Asp Phe Leu Ile Ser Pro Val
    1100                1105                1110

Lys Asn Ser Asp Gly Ile Phe Tyr Asp Ser Arg Asn Tyr Glu Ala
    1115                1120                1125

Gln Glu Asn Ala Ile Leu Pro Lys Asn Ala Asp Ala Asn Gly Ala
    1130                1135                1140

Tyr Asn Ile Ala Arg Lys Val Leu Trp Ala Ile Gly Gln Phe Lys
    1145                1150                1155

Lys Ala Glu Asp Glu Lys Leu Asp Lys Val Lys Ile Ala Ile Ser
    1160                1165                1170

Asn Lys Glu Trp Leu Glu Tyr Ala Gln Thr Ser Val Lys His
    1175                1180                1185

<210> SEQ ID NO 35
<211> LENGTH: 1255
<212> TYPE: PRT
<213> ORGANISM: Francisella tularensis U112 1

<400> SEQUENCE: 35

Met Ser Ile Tyr Gln Glu Phe Val Asn Lys Tyr Ser Leu Ser Lys Thr
1               5                   10                  15
```

```
Leu Arg Phe Glu Leu Ile Pro Gln Gly Lys Thr Leu Glu Asn Ile Lys
            20                  25                  30

Ala Arg Gly Leu Ile Leu Asp Glu Lys Arg Ala Lys Asp Tyr Lys
        35                  40                  45

Lys Ala Lys Gln Ile Ile Asp Lys Tyr His Gln Phe Phe Ile Glu Glu
    50                  55                  60

Ile Leu Ser Ser Val Asp Ser Glu Lys Phe Lys Asn Leu Phe Asn Gln
65                  70                  75                  80

Asn Leu Ile Asp Ala Lys Lys Gly Gln Glu Ser Asp Leu Ile Leu Trp
                85                  90                  95

Leu Lys Gln Ser Lys Asp Asn Gly Ile Glu Leu Phe Lys Ala Asn Ser
            100                 105                 110

Asp Ile Thr Asp Ile Asp Glu Ala Leu Glu Ile Ile Lys Ser Phe Lys
        115                 120                 125

Gly Trp Thr Thr Tyr Phe Lys Gly Phe His Glu Asn Arg Lys Asn Val
130                 135                 140

Tyr Ser Ser Asn Asp Ile Pro Thr Ser Ile Ile Tyr Arg Ile Val Asp
145                 150                 155                 160

Asp Asn Leu Pro Lys Phe Leu Glu Asn Lys Ala Lys Tyr Glu Ser Leu
                165                 170                 175

Lys Asp Lys Ala Pro Glu Ala Ile Asn Tyr Glu Gln Ile Lys Lys Asp
            180                 185                 190

Leu Ala Glu Glu Leu Thr Phe Asp Ile Asp Tyr Lys Thr Ser Glu Val
        195                 200                 205

Asn Gln Arg Val Phe Ser Leu Asp Glu Val Phe Glu Ile Ala Asn Phe
210                 215                 220

Asn Asn Tyr Leu Asn Gln Ser Gly Ile Thr Lys Phe Asn Thr Ile Ile
225                 230                 235                 240

Gly Gly Lys Phe Val Asn Gly Glu Asn Thr Lys Arg Lys Gly Ile Asn
                245                 250                 255

Glu Tyr Ile Asn Leu Tyr Ser Gln Gln Ile Asn Asp Lys Thr Leu Lys
            260                 265                 270

Lys Tyr Lys Met Ser Val Leu Phe Lys Gln Ile Leu Ser Asp Thr Glu
        275                 280                 285

Ser Lys Ser Phe Val Ile Asp Lys Leu Glu Asp Asp Ser Asp Val Val
290                 295                 300

Thr Thr Met Gln Ser Phe Tyr Glu Gln Ile Ala Ala Phe Lys Thr Val
305                 310                 315                 320

Glu Glu Lys Ser Ile Lys Glu Thr Leu Ser Leu Leu Phe Asp Asp Leu
                325                 330                 335

Lys Ala Gln Lys Leu Asp Leu Ser Lys Ile Tyr Phe Lys Asn Asp Lys
            340                 345                 350

Ser Leu Thr Asp Leu Ser Gln Gln Val Phe Asp Asp Tyr Ser Val Ile
        355                 360                 365

Gly Thr Ala Val Leu Glu Tyr Ile Thr Gln Gln Ile Ala Pro Lys Asn
370                 375                 380

Leu Asp Asn Pro Ser Lys Lys Glu Gln Glu Leu Ile Ala Lys Lys Thr
385                 390                 395                 400

Glu Lys Ala Lys Tyr Leu Ser Leu Glu Thr Ile Lys Leu Ala Leu Glu
                405                 410                 415

Glu Phe Asn Lys His Arg Asp Ile Asp Lys Gln Cys Arg Phe Glu Glu
            420                 425                 430
```

```
Ile Leu Ala Asn Phe Ala Ala Ile Pro Met Ile Phe Asp Glu Ile Ala
            435                 440                 445

Gln Asn Lys Asp Asn Leu Ala Gln Ile Ser Ile Lys Tyr Gln Asn Gln
        450                 455                 460

Gly Lys Lys Asp Leu Leu Gln Ala Ser Ala Glu Asp Val Lys Ala
465                 470                 475                 480

Ile Lys Asp Leu Leu Asp Gln Thr Asn Asn Leu Leu His Lys Leu Lys
                485                 490                 495

Ile Phe His Ile Ser Gln Ser Glu Asp Lys Ala Asn Ile Leu Asp Lys
                500                 505                 510

Asp Glu His Phe Tyr Leu Val Phe Glu Glu Cys Tyr Phe Glu Leu Ala
            515                 520                 525

Asn Ile Val Pro Leu Tyr Asn Lys Ile Arg Asn Tyr Ile Thr Gln Lys
        530                 535                 540

Pro Tyr Ser Asp Glu Lys Phe Lys Leu Asn Phe Glu Asn Ser Thr Leu
545                 550                 555                 560

Ala Asn Gly Trp Asp Lys Asn Lys Glu Pro Asp Asn Thr Ala Ile Leu
                565                 570                 575

Phe Ile Lys Asp Asp Lys Tyr Tyr Leu Gly Val Met Asn Lys Lys Asn
            580                 585                 590

Asn Lys Ile Phe Asp Asp Lys Ala Ile Lys Glu Asn Lys Gly Glu Gly
        595                 600                 605

Tyr Lys Lys Ile Val Tyr Lys Leu Leu Pro Gly Ala Asn Lys Met Leu
        610                 615                 620

Pro Lys Val Phe Phe Ser Ala Lys Ser Ile Lys Phe Tyr Asn Pro Ser
625                 630                 635                 640

Glu Asp Ile Leu Arg Ile Arg Asn His Ser Thr His Thr Lys Asn Gly
                645                 650                 655

Ser Pro Gln Lys Gly Tyr Glu Lys Phe Glu Phe Asn Ile Glu Asp Cys
            660                 665                 670

Arg Lys Phe Ile Asp Phe Tyr Lys Gln Ser Ile Ser Lys His Pro Glu
        675                 680                 685

Trp Lys Asp Phe Gly Phe Arg Phe Ser Asp Thr Gln Arg Tyr Asn Ser
        690                 695                 700

Ile Asp Glu Phe Tyr Arg Glu Val Glu Asn Gln Gly Tyr Lys Leu Thr
705                 710                 715                 720

Phe Glu Asn Ile Ser Glu Ser Tyr Ile Asp Ser Val Val Asn Gln Gly
                725                 730                 735

Lys Leu Tyr Leu Phe Gln Ile Tyr Asn Lys Asp Phe Ser Ala Tyr Ser
            740                 745                 750

Lys Gly Arg Pro Asn Leu His Thr Leu Tyr Trp Lys Ala Leu Phe Asp
        755                 760                 765

Glu Arg Asn Leu Gln Asp Val Val Tyr Lys Leu Asn Gly Glu Ala Glu
        770                 775                 780

Leu Phe Tyr Arg Lys Gln Ser Ile Pro Lys Lys Ile Thr His Pro Ala
785                 790                 795                 800

Lys Glu Ala Ile Ala Asn Lys Asn Lys Asp Asn Pro Lys Lys Glu Ser
                805                 810                 815

Val Phe Glu Tyr Asp Leu Ile Lys Asp Lys Arg Phe Thr Glu Asp Lys
            820                 825                 830

Phe Phe Phe His Cys Pro Ile Thr Ile Asn Phe Lys Ser Ser Gly Ala
        835                 840                 845

Asn Lys Phe Asn Asp Glu Ile Asn Leu Leu Leu Lys Glu Lys Ala Asn
```

```
                850                 855                 860
        Asp Val His Ile Leu Ser Ile Asp Arg Gly Glu Arg His Leu Ala Tyr
        865                 870                 875                 880

Tyr Thr Leu Val Asp Gly Lys Gly Asn Ile Ile Lys Gln Asp Thr Phe
                            885                 890                 895

Asn Ile Ile Gly Asn Asp Arg Met Lys Thr Asn Tyr His Asp Lys Leu
                    900                 905                 910

Ala Ala Ile Glu Lys Asp Arg Asp Ser Ala Arg Lys Asp Trp Lys Lys
                    915                 920                 925

Ile Asn Asn Ile Lys Glu Met Lys Glu Gly Tyr Leu Ser Gln Val Val
                930                 935                 940

His Glu Ile Ala Lys Leu Val Ile Glu Tyr Asn Ala Ile Val Val Phe
        945                 950                 955                 960

Glu Asp Leu Asn Phe Gly Phe Lys Arg Gly Arg Phe Lys Val Glu Lys
                            965                 970                 975

Gln Val Tyr Gln Lys Leu Glu Lys Met Leu Ile Glu Lys Leu Asn Tyr
                        980                 985                 990

Leu Val Phe Lys Asp Asn Glu Phe Asp Lys Thr Gly Gly Val Leu Arg
                    995                 1000                1005

Ala Tyr Gln Leu Thr Ala Pro Phe Glu Thr Phe Lys Lys Met Gly
            1010                1015                1020

Lys Gln Thr Gly Ile Ile Tyr Val Pro Ala Gly Phe Thr Ser
            1025                1030                1035

Lys Ile Cys Pro Val Thr Gly Phe Val Asn Gln Leu Tyr Pro Lys
            1040                1045                1050

Tyr Glu Ser Val Ser Lys Ser Gln Glu Phe Phe Ser Lys Phe Asp
            1055                1060                1065

Lys Ile Cys Tyr Asn Leu Asp Lys Gly Tyr Phe Glu Phe Ser Phe
            1070                1075                1080

Asp Tyr Lys Asn Phe Gly Asp Lys Ala Ala Lys Gly Lys Trp Thr
            1085                1090                1095

Ile Ala Ser Phe Gly Ser Arg Leu Ile Asn Phe Arg Asn Ser Asp
            1100                1105                1110

Lys Asn His Asn Trp Asp Thr Arg Glu Val Tyr Pro Thr Lys Glu
            1115                1120                1125

Leu Glu Lys Leu Leu Lys Asp Tyr Ser Ile Glu Tyr Gly His Gly
            1130                1135                1140

Glu Cys Ile Lys Ala Ala Ile Cys Gly Glu Ser Asp Lys Lys Phe
            1145                1150                1155

Phe Ala Lys Leu Thr Ser Val Leu Asn Thr Ile Leu Gln Met Arg
            1160                1165                1170

Asn Ser Lys Thr Gly Thr Glu Leu Asp Tyr Leu Ile Ser Pro Val
            1175                1180                1185

Ala Asp Val Asn Gly Asn Phe Phe Asp Ser Arg Gln Ala Pro Lys
            1190                1195                1200

Asn Met Pro Gln Asp Ala Asp Ala Asn Gly Ala Tyr His Ile Gly
            1205                1210                1215

Leu Lys Gly Leu Met Leu Leu Gly Arg Ile Lys Asn Asn Gln Glu
            1220                1225                1230

Gly Lys Lys Leu Asn Leu Val Ile Lys Asn Glu Glu Tyr Phe Glu
            1235                1240                1245

Phe Val Gln Asn Arg Asn Asn
            1250                1255
```

<210> SEQ ID NO 36
<211> LENGTH: 1196
<212> TYPE: PRT
<213> ORGANISM: Candidatus Methanoplasma termitum 10

<400> SEQUENCE: 36

Met Asn Asn Tyr Asp Glu Phe Thr Lys Leu Tyr Pro Ile Gln Lys Thr
1               5                   10                  15

Ile Arg Phe Glu Leu Lys Pro Gln Gly Arg Thr Met Glu His Leu Glu
            20                  25                  30

Thr Phe Asn Phe Phe Glu Glu Asp Arg Asp Arg Ala Glu Lys Tyr Lys
        35                  40                  45

Ile Leu Lys Glu Ala Ile Asp Glu Tyr His Lys Lys Phe Ile Asp Glu
    50                  55                  60

His Leu Thr Asn Met Lys Asp Asp Arg Phe Lys Asp Leu Phe Ser Lys
65                  70                  75                  80

Lys Leu Phe Ser Glu Leu Leu Lys Glu Ile Tyr Lys Lys Gly Asn
                85                  90                  95

His Gln Glu Ile Asp Ala Leu Lys Ser Phe Asp Lys Phe Ser Gly Tyr
            100                 105                 110

Phe Ile Gly Leu His Glu Asn Arg Lys Asn Met Tyr Ser Asp Gly Asp
        115                 120                 125

Glu Ile Thr Ala Ile Ser Asn Arg Ile Val Asn Glu Asn Phe Pro Lys
    130                 135                 140

Phe Leu Asp Asn Leu Gln Lys Tyr Gln Glu Ala Arg Lys Lys Tyr Pro
145                 150                 155                 160

Glu Trp Ile Ile Lys Ala Glu Ser Ala Leu Val Ala His Asn Ile Lys
                165                 170                 175

Met Asp Glu Val Phe Ser Leu Glu Tyr Phe Asn Lys Val Leu Asn Gln
            180                 185                 190

Glu Gly Ile Gln Arg Tyr Asn Leu Ala Leu Gly Gly Tyr Val Thr Lys
        195                 200                 205

Ser Gly Glu Lys Met Met Gly Leu Asn Asp Ala Leu Asn Leu Ala His
    210                 215                 220

Gln Ser Glu Lys Ser Ser Lys Gly Arg Ile His Met Thr Pro Leu Phe
225                 230                 235                 240

Lys Gln Ile Leu Ser Glu Lys Glu Ser Phe Ser Tyr Ile Pro Asp Val
                245                 250                 255

Phe Thr Glu Asp Ser Gln Leu Leu Pro Ser Ile Gly Gly Phe Phe Ala
            260                 265                 270

Gln Ile Glu Asn Asp Lys Asp Gly Asn Ile Phe Asp Arg Ala Leu Glu
        275                 280                 285

Leu Ile Ser Ser Tyr Ala Glu Tyr Asp Thr Glu Arg Ile Tyr Ile Arg
    290                 295                 300

Gln Ala Asp Ile Asn Arg Val Ser Asn Val Ile Phe Gly Glu Trp Gly
305                 310                 315                 320

Thr Leu Gly Gly Leu Met Arg Glu Tyr Lys Ala Asp Ser Ile Asn Asp
                325                 330                 335

Ile Asn Leu Glu Arg Thr Cys Lys Lys Val Asp Lys Trp Leu Asp Ser
            340                 345                 350

Lys Glu Phe Ala Leu Ser Asp Val Leu Glu Ala Ile Lys Arg Thr Gly
        355                 360                 365

Asn Asn Asp Ala Phe Asn Glu Tyr Ile Ser Lys Met Arg Thr Ala Arg

```
                370             375             380
Glu Lys Ile Asp Ala Ala Arg Lys Glu Met Lys Phe Ile Ser Glu Lys
385                 390                 395                 400

Ile Ser Gly Asp Glu Glu Ser Ile His Ile Ile Lys Thr Leu Leu Asp
                405                 410                 415

Ser Val Gln Gln Phe Leu His Phe Phe Asn Leu Phe Lys Ala Arg Gln
                420                 425                 430

Asp Ile Pro Leu Asp Gly Ala Phe Tyr Ala Glu Phe Asp Glu Val His
                435                 440                 445

Ser Lys Leu Phe Ala Ile Val Pro Leu Tyr Asn Lys Val Arg Asn Tyr
450                 455                 460

Leu Thr Lys Asn Asn Leu Asn Thr Lys Lys Ile Lys Leu Asn Phe Lys
465                 470                 475                 480

Asn Pro Thr Leu Ala Asn Gly Trp Asp Gln Asn Lys Val Tyr Asp Tyr
                485                 490                 495

Ala Ser Leu Ile Phe Leu Arg Asp Gly Asn Tyr Tyr Leu Gly Ile Ile
                500                 505                 510

Asn Pro Lys Arg Lys Asn Ile Lys Phe Glu Gln Gly Ser Gly Asn
                515                 520                 525

Gly Pro Phe Tyr Arg Lys Met Val Tyr Lys Gln Ile Pro Gly Pro Asn
                530                 535                 540

Lys Asn Leu Pro Arg Val Phe Leu Thr Ser Thr Lys Gly Lys Lys Glu
545                 550                 555                 560

Tyr Lys Pro Ser Lys Glu Ile Ile Glu Gly Tyr Glu Ala Asp Lys His
                565                 570                 575

Ile Arg Gly Asp Lys Phe Asp Leu Asp Phe Cys His Lys Leu Ile Asp
                580                 585                 590

Phe Phe Lys Glu Ser Ile Glu Lys His Lys Asp Trp Ser Lys Phe Asn
                595                 600                 605

Phe Tyr Phe Ser Pro Thr Glu Ser Tyr Gly Asp Ile Ser Glu Phe Tyr
                610                 615                 620

Leu Asp Val Glu Lys Gln Gly Tyr Arg Met His Phe Glu Asn Ile Ser
625                 630                 635                 640

Ala Glu Thr Ile Asp Glu Tyr Val Glu Lys Gly Asp Leu Phe Leu Phe
                645                 650                 655

Gln Ile Tyr Asn Lys Asp Phe Val Lys Ala Ala Thr Gly Lys Lys Asp
                660                 665                 670

Met His Thr Ile Tyr Trp Asn Ala Ala Phe Ser Pro Glu Asn Leu Gln
                675                 680                 685

Asp Val Val Val Lys Leu Asn Gly Glu Ala Glu Leu Phe Tyr Arg Asp
                690                 695                 700

Lys Ser Asp Ile Lys Glu Ile Val His Arg Glu Gly Glu Ile Leu Val
705                 710                 715                 720

Asn Arg Thr Tyr Asn Gly Arg Thr Pro Val Pro Asp Lys Ile His Lys
                725                 730                 735

Lys Leu Thr Asp Tyr His Asn Gly Arg Thr Lys Asp Leu Gly Glu Ala
                740                 745                 750

Lys Glu Tyr Leu Asp Lys Val Arg Tyr Phe Lys Ala His Tyr Asp Ile
                755                 760                 765

Thr Lys Asp Arg Arg Tyr Leu Asn Asp Lys Ile Tyr Phe His Val Pro
                770                 775                 780

Leu Thr Leu Asn Phe Lys Ala Asn Gly Lys Lys Asn Leu Asn Lys Met
785                 790                 795                 800
```

```
Val Ile Glu Lys Phe Leu Ser Asp Glu Lys Ala His Ile Ile Gly Ile
                805                 810                 815

Asp Arg Gly Glu Arg Asn Leu Leu Tyr Tyr Ser Ile Ile Asp Arg Ser
                820                 825                 830

Gly Lys Ile Ile Asp Gln Gln Ser Leu Asn Val Ile Asp Gly Phe Asp
                835                 840                 845

Tyr Arg Glu Lys Leu Asn Gln Arg Glu Ile Glu Met Lys Asp Ala Arg
                850                 855                 860

Gln Ser Trp Asn Ala Ile Gly Lys Ile Lys Asp Leu Lys Glu Gly Tyr
865                 870                 875                 880

Leu Ser Lys Ala Val His Glu Ile Thr Lys Met Ala Ile Gln Tyr Asn
                885                 890                 895

Ala Ile Val Val Met Glu Glu Leu Asn Tyr Gly Phe Lys Arg Gly Arg
                900                 905                 910

Phe Lys Val Glu Lys Gln Ile Tyr Gln Lys Phe Glu Asn Met Leu Ile
                915                 920                 925

Asp Lys Met Asn Tyr Leu Val Phe Lys Asp Ala Pro Asp Glu Ser Pro
                930                 935                 940

Gly Gly Val Leu Asn Ala Tyr Gln Leu Thr Asn Pro Leu Glu Ser Phe
945                 950                 955                 960

Ala Lys Leu Gly Lys Gln Thr Gly Ile Leu Phe Tyr Val Pro Ala Ala
                965                 970                 975

Tyr Thr Ser Lys Ile Asp Pro Thr Thr Gly Phe Val Asn Leu Phe Asn
                980                 985                 990

Thr Ser Ser Lys Thr Asn Ala Gln Glu Arg Lys Glu Phe Leu Gln Lys
                995                 1000                1005

Phe Glu Ser Ile Ser Tyr Ser Ala Lys Asp Gly Gly Ile Phe Ala
    1010                1015                1020

Phe Ala Phe Asp Tyr Arg Lys Phe Gly Thr Ser Lys Thr Asp His
    1025                1030                1035

Lys Asn Val Trp Thr Ala Tyr Thr Asn Gly Glu Arg Met Arg Tyr
    1040                1045                1050

Ile Lys Glu Lys Lys Arg Asn Glu Leu Phe Asp Pro Ser Lys Glu
    1055                1060                1065

Ile Lys Glu Ala Leu Thr Ser Ser Gly Ile Lys Tyr Asp Gly Gly
    1070                1075                1080

Gln Asn Ile Leu Pro Asp Ile Leu Arg Ser Asn Asn Asn Gly Leu
    1085                1090                1095

Ile Tyr Thr Met Tyr Ser Ser Phe Ile Ala Ala Ile Gln Met Arg
    1100                1105                1110

Val Tyr Asp Gly Lys Glu Asp Tyr Ile Ile Ser Pro Ile Lys Asn
    1115                1120                1125

Ser Lys Gly Glu Phe Phe Arg Thr Asp Pro Lys Arg Arg Glu Leu
    1130                1135                1140

Pro Ile Asp Ala Asp Ala Asn Gly Ala Tyr Asn Ile Ala Leu Arg
    1145                1150                1155

Gly Glu Leu Thr Met Arg Ala Ile Ala Glu Lys Phe Asp Pro Asp
    1160                1165                1170

Ser Glu Lys Met Ala Lys Leu Glu Leu Lys His Lys Asp Trp Phe
    1175                1180                1185

Glu Phe Met Gln Thr Arg Gly Asp
    1190                1195
```

The invention claimed is:

1. An in vitro method for targeting a target nucleic acid, the method comprising contacting a composition comprising the target nucleic acid with a CRISPR complex comprising (a) a Cpf1 polypeptide that comprises a RuvC-like domain and does not comprise an HNH domain and (b) an engineered guide RNA that is capable of directing sequence-specific binding of the complex to the target nucleic acid, wherein the Cpf1 polypeptide comprises an amino acid sequence at least 98% identical to SEQ ID NO:1 and has nuclease activity.

2. The method of claim 1, wherein the Cpf1 polypeptide comprises at least one mutation compared to the polypeptide of SEQ ID NO:1.

3. The method of claim 1, wherein the Cpf1 polypeptide is associated with one or more heterologous functional domains.

4. The method of claim 1, wherein the target nucleic acid is in a eukaryotic cell.

5. The method of claim 1, wherein the target nucleic acid is cleaved.

6. The method of claim 1, wherein a gene product is modified or the amount or expression of a gene product is modified.

7. The method of claim 1, wherein the target nucleic acid comprises a disease-causing genetic mutation.

* * * * *